(12) United States Patent
Ma et al.

(10) Patent No.: US 10,858,359 B2
(45) Date of Patent: Dec. 8, 2020

(54) HETEROCYCLIC RING DERIVATIVES USEFUL AS SHP2 INHIBITORS

(71) Applicant: JACOBIO PHARMACEUTICALS CO., LTD., Beijing (CN)

(72) Inventors: Cunbo Ma, Beijing (CN); Panliang Gao, Beijing (CN); Jie Chu, Beijing (CN); Xinping Wu, Beijing (CN); Chunwei Wen, Beijing (CN); Di Kang, Beijing (CN); Jinlong Bai, Beijing (CN); Xiaoyan Pei, Beijing (CN)

(73) Assignee: JACOBIO PHARMACEUTICALS CO., LTD., Beijing (CN)

( * ) Notice: Subject to any disclaimer, the term of this patent is extended or adjusted under 35 U.S.C. 154(b) by 0 days.

(21) Appl. No.: 16/307,827

(22) PCT Filed: Jun. 7, 2017

(86) PCT No.: PCT/CN2017/087471
§ 371 (c)(1),
(2) Date: Dec. 6, 2018

(87) PCT Pub. No.: WO2017/211303
PCT Pub. Date: Dec. 14, 2017

(65) Prior Publication Data
US 2019/0127378 A1   May 2, 2019

(30) Foreign Application Priority Data
Jun. 7, 2016   (WO) ............... PCT/CN2016/085122

(51) Int. Cl.
| | |
|---|---|
| *C07D 401/12* | (2006.01) |
| *C07D 471/14* | (2006.01) |
| *C07D 401/14* | (2006.01) |
| *C07D 401/04* | (2006.01) |
| *C07D 491/107* | (2006.01) |
| *A61P 35/00* | (2006.01) |
| *C07D 413/14* | (2006.01) |
| *C07D 471/20* | (2006.01) |
| *C07D 405/14* | (2006.01) |
| *A61P 37/00* | (2006.01) |
| *A61P 27/00* | (2006.01) |
| *A61P 9/00* | (2006.01) |
| *C07D 519/00* | (2006.01) |
| *C07D 471/04* | (2006.01) |

(52) U.S. Cl.
CPC ............. *C07D 471/14* (2013.01); *A61P 9/00* (2018.01); *A61P 27/00* (2018.01); *A61P 35/00* (2018.01); *A61P 37/00* (2018.01); *C07D 401/04* (2013.01); *C07D 401/12* (2013.01); *C07D 401/14* (2013.01); *C07D 405/14* (2013.01); *C07D 413/14* (2013.01); *C07D 471/04* (2013.01); *C07D 471/20* (2013.01); *C07D 491/107* (2013.01); *C07D 519/00* (2013.01)

(58) Field of Classification Search
CPC ................................................... C07D 401/12
See application file for complete search history.

(56) References Cited

U.S. PATENT DOCUMENTS

| | | | |
|---|---|---|---|
| 5,876,628 | A | 3/1999 | Illian et al. |
| 6,025,382 | A | 2/2000 | McMorris et al. |
| 7,056,911 | B1 | 6/2006 | Rosowsky |
| 7,435,830 | B2 | 10/2008 | Pennell et al. |
| 7,435,831 | B2 | 10/2008 | Chen et al. |
| 7,439,374 | B2 | 10/2008 | Thurkauf et al. |
| 7,605,159 | B2 | 10/2009 | McInally et al. |
| 7,691,863 | B2 | 4/2010 | Dietz et al. |
| 7,723,369 | B2 | 5/2010 | Mjalli et al. |
| 7,790,929 | B2 | 9/2010 | Reiffenrath et al. |
| 7,838,523 | B2 | 11/2010 | Blomgren et al. |
| 8,012,983 | B2 | 9/2011 | Andrews et al. |
| 8,138,206 | B2 | 3/2012 | Ishikawa et al. |
| 8,153,635 | B2 | 4/2012 | Alper et al. |
| 8,252,803 | B2 | 8/2012 | Rivkin |

(Continued)

FOREIGN PATENT DOCUMENTS

| | | |
|---|---|---|
| CN | 103201267 A | 7/2013 |
| CN | 103201267 B | 8/2016 |

(Continued)

OTHER PUBLICATIONS

International Search Report for International Application No. PCT/CN2017/087471, dated Aug. 18, 2017. (3 pages).

(Continued)

*Primary Examiner* — John S Kenyon

(74) *Attorney, Agent, or Firm* — Finnegan, Henderson, Farabow, Garrett & Dunner, LLP

(57) ABSTRACT

Provided are certain novel pyrazine derivatives (I) as SHP2 inhibitors which is shown as formula (I), their synthesis and their use for treating a SHP2 mediated disorder. More particularly, provided are fused heterocyclic derivatives useful as inhibitors of SHP2, methods for producing such compounds and methods for treating a SHP2-mediated disorder.

Formula I

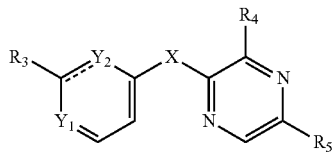

2 Claims, No Drawings

(56) References Cited

U.S. PATENT DOCUMENTS

| | | | |
|---|---|---|---|
| 8,258,156 | B2 | 9/2012 | Alper et al. |
| 8,313,729 | B2 | 11/2012 | Neumann et al. |
| 8,338,437 | B2 | 12/2012 | Wahhab et al. |
| 8,389,533 | B2 | 3/2013 | Connors et al. |
| 8,404,731 | B2 | 3/2013 | Mjalli et al. |
| 8,431,575 | B2 | 4/2013 | Gohimukkula et al. |
| 8,450,327 | B2 | 5/2013 | Gottschling et al. |
| 8,461,329 | B2 | 6/2013 | Takayama et al. |
| 8,575,168 | B2 | 11/2013 | Azimioara et al. |
| 8,637,500 | B2 | 1/2014 | Allen et al. |
| 8,759,377 | B2 | 6/2014 | Conn et al. |
| 8,791,136 | B2 | 7/2014 | Goff et al. |
| 8,809,370 | B2 | 8/2014 | Goff et al. |
| 8,822,497 | B2 | 9/2014 | Burger et al. |
| 8,889,730 | B2 | 11/2014 | Bhattacharya et al. |
| 8,912,219 | B2 | 12/2014 | Fauber et al. |
| 8,952,014 | B2 | 2/2015 | Gottschling et al. |
| 8,980,921 | B2 | 3/2015 | Goff et al. |
| 8,987,303 | B2 | 3/2015 | Goff et al. |
| 9,062,015 | B2 | 6/2015 | Stieber et al. |
| 9,266,856 | B2 | 2/2016 | Goff et al. |
| 9,624,199 | B2 | 4/2017 | Becker-Pelster et al. |
| 9,663,496 | B2 | 5/2017 | Irving et al. |
| 9,815,813 | B2 | 11/2017 | Chen et al. |
| 9,969,719 | B2 | 5/2018 | Ding et al. |
| 10,077,276 | B2 | 9/2018 | Chen et al. |
| 10,253,046 | B2 | 4/2019 | Dahlgren et al. |
| 10,287,266 | B2 | 5/2019 | Chen et al. |
| 10,301,278 | B2 | 5/2019 | Chen et al. |
| 10,329,270 | B2 | 6/2019 | Qiu et al. |
| 10,377,742 | B2 | 8/2019 | Goff et al. |
| 10,463,662 | B2 | 11/2019 | Lu |
| 2007/0037794 | A1 | 2/2007 | Ungashe et al. |
| 2007/0043057 | A1 | 2/2007 | Matteucci et al. |
| 2008/0269217 | A1 | 10/2008 | Vos et al. |
| 2008/0269251 | A1 | 10/2008 | Andre-Gil et al. |
| 2009/0023701 | A1 | 1/2009 | Aungst et al. |
| 2009/0111801 | A1 | 4/2009 | Andres-Gil et al. |
| 2009/0281099 | A1 | 11/2009 | Andrés-Gil et al. |
| 2009/0286831 | A1 | 11/2009 | Koegel et al. |
| 2010/0016319 | A1 | 1/2010 | Ohno et al. |
| 2010/0216816 | A1 | 8/2010 | Barrow et al. |
| 2011/0098269 | A1 | 4/2011 | Becknell et al. |
| 2011/0152246 | A1 | 6/2011 | Buckman et al. |
| 2012/0157471 | A1 | 6/2012 | Nair et al. |
| 2012/0184572 | A1 | 7/2012 | Song et al. |
| 2014/0005103 | A1 | 1/2014 | Coburn et al. |
| 2014/0142094 | A1 | 5/2014 | Reddy et al. |
| 2015/0087673 | A1 | 3/2015 | Hitoshi et al. |
| 2016/0159773 | A1 | 6/2016 | Saitoh et al. |
| 2018/0057478 | A1 | 3/2018 | Goff et al. |
| 2018/0207054 | A1 | 7/2018 | Sitsihovskiy et al. |
| 2019/0300533 | A1 | 10/2019 | Wang et al. |

FOREIGN PATENT DOCUMENTS

| | | |
|---|---|---|
| CN | 105899491 A | 8/2016 |
| CN | 105899493 A | 8/2016 |
| CN | 105916845 A | 8/2016 |
| CN | 106232581 A | 12/2016 |
| CN | 107286150 A | 10/2017 |
| EP | 3 290 412 A1 | 3/2018 |
| EP | 2 985 334 B1 | 6/2018 |
| EP | 2 883 934 B1 | 11/2019 |
| EP | 3 608 321 A1 | 2/2020 |
| JP | 2007-13804 A | 1/2007 |
| WO | WO 2002/032872 A1 | 4/2002 |
| WO | WO 2003/059354 A1 | 9/2003 |
| WO | WO 2003/072548 A1 | 9/2003 |
| WO | WO 2004/033406 A1 | 4/2004 |
| WO | WO 2004/046092 A2 | 6/2004 |
| WO | WO 2004/046092 A3 | 6/2004 |
| WO | WO 2004/071426 | 8/2004 |
| WO | WO 2004/074266 A1 | 9/2004 |
| WO | WO 2004/085409 A2 | 10/2004 |
| WO | WO 2004/085409 A3 | 10/2004 |
| WO | WO 2004/099158 A1 | 11/2004 |
| WO | WO 2005/004810 A2 | 1/2005 |
| WO | WO 2005/005435 A1 | 1/2005 |
| WO | WO 2005/033105 A2 | 4/2005 |
| WO | WO 2005/044797 A1 | 5/2005 |
| WO | WO 2005/066156 A1 | 7/2005 |
| WO | WO 2006/012226 A2 | 2/2006 |
| WO | WO 2006/045828 A1 | 5/2006 |
| WO | WO 2006/063010 A2 | 6/2006 |
| WO | WO 2006/067466 A2 | 6/2006 |
| WO | WO 2006/071759 A2 | 7/2006 |
| WO | WO 2006/084186 A2 | 8/2006 |
| WO | WO 2006/087305 A1 | 8/2006 |
| WO | WO 2007/045462 A2 | 4/2007 |
| WO | WO 2007/046867 A2 | 4/2007 |
| WO | WO 2007/057742 A2 | 5/2007 |
| WO | WO 2007/063868 A1 | 6/2007 |
| WO | WO 2007/084728 A2 | 7/2007 |
| WO | WO 2007/103308 A2 | 9/2007 |
| WO | WO 2008/008431 A2 | 1/2008 |
| WO | WO 2008/008431 A3 | 1/2008 |
| WO | WO 2008/033857 A2 | 3/2008 |
| WO | WO 2008/100412 A1 | 8/2008 |
| WO | WO 2008/112674 A1 | 9/2008 |
| WO | WO 2009/033084 A1 | 3/2009 |
| WO | WO 2009/036066 A1 | 3/2009 |
| WO | WO 2009/108766 A1 | 9/2009 |
| WO | WO 2010/008739 A2 | 1/2010 |
| WO | WO 2010/020675 A1 | 2/2010 |
| WO | WO 2010/036380 A1 | 4/2010 |
| WO | WO 2010/070022 A1 | 6/2010 |
| WO | WO 2010/074244 A1 | 7/2010 |
| WO | WO 2010/085700 A2 | 7/2010 |
| WO | WO 2010/085700 A3 | 7/2010 |
| WO | WO 2010/086613 A1 | 8/2010 |
| WO | WO 2010/103547 A2 | 9/2010 |
| WO | WO 2011/004162 A2 | 1/2011 |
| WO | WO 2011/004162 A3 | 1/2011 |
| WO | WO 2011/022440 A2 | 2/2011 |
| WO | WO 2011/072791 A1 | 6/2011 |
| WO | WO 2011/103091 A1 | 8/2011 |
| WO | WO 2011/130232 A1 | 10/2011 |
| WO | WO 2011/135276 A1 | 11/2011 |
| WO | WO 2011/146401 A1 | 11/2011 |
| WO | WO 2011/150156 A2 | 12/2011 |
| WO | WO 2012/016217 A1 | 2/2012 |
| WO | WO 2012/026495 A1 | 3/2012 |
| WO | WO 2012/041158 A1 | 4/2012 |
| WO | WO 2012/069852 A1 | 5/2012 |
| WO | WO 2012/080729 A4 | 6/2012 |
| WO | WO 2012/088438 A1 | 6/2012 |
| WO | WO 2012/158784 A2 | 11/2012 |
| WO | WO 2013/017461 A1 | 2/2013 |
| WO | WO 2013/039851 A1 | 3/2013 |
| WO | WO 2013/090454 A2 | 6/2013 |
| WO | WO 2013/090454 A3 | 6/2013 |
| WO | WO 2013/124040 A1 | 8/2013 |
| WO | WO 2013/139882 A1 | 9/2013 |
| WO | WO 2013/161308 A1 | 10/2013 |
| WO | WO 2013/167633 A1 | 11/2013 |
| WO | WO 2014/000178 A1 | 1/2014 |
| WO | WO 2014/001377 A1 | 1/2014 |
| WO | WO 2014/004416 A1 | 1/2014 |
| WO | WO 2014/028829 A1 | 2/2014 |
| WO | WO 2014/043068 A1 | 3/2014 |
| WO | WO 2014/140704 A1 | 9/2014 |
| WO | WO 2014/144326 A1 | 9/2014 |
| WO | WO 2014/184014 A1 | 11/2014 |
| WO | WO 2014/184074 A1 | 11/2014 |
| WO | WO 2014/191737 A1 | 12/2014 |
| WO | WO 2014/201172 A1 | 12/2014 |
| WO | WO 2015/003094 A2 | 1/2015 |
| WO | WO 2015/016206 A1 | 2/2015 |
| WO | WO 2015/017305 A1 | 2/2015 |
| WO | WO 2015/048547 A3 | 4/2015 |
| WO | WO 2015/091420 A1 | 6/2015 |
| WO | WO 2015/107493 A1 | 7/2015 |
| WO | WO 2015/107494 A1 | 7/2015 |

(56) References Cited

FOREIGN PATENT DOCUMENTS

| WO | WO 2015/107495 A1 | 7/2015 | |
| WO | WO-2015107495 A1 * | 7/2015 | ........... C07D 241/18 |
| WO | WO 2015/123437 A1 | 8/2015 | |
| WO | WO 2015/123533 A1 | 8/2015 | |
| WO | WO 2015/148714 A1 | 10/2015 | |
| WO | WO 2015/155042 A1 | 10/2015 | |
| WO | WO 2015/177325 A1 | 11/2015 | |
| WO | WO 2016/015604 A1 | 2/2016 | |
| WO | WO 2016/022644 A1 | 2/2016 | |
| WO | WO 2016/022645 A1 | 2/2016 | |
| WO | WO 2016/040449 A1 | 3/2016 | |
| WO | WO 2016/138352 A1 | 9/2016 | |
| WO | WO 2016/141881 A1 | 9/2016 | |
| WO | WO 2016/151501 A1 | 9/2016 | |
| WO | WO 2016/195776 A1 | 12/2016 | |
| WO | WO 2016/197027 A1 | 12/2016 | |
| WO | WO 2016/203404 A1 | 12/2016 | |
| WO | WO 2016/203405 A1 | 12/2016 | |
| WO | WO 2016/203406 A1 | 12/2016 | |
| WO | WO 2017/021784 A2 | 2/2017 | |
| WO | WO 2017/049321 A1 | 3/2017 | |
| WO | WO 2017/114351 A1 | 7/2017 | |
| WO | WO 2017/156397 A1 | 9/2017 | |
| WO | WO 2017/210134 A1 | 12/2017 | |
| WO | WO 2017/211303 A1 | 12/2017 | |
| WO | WO 2017/216706 A1 | 12/2017 | |
| WO | WO 2018/013597 A1 | 1/2018 | |
| WO | WO 2018/057884 A1 | 3/2018 | |
| WO | WO 2018/089433 A1 | 5/2018 | |
| WO | WO 2018/127801 A1 | 7/2018 | |
| WO | WO-2018172984 A1 * | 9/2018 | ......... C07D 491/113 |
| WO | WO 2018/177403 A1 | 10/2018 | |
| WO | WO 2019/014427 A1 | 1/2019 | |
| WO | WO 2019/075265 A1 | 4/2019 | |
| WO | WO 2019/079783 A1 | 4/2019 | |
| WO | WO 2019/126696 A1 | 6/2019 | |
| WO | WO 2019/148132 A1 | 8/2019 | |
| WO | WO 2019/148136 A1 | 8/2019 | |
| WO | WO 2019/152454 A1 | 8/2019 | |
| WO | WO 2019/154950 A1 | 8/2019 | |
| WO | WO 2019/167000 A1 | 9/2019 | |
| WO | WO 2019/182924 A1 | 9/2019 | |

OTHER PUBLICATIONS

Written Opinion of the International Search Authority for International Application No. PCT/CN2017/087471. (8 pages).
Ahronian, Leanne G., "Strategies for Monitoring and Combating Resistance to Combination Kinase Inhibitors for Cancer Therapy," Ahronian and Corcoran Genome Medicine (2017) 9:37; DOI: 10.1186/s13073-017-0431-3 (12 pages).
Bentires-Alj, Mohamed et al., "Activating Mutations of the Noonan Syndrome-Associated SHP2/PTPN11 Gene in Human Solid Tumors and Adult Acute Myelogenous Leukemia," Cancer Research 64, 8816-8820, Dec. 15, 2004.
Bunda, Severa et al., "Inhibition of SHP2-Mediated Dephosphorylation of Ras Suppresses Oncogenesis," Nature Communications, 6:8859 (2015), DOI: 10.1038/ncomms9859/www.nature.com/naturecommunications (12 pages).
Butterworth, Sam et al., "Targeting Protein Tyrosine Phosphatase SHP2 for Therapeutic Intervention," Future Med. Chem. 6(12), 1423-1437 (2014).
Chen, Chuan et al., "Discovery of a Novel Inhibitor of the Protein Tyrosine Phosphatase Shp2," Scientific Reports 5:17626, DOI: 10:1038/srep 17626 (2015) (13 pages).
Chen, Liwei et al., "Discovery of a Novel Shp2 Protein Tyrosine Phosphatase Inhibitor," Molecular Pharmacology, vol. 70, No. 2 562-570 (2006).
Chen, Wendy S. et al., "Treating Leukemia at the Risk of Inducing Severe Anemia," Exp Henatol. 2016, 44(5): 329-331: doi:10.1016/j.exphem.2016.01.004.

Chen, Ying-Nan P., et al., "Allosteric Inhibition of SHP2 Phosphatase Inhibits Cancers Driven by Receptor Tyrosine Kinases," Nature 535, 148-152 (2016).
Chichger, Havovi et al., "SH2-Domain-Containing Protein Tyrosine Phosphatase 2 and Focal Adhesion Kinase Protein Interactions Regulate Pulmonary Endothelium Barrier Function," Am. J. Respir. Cell Biol. vol. 52, Iss 6, 595-707, Jun. 2015.
Chio, Cynthia M. et al., "Targeting a Cryptic Allosteric Site for Selective Inhibition of the Oncogenic Protein Tyrosine Phosphatase Shp2," Biochemistry 54, 497-504 (2015).
Dardaei, Leila et al., "SHP2 Inhibition Restores Sensitivity in ALK-rearranged non-small-cell Lung Cancer Resistant to ALK Inhibitors," Nature Medicine, 24, 512-517 (2018).
Dong, Lei et al., "Leukaemogenic Effects of Ptpn11 Activating Mutations in the Stem Cell Microenvironment," Nature, 539, 304-308 (2016).
Fodor, Michelle et al., "Dual Allosteric Inhibition of SHP2 Phosphatase," ACS Chem. Biol. 2018, 13, 3, 647-656.
Fortanet, Jorge Garcia et al., "Allosteric Inhibition of SHP2: Identification of a Potent, Selective, and Orally Efficacious Phosphatase Inhibitor," Journal of Medical Chemistry, 2016, 59, 17, 7773-7782.
Frankson, Rochelle et al., "Therapeutic Targeting of Oncogenic Tyrosine Phosphatases," Cancer Res, Nov. 1, 2017, (77) (21) 5701-5705.
Grosskopf, Stefanie et al., "Selective Inhibitors of the Protein Tyrosine Phosphatase SHP2 Block Cellular Motility and Growth of Cancer Cells In Vitro and In Vivo," ChemMedChem 2015, 10, 815-826.
Guo, Wenjie et al., "Tyrosine Phosphatase SHP2 Negatively Regulates NLRP3 Inflammasome Activation via ANTI-dependent Mitochondrial Homeostasis," Nature Communications, 8:2168 (2017); (14 pages).
He, Rongjun et al., "Exploring the Existing Drug Space for Novel pTyr Mimetic and SHP2 Inhibitors," ACS Med. Chem. Lett. 2015, 6, 7, 782-786.
Hellmuth, Klaus et al., "Specific Inhibitors of the Protein Tyrosine Phosphatase Shp2 Identified by High-Throughput Docking," PNAS, May 20, 2008, vol. 105, No. 20, 7275-7280.
Huang, Wen-Qing et al., "Structure, Function, and Pathogensis of SHP2 in Developmental Disorders and Tumorigenesis," Current Cancer Drug Targets, 2014, 14, 567-588.
Lappalainen, Ilkka et al., "Genome Wide Analysis of Pathogenic SH2 Domain Mutations," Proteins 2008; 72:779-792.
LaRochelle, J.R. et al., "Identification of an Allosteric Benzothiazolopyrimidone Inhibitor of the Oncogenic Protein Tyrosine Phosphatase SHP2," Biooganic & Medicinal Chemistry, vol. 25, Issue 24, Dec. 15, 2017, pp. 6479-6485.
LaRochelle, Jonathan R., "Structural and Functional Consequences of Three Cancer-Associated Mutations of the Oncogenic Phosphatase SHP2," Biochemistry 55, 2269-2277 (2016).
Lawrence, Harshani R. et al., "Inhibitors of Src Homology-2 Domain Containing Protein Tyrosine Phosphatase-2 (Shp2) Based on Oxindole Scaffolds," J. Med. Chem 2008: 51(16): 4948-4956.
Leibowitz, Michael S. et al., "SHP2 is Overexpressed and Inhibits pSTAT1-Mediated APM Component Expression, T Cell Attracting Chemokine Secretion, and CTL Recognition in Head and Neck Cancer Cells," Clin Cancer Res. 19(4): 798-808, 2013.
Li, Jing et al., "PD-1/SHP-2 Inhibits Tc1/Th1 Phenotypic Responses and the Activation of T Cells in the Tumor Microenvironment," Cancer Research, Feb. 1, 2015 (75) (3) 508-518.
Liu, Kun-Wei et al., "SHP-2/PTPN11 Mediates Gliomagenesis Driven by PDGFRA and INK4A/ARF Aberrations in Mice and Humans," The Journal of Clinical Investigation, vol. 121, No. 3, Mar. 2011; pp. 905-917.
Liu, Wei et al., "Identification of Cryptotanshinone as an Inhibitor of Oncogenic Protein Tyrosine Phosphatase SHP2 (PTPN11)," J. Med. Chem. 2013; 56(18): 7212-7221.
Liu, Wen et al., "T Lymphocyte SHP2-deficiency Triggers Anti-Tumor Immunity to Inhibit Colitis-Associated Cancer in Mice," Oncotarget, Advance Publications 2016; (12 pages).
Liu, Wen et al., "T Lymphocyte SHP2-deficiency Triggers Anti-Tumor Immunity to Inhibit Colitis-Associated Cancer in Mice," Oncotarget, 2017, vol. 8, (No. 5), pp. 7586-7597.

(56) References Cited

OTHER PUBLICATIONS

Manguso, Robert T. et al., "In vivo CRISPR Screening Identifies Ptpn2 as a Cancer Immunotherapy Target," Nature 2017, 547(7664):413-418.
Martin, Katie R. et al., "Integrating Virtual and Biochemical Screening for Protein Tyrosine Phosphatase Inhibitor Discovery," Methods, 65 (2014) 219-228.
Matozaki, Takashi et al., "Protein Tyrosine Phosphatase SHP-2: A Protooncogene Product that Promotes Ras Activation," Cancer Science, Oct. 2009, vol. 100, No. 10, 1786-1793.
Mazharian, Alexandra et al., "Megakaryocyte-specific Deletion of the Protein-Tyrosine Phosphatases Shp1 and Shp2 Causes Abnormal Megakaryocyte Development, Platelet Production, and Function," Blood. May 16, 2013;121(20):4205-4220.
Mohi, M. Golam et al., "The Role of Shp2 (PTPN11) in cancer," Genetics & Development 2007, 17:23-30.
Nichols, Robert J. et al., "Efficacy of SHP2 Phosphatase Inhibition in Cancers With Nucleotide-Cycling Oncogenic RAS, RAS-GTP Dependent Oncogenic BRAF and NF1 Loss," BioRxiv Sep. 14, 2017 (16 pages).
Pandey, Ruchi et al., "Role of SHP2 in Hematopoiesis and Leukemogenesis," Curr Opin Hematol. Jul. 2017 4(4):307-313.
Peled, Michael et al., "Affinity Purification Mass Spectrometry Analysis of PD-1 Uncovers SAP as a New Checkpoint Inhibitor," Proc Natl Acad Sci USA. Jan. 16, 2018;115(3):pp. E468-E477.
Prahallad, Anirudh et al., "PTPN11 Is a Central Node in Intrinsic and Acquired Resistance to Targeted Cancer Drugs," Cell Reports, 12, 1978-1985, Sep. 29, 2015.
Protein Tyrosine Phosphatase, PTPN11 (SHP-2) (Human), Dec. 2005 (1 page).
Qi, Chen et al., "Shp2 Inhibits Proliferation of Esophageal Squamous Cell Cancer via Dephosphorylation of Stat3," International Journal of Molecular Sciences, 18, 134 (2017) (12 pages).
Ran, Hao et al., "Sticking It to Cancer with Molecular Glue for SHP2," Cancer Cell 30, Aug. 8, 2016; 8;30(2):194-196.
Scott, Latanya M. et al., "Shp2 Protein Tyrosine Phosphatase Inhibitor Activity of Estramustine Phosphate and its Triterpenoid Analogs," Bioorg Med Chem Lett., 21(2), 730-733 Jan. 15, 2011.
Simoncic, Paul D., "T-Cell Protein Tyrosine Phosphatase (Tcptp) Is a Negative Regulator of Colony-Stimulating Factor 1 Signaling and Macrophage Differentiation," Molecular and Cellular Biology, vol. 26, No. 11, Jun. 2006, p. 4149-4160.
Stephan, Matthias T. et al., "Synapse-directed Delivery of Immunomodulators Using T-Cell-Conjugated Nanoparticles," Biomaterials 33, 5776-5787 (2012).
Sun, X. et al., "Selective Inhibition of Leukemia-Associated SHP2$^{E69K}$ Mutant by the Allosteric SHP2 Inhibitor SHP099," Leukemia, 32, pp. 1246-1249 (2018).
Supplementary European Search Report for corresponding EP Application No. EP 17 80 9742 dated Mar. 15, 2019 (2 pages).
Wang, Wen-Long et al., "Benzo[c][1,2,5]thiadiazole Derivatives: A New Class of Potent Src Homology-2-domain Containing Protein Tyrosine Phosphatase-2 (SHP2) Inhibitors," Bioorganic & Medicinal Chemistry Letters Dec. 1, 2017;27(23): pp. 5154-5157.
Xie, Jingjing et al., "Allosteric Inhibitors of SHP2 with Therapeutic Potential for Cancer Treatment," Journal of Medicinal Chemistry, Nov. 20, 2017; 60, 24, pp. 10205-10219.
Xu, Jie et al., "Targeting SHP2 for EGFR Inhibitor Resistant Non-Small Cell Lung Carcinoma," Biochem Biophys Res Commun., 439(4), Oct. 4, 2013;439(4): pp. 586-590.
Yokosuka, Tadashi et al., "Programmed Cell Death 1 Forms Negative Costimulatory Microclusters that Directly Inhibit T Cell Receptor Signaling by Recruiting Phosphatase SHP2," J. Exp. Med., vol. 209, No. 6, 1201-1217 (2012).
Yu, Bing et al., "Targeting Protein Tyrosine Phosphatase SHP2 for the Treatment of PTPN11-Associated Malignancies," Mol Cancer Ther; 12(9) Sep. 2013 pp. 1738-1748.
Zeng, Li-Fan et al., "Therapeutic Potential of Targeting the Oncogenic SHP2 Phosphatase," J. Med Chem. 2014, 57, 6594-6609.
Zhang, Jie et al., "Functions of Shp2 in Cancer," J. Cell. Mol. Med. vol. 19, No. 9, pp. 2075-2083 (2015).
Zheng, Jian et al., "Pancreatic Cancer Risk Variant in LINC00673 Creates a miR-1231 Binding Site and Interferes with PTPN11 Degradation," Nature Genetics, vol. 48, No. 7, Jul. 2016; pp. 747-757.
Zhu, Helen He et al.,"Shp2 and Pten Have Antagonistic roles in Myeloproliferation but Cooperate to Promote Erythropoiesis in Mammals," PNAS, vol. 12, No. 43, 13342-13347, 2015.

* cited by examiner

HETEROCYCLIC RING DERIVATIVES USEFUL AS SHP2 INHIBITORS

This application is a national stage filing under 35 U.S.C. § 371 of International Application No. PCT/CN2017/087471, filed Jun. 7, 2017, which claims priority to PCT/CN2016/085122, filed Jun. 7, 2016. The contents of these applications are each incorporated herein by reference.

TECHNICAL FIELD

This invention relates to certain novel pyrazine derivatives (Formula I) as SHP2 inhibitors which is shown as formula I, their synthesis and their use for treating a SHP2 mediated disorder. More particularly, this invention is directed to fused heterocyclic derivatives useful as inhibitors of SHP2, methods for producing such compounds and methods for treating a SHP2-mediated disorder.

BACKGROUND ART

SHP2 (The Src Homolgy-2 phosphatease) is a non-receptor protein tyrosine phosphatase encoded by the PTPN11 gene that harbors a classical tyrosine phosphatase domain and two N-terminal Src homology 2 (SH2) domains and a C-terminal tail. The two SH2 domains control the subcellular localization and functional regulation of SHP2. In its inactive state, the N-terminal SH2 domain blocks the PTP domain and this autoinhibition is relieved by binding of the SH2 domains to specific phosphotyrosine sites on receptors or receptor-associated adaptor proteins. The stimulation, for example, by cytokines or growth factors leads to exposure of the catalytic site resulting in enzymatic activation of SHP2.

SHP2 is widely expressed and participated in multiple cell signaling processes, such as the Ras-Erk, PI3K-Akt, Jak-Stat, Met, FGFR, EGFR, and insulin receptors and NF-kB pathways, in which plays an important role in proliferation, differentiation, cell cycle maintenance and migration.

The hyperactivation of SHP2 catalytic activity caused by either germline or somatic mutations in PTPN11 has been identified in patients with Noonan syndrome, Leopard syndrome, juvenile myelomonocytic leukemias, myelodysplastic syndrome, B cell acute lymphoblastic leukemia/lymphoma, and acute myeloid leukemia. In addition, activating mutations of PTPN11 have been found in solid tumors as well, such as lung cancer, colon cancer, melanoma, neuroblastoma, and hepatocellular carcinoma. Therefore, the presence of the activated or up-regulated SHP2 protein in human cancers and other disease make SHP2 an excellent target for development of novel therapies. The compounds of the present invention fulfill the need of small molecules in order to inhibit the activity of SHP2.

SUMMARY OF INVENTION

The present invention relates to heterocyclic pyrazine compounds useful as SHP2 inhibitors and for the treatment of conditions mediated by SHP2. The compounds of the invention have the general structure as Formula I or a pharmaceutically acceptable salt:

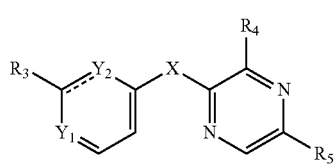

Formula I and

X is absent, O, S, SO, $S(O)_2$, C(O), $C(O)R_{11}$, $CR_{11}R_{12}$, or $-NR_{11}$; and each $R_{11}$ and $R_{12}$ is independently $-H$, halogen, $-NH_2$, $-CN$, $-OH$, $-NO_2$, carbonyl, $=O$, oxo, carboxyl, substituted or unsubstituted $C_{1-6}$alkoxy, or substituted or unsubstituted $C_{1-6}$alkyl;

$Y_1$ is N or $CR_1$;

$Y_2$ is N or $CR_2$;

each $R_1$ and $R_2$ is independently $-H$, halogen, $-CN$, $-OH$, $-NH_2$, $-N_3$, $-NO_2$, substituted or unsubstituted $C_{1-6}$alkoxy, or substituted or unsubstituted $C_{1-6}$alkyl; or $R_1$ combines with $R_3$, or $R_2$ combines with $R_3$, to form a 5-10 member heteroaryl, 5-10 member carbocyclic or 5-10 member heterocyclic ring, wherein each of the ring systems is independently optionally substituted with halogen, $-CN$, $-OH$, $-NR_8R_9$, $-N_3$, $-NO_2$, carbonyl, $=O$, oxo, substituted or unsubstituted $C_{1-6}$alkyl, substituted or unsubstituted $C_{1-6}$alkoxy, or $C(O)R_8$; or $R_3$ is $-H$, halogen, $-CN$, $-OH$, $-N_3$, $-NO_2$, $-NR_8R_9$, $-N(R_8)(CH_2)_pNR_8R_9$, $-N(R_8)(CH_2)_pR_8$, $-N(R_8)G_pR_8$, $-N(R_8)G_pNR_8R_9$, $-N(R_8)(C=O)_qR_8$, $-N(R_8)(C=O)_qNR_8R_9$, $-N(R_8)(C=O)_qG_pR_8$, $-N(R_8)(C=O)_qG_pNR_8R_9$, $-N(R_8)(C=O)_qG_p(C=O)_qNR_8R_9$, $-N(R_8)(C=O)_qN(R_8)(C=O)_qR_8$, $-N(R_8)(C=O)_qN(R_8)(C=O)_qNR_8R_9$, $-N(R_8)(C=O)_qN(R_8)G_q(C=O)_pR_8$, $-N(R_8)(C=O)_qN(R_8)G_p(C=O)_qNR_8R_9$, $C(O)_qR_8$, $C(O)OR_8$, $C(O)NH_2$, $C(O)NHR_8$, $C(O)NR_8R_9$, $C_{1-6}$alkyl, $C_{6-10}$aryl, arylalkyl, alkoxy, heteroaryl, heterocyclic, or carbocyclic; and each of which may be optionally substituted; and each p and q is independently 0, 1, 2 or 3;

each G is independently $C_{6-10}$ary, $C_{3-8}$carbocyclic or $C_{5-10}$heteroaryl; and each of which may be optionally substituted;

$R_4$ is $-H$, halogen, $-CN$, $-OH$, $-NR_8R_9$, $-N_3$, $-NO_2$, substituted or unsubstituted $C_{1-6}$alkoxy, substituted or unsubstituted $C_{1-6}$alkyl, $C_{5-18}$heterocyclic or $C_{5-18}$carbocyclic; wherein each of the ring systems is independently optionally substituted with halogen, $-CN$, $-OH$, $-NO_2$, carbonyl, $=O$, oxo, substituted or unsubstituted $C_{1-6}$alkyl, substituted or unsubstituted $C_{1-6}$alkoxy, $-NR_8R_9$, or $-CH_2NR_8R_9$;

$R_5$ is $-H$, halogen, $-CN$, $-OH$, $-NR_8R_9$, $-N_3$, $-NO_2$, $C_{1-6}$alkyl, $C_{1-6}$alkoxy, $C_{6-10}$aryl, $C_{6-10}$arylalkyl, $C_{6-10}$heteroaryl, $C_{5-18}$heterocyclic or $C_{5-18}$carbocyclic; and each of which is independently optionally substituted;

each $R_8$ and $R_9$ is independently $-H$, halogen, $-CN$, $-OH$, $-N_3$, $-NO_2$, $C_{1-6}$alkyl, $C_{1-6}$alkoxy, $C_{2-6}$alkenyl, $NH(C_{1-6}$alkyl$)$, $N(C_{1-6}$alkyl$)_2$, $C_{5-10}$heterocyclic or $C_{5-10}$carbocyclic; and each of which may be independently optionally substituted.

The present invention further provides some preferred technical solutions with regard to compound of Formula (I).

In some embodiments of Formula (I), $R_1$ is $-H$, $-F$, $-Cl$, $-Br$, $-I$, $-CN$, $-OH$, $-NH_2$, substituted or unsubstituted $C_{1-3}$alkoxy, or substituted or unsubstituted $C_{1-3}$alkyl.

In some embodiments of Formula (I), $R_1$ is $-H$, $-F$, $-Cl$, $-NH_2$, methyl, ethyl, propyl, isopropyl, methoxy, ethoxy, propoxy or isopropoxy; and each methyl, ethyl, propyl, isopropyl, methoxy, ethoxy, propoxy or isopropoxy is independently optionally substituted with halogen, OH or $NH_2$.

In some embodiments of Formula (I), $R_2$ is $-H$, $-F$, $-Cl$, $-Br$, $-I$, $-CN$, $-OH$, $-NH_2$, substituted or unsubstituted $C_{1-3}$alkoxy, or substituted or unsubstituted $C_{1-3}$alkyl.

In some embodiments of Formula (I), $R_2$ is —H, —F, —Cl, —NH$_2$, methyl, ethyl, propyl, isopropyl, methoxy, ethoxy, propoxy or isopropoxy; and each methyl, ethyl, propyl, isopropyl, methoxy, ethoxy, propoxy or isopropoxy is independently optionally substituted with halogen, OH or NH$_2$.

In some embodiments of Formula (I), $R_3$ is —H, —F, —Cl, —Br, —CN, —OH, —NO$_2$, —NR$_8$R$_9$, —N(R$_8$)(CH$_2$)$_p$NR$_8$R$_9$, —N(R$_8$)(CH$_2$)$_p$R$_8$, —N(R$_8$)G$_p$R$_8$, —N(R$_8$)G$_p$NR$_8$R$_9$, —N(R$_8$)(C=O)$_q$R$_8$, —N(R$_8$)(C=O)$_q$NR$_8$R$_9$, —N(R$_8$)(C=O)$_q$G$_p$R$_8$, —N(R$_8$)(C=O)$_q$G$_p$NR$_8$R$_9$, —N(R$_8$)(C=O)$_q$G$_p$(C=O)$_q$R$_8$, —N(R$_8$)(C=O)$_q$G$_p$(C=O)$_q$NR$_8$R$_9$, —N(R$_8$)(C=O)$_q$N(R$_8$)(C=O)$_q$R$_8$, —N(R$_8$)(C=O)$_q$N(R$_8$)(C=O)$_q$NR$_8$R$_9$, —N(R$_8$)(C=O)$_q$N(R$_8$)G$_q$(C=O)$_p$R$_8$, —N(R$_8$)(C=O)$_q$N(R$_8$)G$_p$(C=O)$_q$NR$_8$R$_9$, C(O)$_q$R$_8$, C(O)OR$_8$, C(O)NH$_2$, C(O)NHR$_8$, C(O)NR$_8$R$_9$, C$_{1-6}$alkyl or C$_{6-10}$aryl; and each of which may be optionally substituted with halogen, —CN, —OH, —NH$_2$, —N$_3$, —NO$_2$, substituted or unsubstituted C$_{1-6}$alkyl, or substituted or unsubstituted C$_{1-6}$alkoxy.

In some embodiments of Formula (I), $R_3$ is —H, —F, —Cl, —Br, —NR$_8$R$_9$, —N(R$_8$)(CH$_2$)NR$_8$R$_9$, —N(R$_8$)(CH$_2$)$_p$R$_8$, —N(R$_8$)G$_p$R$_8$, —N(R$_8$)G$_p$NR$_8$R$_9$, —N(R$_8$)(C=O)$_q$R$_8$, —N(R$_8$)(C=O)$_q$NR$_8$R$_9$, —N(R$_8$)(C=O)$_q$G$_p$R$_8$, —N(R$_8$)(C=O)$_q$G$_p$NR$_8$R$_9$, —N(R$_8$)(C=O)$_q$G$_p$(C=O)$_q$R$_8$, —N(R$_8$)(C=O)$_q$G$_p$(C=O)$_q$NR$_8$R$_9$, —N(R$_8$)(C=O)$_q$N(R$_8$)(C=O)$_q$R$_8$, —N(R$_8$)(C=O)$_q$N(R$_8$)(C=O)$_q$NR$_8$R$_9$, —N(R$_8$)(C=O)$_q$N(R$_8$)G$_q$(C=O)$_p$R$_8$, —N(R$_8$)(C=O)$_q$N(R$_8$)G$_p$(C=O)$_q$NR$_8$R$_9$ or C(O)$_q$R$_8$, and each of which may be optionally substituted with —F, —Cl, —Br, —NHmethyl, —NHethyl, —NHpropyl, —NHisopropyl, —NHOCH$_3$, —NHOCH$_2$CH$_3$, —NHCH$_2$OCH$_3$, —NHOCH$_2$CH$_2$CH$_3$, —NHCH$_2$OCH$_2$CH$_3$, —NHCH$_2$CH$_2$OCH$_3$, —NHOCH(CH$_3$)$_2$, —NHCH(OCH$_3$)$_2$, methyl, ethyl, propyl, isopropyl, methoxy, ethoxy, propoxy or isopropoxy; and each methyl, ethyl, propyl, isopropyl, methoxy, ethoxy, propoxy or isopropoxy is independently optionally substituted with —F, —Cl, —Br or —I.

In some embodiments of Formula (I), each G is independently 6-membered aryl, 7-membered aryl, 8-membered aryl, 3-membered carbocyclic, 4-membered carbocyclic, 5-membered carbocyclic, 6-membered carbocyclic or 7-membered carbocyclic; and each of which may be optionally substituted with halogen, —CN, —OH, —NH$_2$, —N$_3$, —NO$_2$, substituted or unsubstituted C$_{1-6}$alkyl, or substituted or unsubstituted C$_{1-6}$alkoxy.

In some embodiments of Formula (I), each G is independently 6-membered aryl, 7-membered aryl, 8-membered aryl, 3-membered carbocyclic, 4-membered carbocyclic, 5-membered carbocyclic or 6-membered carbocyclic; and each of which may be optionally substituted with —F, —Cl, —Br, —CN, —OH, —NH$_2$, —NO$_2$, substituted or unsubstituted C$_{1-3}$alkyl, or substituted or unsubstituted C$_{1-3}$alkoxy.

In some embodiments of Formula (I), each G is independently phenyl, and which may be optionally substituted with —F, —Cl, —OH, —NH$_2$, methyl, ethyl, propyl, isopropyl, methoxy, ethoxy, propoxy or isopropoxy; and each methyl, ethyl, propyl, isopropyl, methoxy, ethoxy, propoxy or isopropoxy is independently optionally substituted with —F, —Cl, —Br or —I.

In some embodiments of Formula (I), each G is independently 5-membered heteroaryl, 6-membered heteroaryl, 7-membered heteroaryl or 8-membered heteroaryl; and each of which contains 1, 2, 3 or 4 heteroatoms select from N, O or S, and may be optionally substituted with halogen, —CN, —OH, —NH$_2$, —N$_3$, —NO$_2$, substituted or unsubstituted C$_{1-6}$alkyl, or substituted or unsubstituted C$_{1-6}$alkoxy.

In some embodiments of Formula (I), p is 0 or 1.
In some embodiments of Formula (I), q is 1 or 2.
In some embodiments of Formula (I), $R_3$ is —NH$_2$,

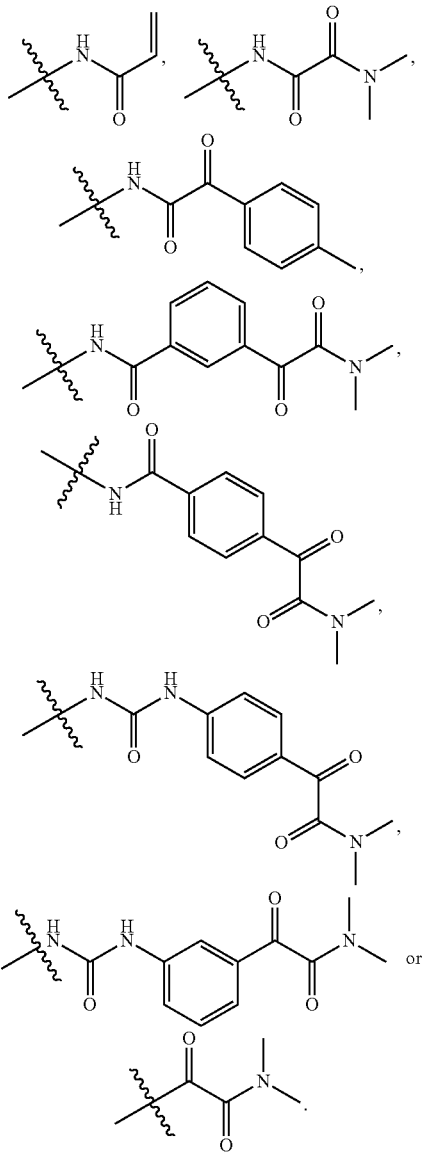

In some embodiments of Formula (I), $R_1$ is combines with $R_3$, or $R_2$ is combines with $R_3$, to form a 5-10 member heteroaryl or 5-10 member heterocyclic ring, wherein each of the ring systems is optionally substituted with halogen, —CN, —OH, —NH$_2$, carbonyl, =O, oxo, substituted or unsubstituted C$_{1-6}$alkyl, substituted or unsubstituted C$_{1-6}$alkoxy, or C(O)R$_8$.

In some embodiments of Formula (I), $R_1$ is combines with $R_3$, or $R_2$ is combines with $R_3$, to form a 5-membered heteroaryl, 6-membered heteroaryl, 7-membered heteroaryl, 8-membered heteroaryl, 5-membered heterocyclic ring, 6-membered heterocyclic ring, 7-membered heterocyclic ring or 8-membered heterocyclic ring; wherein each of the ring systems contains 1, 2, 3 or 4 heteroatoms select from N, O or S, and is optionally substituted with —F, —Cl, —Br, —I, —CN, —OH, —NH$_2$, carbonyl, =O, oxo, substituted or unsubstituted C$_{1-3}$alkyl, substituted or unsubstituted C$_{1-3}$alkoxy, or C(O)R$_8$.

In some embodiments of Formula (I), R$_1$ is combines with R$_3$ to form a 5-10 member heteroaryl or a 5-10 member heterocyclic ring; wherein each of the ring systems is optionally substituted with halogen, —CN, —OH, —NH$_2$, carbonyl, =O, oxo, substituted or unsubstituted C$_{1-6}$alkyl, substituted or unsubstituted C$_{1-6}$alkoxy, or C(O)R$_8$.

In some embodiments of Formula (I), R$_1$ is combines with R$_3$ to form a 5-membered heteroaryl, 6-membered heteroaryl, 7-membered heteroaryl, 8-membered heteroaryl, 5-membered heterocyclic ring, 6-membered heterocyclic ring, 7-membered heterocyclic ring or 8-membered heterocyclic ring, wherein each of the ring systems contains 1, 2, 3 or 4 heteroatoms select from N, O or S, and is optionally substituted with —F, —Cl, —Br, —I, —CN, —OH, —NH$_2$, carbonyl, =O, oxo, substituted or unsubstituted C$_{1-3}$alkyl, substituted or unsubstituted C$_{1-3}$alkoxy, or C(O)R$_8$.

In some embodiments of Formula (I), R$_1$ is combines with R$_3$ to form a 5-membered heteroaryl, 6-membered heteroaryl, 5-membered heterocyclic ring or 6-membered heterocyclic, wherein each of the ring systems contains 1, 2 or 3 heteroatoms select from N, O or S, and is optionally substituted with —F, —Cl, —Br, —I, —CN, —OH, —NH$_2$, —NHmethyl, —NHethyl, —NHpropyl, —NHisopropyl, —NHOCH$_3$, carbonyl, =O, oxo, methyl, ethyl, propyl, isopropyl, methoxy, CHF$_2$, CH$_2$F, CF$_3$ or C(O)R$_8$; and each methyl, ethyl, propyl, isopropyl, methoxy, CHF$_2$, CH$_2$F or C(O)R$_8$ is independently optionally substituted with —F, —Cl, —Br or —I.

In some embodiments of Formula (I), R$_2$ is combines with R$_3$ to form a 5-10 member heteroaryl or 5-10 member heterocyclic ring, wherein each of the ring systems is optionally substituted with halogen, —CN, —OH, —NH$_2$, carbonyl, =O, oxo, substituted or unsubstituted C$_{1-6}$alkyl, substituted or unsubstituted C$_{1-6}$alkoxy or C(O)R$_8$.

In some embodiments of Formula (I), R$_2$ is combines with R$_3$ to form a 5-membered heteroaryl, 6-membered heteroaryl, 7-membered heteroaryl, 8-membered heteroaryl, 5-membered heterocyclic ring, 6-membered heterocyclic ring, 7-membered heterocyclic ring or 8-membered heterocyclic ring, wherein each of the ring systems contains 1, 2, 3 or 4 heteroatoms select from N, O or S, and is optionally substituted with —F, —Cl, —Br, —I, —CN, —OH, —NH$_2$, carbonyl, =O, oxo, substituted or unsubstituted C$_{1-3}$alkyl, substituted or unsubstituted C$_{1-3}$alkoxy, or C(O)R$_8$.

In some embodiments of Formula (I), R$_4$ is —H, —F, —Cl, —Br, —CN, —OH, —NR$_8$R$_9$, substituted or unsubstituted C$_{1-6}$alkyl, substituted or unsubstituted C$_{1-6}$alkoxy, C$_{5-18}$heterocyclic or C$_{5-10}$carbocyclic, wherein each of the ring systems is optionally substituted with —F, —Cl, —Br, —CN, —OH, —NO$_2$, carbonyl, =O, oxo, substituted or unsubstituted C$_{1-6}$alkyl, —NH—C$_{1-6}$alkyl, —NH—C$_{1-6}$alkoxy, —C$_{1-6}$alkylene-NH$_2$, or —C$_{1-6}$alkylene-NH—C$_{1-6}$alkyl.

In some embodiments of Formula (I), R$_4$ is H, —F, —Cl, —CN, —OH, —NH$_2$, substituted or unsubstituted C$_{1-3}$alkyl, substituted or unsubstituted C$_{1-3}$alkoxy, 5-membered heterocyclic containing 1, 2 or 3 heteroatoms select from N or O, 6-membered heterocyclic containing 1, 2 or 3 heteroatoms select from N or O, 5-membered carbocyclic or 6-membered carbocyclic; wherein each of the ring systems is optionally substituted with —F, —Cl, —Br, —CN, —OH, carbonyl, =O, oxo, substituted or unsubstituted C$_{1-3}$alkyl, substituted or unsubstituted C$_{1-3}$alkoxy, —NH$_2$, —NH—C$_{1-3}$ alkyl, —NH—C$_{1-3}$alkoxy, —C$_{1-3}$alkylene-NH$_2$ or —C$_{1-3}$ alkylene-NH—C$_{1-3}$alkyl.

In some embodiments of Formula (I), R$_4$ is —Cl, —NH$_2$, methyl or piperidinyl, wherein the ring system is optionally substituted with methyl, —NH$_2$ or —CH$_2$NH$_2$.

In some embodiments of Formula (I), R$_5$ is —H, —F, —Cl, —Br, —I, —NR$_8$R$_9$, C$_{1-3}$alkyl, C$_{1-3}$alkoxy, C$_{6-9}$aryl, C$_{6-9}$arylalkyl, C$_{6-9}$heteroaryl, C$_{6-17}$heterocyclic or C$_{6-17}$carbocyclic, wherein each of which is independently optionally substituted with halogen, —CN, —OH, —N$_3$, —NO$_2$, —NH$_2$, carbonyl, =O, oxosubstituted or unsubstituted C$_{1-6}$alkyl, substituted or unsubstituted C$_{1-6}$alkoxy, substituted or unsubstituted (CH$_2$)$_k$NR$_8$R$_9$, substituted or unsubstituted (CH$_2$)$_k$NHC(O)OR$_8$ or C(O)R$_8$; and k is 0, 1 or 2.

In some embodiments of Formula (I), the C$_{6-9}$heteroaryl contains 1, 2, 3 or 4 heteroatoms select from N, O or S, and the C$_{6-9}$heteroaryl is 6-membered heteroaryl, 7-membered heteroaryl, 8-membered heteroaryl or 9-membered heteroaryl; the C$_{6-17}$heterocyclic contains 1, 2, 3, 4, 5, or 6 heteroatoms select from N, O, or S, and the C$_{6-17}$heterocyclic is 6-membered heterocyclic, 7-membered heterocyclic, 8-membered heterocyclic, 9-membered heterocyclic, 10-membered heterocyclic, 11-membered heterocyclic, 12-membered heterocyclic, 13-membered heterocyclic, 14-membered heterocyclic, 15-membered heterocyclic, 16-membered heterocyclic or 17-membered heterocyclic.

In some embodiments of Formula (I), R$_5$ is —F, —Cl, —Br, —NR$_8$R$_9$, methyl, ethyl, propyl, isopropyl, methoxy, ethoxy, propoxy, isopropoxy, 6-membered aryl, 7-membered aryl, 8-membered aryl, 9-membered aryl, 6-membered arylalkyl, 7-membered arylalkyl, 8-membered arylalkyl, 9-membered arylalkyl, 6-membered heteroaryl, 7-membered heteroaryl, 8-membered heteroaryl, 9-membered heteroaryl, 6-membered heterocyclic, 7-membered heterocyclic, 8-membered heterocyclic, 9-membered heterocyclic, 10-membered heterocyclic, 11-membered heterocyclic, 12-membered heterocyclic, 13-membered heterocyclic, 14-membered heterocyclic, 15-membered heterocyclic, 16-membered heterocyclic, 6-membered carbocyclic, 7-membered carbocyclic, 8-membered carbocyclic, 9-membered carbocyclic, 10-membered carbocyclic, 11-membered carbocyclic, 12-membered carbocyclic, 13-membered carbocyclic, 14-membered carbocyclic, 15-membered carbocyclic or 16-membered carbocyclic; and each heteroaryl contains 1, 2 or 3 heteroatoms select from N, O or S, and each heterocyclic contains 1, 2, 3, or 4 heteroatoms select from N, O or S; wherein each of which is independently optionally substituted with —F, —Cl, —Br, —I, —CN, —OH, —NO$_2$, —NH$_2$, carbonyl, =O, oxo, substituted or unsubstituted C$_{1-3}$alkyl, substituted or unsubstituted C$_{1-3}$alkoxy, substituted or unsubstituted (CH$_2$)$_k$NR$_8$R$_9$, substituted or unsubstituted (CH$_2$)$_k$NHC(O)OR$_8$, or substituted or unsubstituted C(O)R$_8$; and k is 0, 1 or 2.

In some embodiments of Formula (I),
R$_5$ is

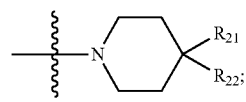

each R$_{21}$ and R$_{22}$ is independently halogen, C$_{1-3}$alkyl, —NH$_2$, —C$_{1-3}$alkylene-NH$_2$, —C$_{1-3}$alkylene-NH—C$_{1-3}$alkyl, —C$_{1-3}$alkylene-N(C$_{1-3}$alkyl)$_2$, —NHBoc or —CH$_2$NHBoc;

or $R_{21}$ and $R_{22}$ together with the carbon atom to which they are both attached form a 5-10 member heteroaryl, 5-10 member carbocyclic or a 5-10 member heterocyclic ring, wherein each of the ring system is optionally substituted with halogen, —CN, —OH, carbonyl, ═O, oxo, —$C_{1-3}$alkylene-NH$_2$, —$C_{1-3}$alkylene-NH—$C_{1-3}$alkyl, —$C_{1-3}$alkylene-N($C_{1-3}$alkyl)$_2$, —NHBoc, —CH$_2$NHBoc; —NH$_2$, $C_{1-3}$alkoxy or $C_{1-3}$alkyl.

In some embodiments of Formula (I), $R_{21}$ and $R_{22}$ together with the carbon atom to which they are both attached form a 5-membered heteroaryl, 6-membered heteroaryl, 7-membered heteroaryl, 8-membered heteroaryl, 9-membered heteroaryl, 10-membered heteroaryl, 5-membered heterocyclic ring, 6-membered heterocyclic ring, 7-membered heterocyclic ring, 8-membered heterocyclic ring, 9-membered heterocyclic ring or 10-membered heterocyclic ring; wherein each of the ring system contains 1, 2 or 3 heteroatoms select from N, O or S, and is independently optionally substituted with halogen, —CN, —OH, carbonyl, ═O, oxo, —NH$_2$, $C_{1-3}$alkoxy or $C_{1-3}$alkyl.

In some embodiments of Formula (I), X is O, S or absent.

In some embodiments of Formula (I), $Y_1$ is N and $Y_2$ is $CR_2$.

In some embodiments of Formula (I), $Y_2$ is N and $Y_1$ is $CR_1$.

In some embodiments of Formula (I), $R_4$ is —NH$_2$.

In some embodiments of Formula (I), $R_5$ is —NH$_2$,

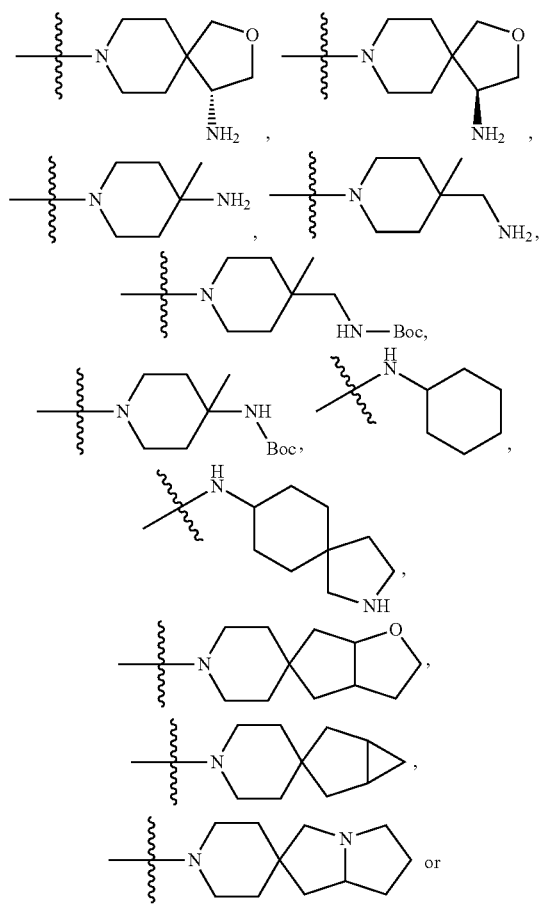

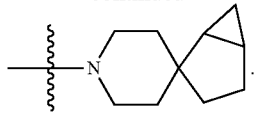

In some embodiments of Formula (I), each $R_8$ and $R_9$ is independently —H, halogen, CN, —OH, —NO$_2$, —NH$_2$, —$C_{1-6}$alkylene-NH$_2$, —$C_{1-6}$alkylene-NH—$C_{1-6}$alkyl, —$C_{1-6}$alkylene-N($C_{1-6}$alkyl)$_2$, —NHBoc, —CH$_2$NHBoc; —NH—$C_{1-6}$alkyl, —N($C_{1-6}$alkyl)$_2$, —NH—$C_{1-6}$alkoxy, —N($C_{1-6}$alkoxy)$_2$, $C_{1-6}$alkyl, $C_{1-6}$alkoxy, $C_{2-6}$alkenyl, $C_{2-6}$alkylnyl, $C_{5-10}$heterocyclic or $C_{5-10}$carbocyclic; each of which may be optionally substituted.

In some embodiments of Formula (I), each $R_8$ and $R_9$ is independently —H, —F, —Cl, —CN, —OH, —NO$_2$, —NH$_2$, —$C_{1-3}$alkylene-NH$_2$, —$C_{1-3}$alkylene-NH—$C_{1-3}$alkyl, —$C_{1-3}$alkylene-N($C_{1-3}$alkyl)$_2$, —NHBoc, —CH$_2$NHBoc; —NH—$C_{1-3}$alkyl, —N($C_{1-3}$alkyl)$_2$, —NH—$C_{1-3}$alkoxy, —N($C_{1-3}$alkoxy)$_2$, $C_{1-4}$alkyl, $C_{1-3}$alkoxy, $C_{2-3}$alkenyl, $C_{2-3}$alkylnyl, 5-membered heterocyclic, 6-membered heterocyclic, 7-membered heterocyclic, 8-membered heterocyclic, 9-membered heterocyclic, 10-membered heterocyclic, 5-membered carbocyclic, 6-membered carbocyclic, 7-membered carbocyclic, 8-membered carbocyclic, 9-membered carbocyclic or 10-membered carbocyclic; and each of which may be independently optionally substituted with halogen, —CN, —OH, —NH$_2$, —N$_3$, —NO$_2$, —$C_{1-6}$alkylene-NH$_2$, —$C_{1-6}$alkylene-NH—$C_{1-6}$alkyl, —$C_{1-6}$alkylene-N($C_{1-6}$alkyl)$_2$, —NHBoc, —CH$_2$NHBoc; —NH—$C_{1-6}$alkyl, —N($C_{1-6}$alkyl)$_2$, —NH—$C_{1-6}$alkoxy, —N($C_{1-6}$alkoxy)$_2$, substituted or unsubstituted $C_{1-6}$alkyl, or substituted or unsubstituted $C_{1-6}$alkoxy; and each heterocyclic contains 1, 2, 3 or 4 heteroatoms select from N, O or S.

In some embodiments of Formula (I), each $R_8$ and $R_9$ is independently —H, methyl, tert-butyl, —CH═CH$_2$, N(CH$_3$)$_2$,

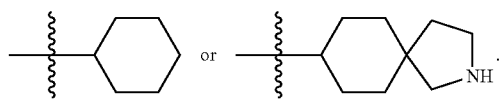

In some embodiments of Formula (I), the compound is of Formula II:

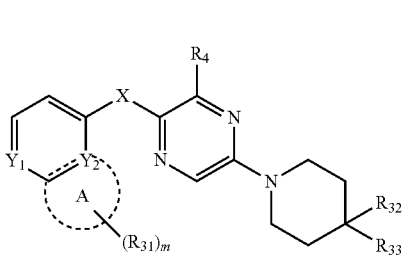

and
X is absent or S;
$Y_1$ is N or $CR_{25}$;
$Y_2$ is N or C;

$R_{25}$ is H, halogen, $C_{1-3}$alkyl, $C_{1-3}$alkoxy, $C_{2-3}$alkenyl or $C_{2-3}$alkylnyl;

ring

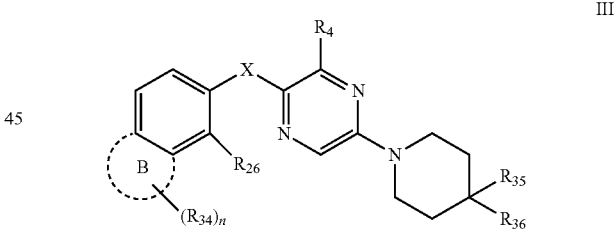

is 5-8 member heteroaryl containing 1, 2, 3 or 4 heteroatoms select form N, O or S, 5-8 member carbocyclic or 5-8 member heterocyclic ring containing 1, 2, 3 or 4 heteroatoms select form N, O or S;

$R_{31}$ is —H, halogen, —OH, —$NH_2$, —(C=O)$C_{1-3}$alkyl, —CN, —$NO_2$, carbonyl, =O, oxo, carboxyl, —$C_{1-3}$alkylene-$NH_2$, —$C_{1-3}$alkylene-NH—$C_{1-3}$alkyl, —$C_{1-3}$alkylene-N($C_{1-3}$alkyl)$_2$, —NHBoc, —$CH_2$NHBoc; —NH—$C_{1-3}$alkyl, —N($C_{1-3}$alkyl)$_2$, —NH—$C_{1-3}$alkoxy, —N($C_{1-3}$alkoxy)$_2$, substituted or unsubstituted $C_{1-3}$alkyl, or substituted or unsubstituted $C_{1-3}$alkoxy;

m is 0, 1, 2, 3 or 4;

$R_4$ is —H, halogen, —$NH_2$, substituted or unsubstituted $C_{1-3}$alkoxy, or substituted or unsubstituted $C_{1-3}$alkyl;

each $R_{32}$ and $R_{33}$ is independently —H, halogen, —OH, —$NH_2$, —CN, —$NO_2$, —$C_{1-3}$alkylene-$NH_2$, —$C_{1-3}$alkylene-NH—$C_{1-3}$alkyl, —$C_{1-3}$alkylene-N($C_{1-3}$alkyl)$_2$, —NHBoc, —$CH_2$NHBoc; —NH—$C_{1-3}$alkyl, —N($C_{1-3}$alkyl)$_2$, —NH—$C_{1-3}$alkoxy, —N($C_{1-3}$alkoxy)$_2$, substituted or unsubstituted $C_{1-3}$alkyl, or substituted or unsubstituted $C_{1-3}$alkoxy;

or $R_{32}$ and $R_{33}$ together with the carbon atom to which they are both attached form a 5-8 member heteroaryl containing 1, 2 or 3 heteroatoms select from N, O or S, or 5-8 member heterocyclic ring containing 1, 2 or 3 heteroatoms select from N, O or S, wherein each of the ring systems is optionally substituted with halogen, —CN, —OH, —$NH_2$, carbonyl, =O, oxo, —$CH_2NH_2$, —$C_{1-3}$alkylene-$NH_2$, —$C_{1-3}$alkylene-NH—$C_{1-3}$alkyl, —$C_{1-3}$alkylene-N($C_{1-3}$alkyl)$_2$, —NHBoc, —$CH_2$NHBoc; —NH—$C_{1-3}$alkyl, —N($C_{1-3}$alkyl)$_2$, —NH—$C_{1-3}$alkoxy, —N($C_{1-3}$alkoxy)$_2$, substituted or unsubstituted $C_{1-3}$alkyl, or substituted or unsubstituted $C_{1-3}$alkoxy.

The present invention further provides some preferred technical solutions with regard to compound of Formula (II).

In some embodiments of Formula (II), ring is 5-membered heteroaryl, 6-membered heteroaryl, 7-membered heteroaryl, 5-membered heterocyclic ring, 6-membered heterocyclic ring, 7-membered heterocyclic ring, 5-membered carbocyclic, 6-membered carbocyclic, 7-membered carbocyclic or 8-membered carbocyclic; and each the ring systems contains 1, 2 or 3 heteroatoms select form N, O or S.

In some embodiments of Formula (II), ring is 5-membered heterocyclic ring containing 1, 2 or 3 heteroatoms select form N or O, 6-membered heterocyclic ring containing 1 or 2 heteroatoms select form N or O or 5-membered carbocyclic.

In some embodiments of Formula (II), $R_{31}$ is —F, —$COCH_3$, carbonyl, =O, oxo, —$CH_3$ or —$CF_3$.

In some embodiments of Formula (II), $R_{32}$ and $R_{33}$ together with the carbon atom to which they are both attached to form a 5-membered heteroaryl, 6-membered heteroaryl, 7-membered heteroaryl, 5-membered heterocyclic ring, 6-membered heterocyclic ring, or 7-membered heterocyclic ring; wherein each of the ring systems contains 1, 2, or 3 heteroatoms select from N, O or S, and is optionally substituted with halogen, —CN, —OH, —$NH_2$, carbonyl, =O, oxo, —$CH_2NH_2$, —$C_{1-3}$alkylene-$NH_2$, —$C_{1-3}$alkylene-NH—$C_{1-3}$alkyl, —$C_{1-3}$alkylene-N($C_{1-3}$alkyl)$_2$, —NHBoc, —$CH_2$NHBoc; —NH—$C_{1-3}$alkyl, —N($C_{1-3}$alkyl)$_2$, —NH—$C_{1-3}$alkoxy, —N($C_{1-3}$alkoxy)$_2$, substituted or unsubstituted $C_{1-3}$alkyl, or substituted or unsubstituted $C_{1-3}$alkoxy.

In some embodiments of Formula (II), $R_{32}$ and $R_{33}$ together with the carbon atom to which they are both attached form a 5-membered heterocyclic ring; 6-membered heterocyclic ring or 7-membered heterocyclic ring; wherein each of the ring system containing 1 or 2 heteroatoms independently select from O or N, and is optionally substituted with halogen, —CN, —OH, —$NH_2$, carbonyl, =O, oxo, carboxyl, —$N_3$, —$NO_2$, $C_{1-3}$alkyl or $C_{1-3}$alkoxy.

In some embodiments of Formula (II), $R_{32}$ and $R_{33}$ together with the carbon atom to which they are both attached to form a 5-membered heterocyclic ring; and the heterocyclic ring contains 1 heteroatoms selected from O or N, and is optionally substituted with —F, —Cl, —OH, —$NH_2$, carbonyl, =O, oxo, methyl or methoxy.

In some embodiments of Formula (II), each $R_{32}$ and $R_{33}$ is independently —$CH_2NH_2$, —$CH_2$NHBoc or methyl.

In some embodiments of Formula (II), $Y_1$ is N.

In some embodiments of Formula (II), $Y_2$ is C.

In some embodiments of Formula (II), is —H or —Cl.

In some embodiments of Formula (II), $R_4$ is —$NH_2$.

In some embodiments of Formula (I), the compound is of Formula III:

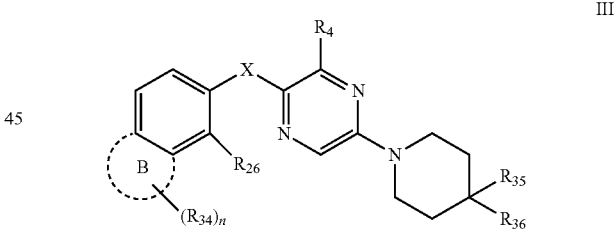

and

X is absent or S;

$R_{26}$ is —H, halogen, substituted or unsubstituted $C_{1-3}$alkyl, or substituted or unsubstituted $C_{1-3}$alkoxy;

ring is 5-8 member heteroaryl or 5-8 member heterocyclic ring; and each the ring system independently contains 1, 2, 3 or 4 heteroatoms select form N, O or S;

$R_{34}$ is —H, halogen, —OH, —$NR_{35}R_{36}$, —CN, —$NO_2$, carbonyl, =O, oxo, substituted or unsubstituted $C_{1-3}$alkyl, or substituted or unsubstituted $C_{1-3}$alkoxy;

n is 0, 1, 2 or 3;

$R_4$ is —H, halogen, —$NH_2$, substituted or unsubstituted $C_{1-6}$alkoxy, or substituted or unsubstituted $C_{1-6}$ alkyl;

each $R_{35}$ and $R_{36}$ is independently —H, halogen, —OH, —$NH_2$, —CN, —$NO_2$, —$CH_2NH_2$, substituted or unsubstituted $C_{1-3}$alkyl, or substituted or unsubstituted $C_{1-3}$alkoxy;

or $R_{35}$ and $R_{36}$ together with the carbon atom to which they are both attached to form a 5-8 member heteroaryl or 5-8 member heterocyclic ring, wherein each of the ring system independently contains 1, 2 or 3 heteroatoms select from N, O or S, and is optionally substituted with halogen, —CN, —OH, —$NH_2$, carbonyl, =O, oxo, —$CH_2NH_2$, —$C_{1-3}$alkylene-$NH_2$, —$C_{1-3}$alkylene-NH—$C_{1-3}$alkyl, —$C_{1-3}$alkylene-N($C_{1-3}$alkyl)$_2$, —NHBoc, —$CH_2$NHBoc; —NH—$C_{1-3}$alkyl, —N($C_{1-3}$alkyl)$_2$, —NH$C_{1-3}$alkoxy, —N($C_{1-3}$alkoxy)$_2$, substituted or unsubstituted $C_{1-3}$alkyl, or substituted or unsubstituted $C_{1-3}$alkoxy.

The present invention further provides some preferred technical solutions with regard to compound of Formula (III).

In some embodiments of Formula (III), ring

is 5-membered heteroaryl, 6-membered heteroaryl, 7-membered heteroaryl, 5-membered heterocyclic ring, 6-membered heterocyclic ring or 7-membered heterocyclic ring; and each of the ring system independently contains 1, 2 or 3 heteroatoms select form N, O or S.

In some embodiments of Formula (III), ring

is 5-membered heterocyclic ring or 6-membered heterocyclic ring; and each of the ring system independently contains 1 or 2 heteroatoms select form N or O.

In some embodiments of Formula (III), $R_{35}$ and $R_{36}$ together with the carbon atom to which they are both attached to form a 5-membered heteroaryl, 6-membered heteroaryl, 7-membered heteroaryl, 5-membered heterocyclic ring, 6-membered heterocyclic ring or 7-membered heterocyclic ring; wherein each of the ring system is independently contains 1, 2, or 3 heteroatoms select from N, O or S, and is optionally substituted with halogen, —CN, —OH, —$NH_2$, carbonyl, =O, oxo, —$CH_2NH_2$, —$C_{1-3}$alkylene-$NH_2$, —$C_{1-3}$alkylene-NH—$C_{1-3}$alkyl, —$C_{1-3}$alkylene-N($C_{1-3}$alkyl)$_2$, —NHBoc, —$CH_2$NHBoc; —NH—$C_{1-3}$alkyl, —N($C_{1-3}$alkyl)$_2$, —NH$C_{1-3}$alkoxy, —N($C_{1-3}$alkoxy)$_2$, substituted or unsubstituted $C_{1-3}$alkyl, or substituted or unsubstituted $C_{1-3}$alkoxy.

In some embodiments of Formula (III), $R_{35}$ and $R_{36}$ together with the carbon atom to which they are both attached to form a 5-membered heterocyclic ring; 6-membered heterocyclic ring or 7-membered heterocyclic ring; wherein each of the ring system is independently contains 1 or 2 heteroatoms independently select from O or N, and is optionally substituted with halogen, —CN, —OH, —$NH_2$, carbonyl, =O, oxo, carboxyl, —$N_3$, —$NO_2$, $C_{1-3}$alkyl or $C_{1-3}$alkoxy.

In some embodiments of Formula (III), $R_{35}$ and $R_{36}$ together with the carbon atom to which they are both attached to form a 5-membered heterocyclic ring; wherein the ring system contains 1 heteroatom independently select from O or N, and is optionally substituted with —F, —Cl, —OH, —$NH_2$, carbonyl, =O, oxo, methyl or methoxy.

In some embodiments of Formula (III), $R_{26}$ is —H or —Cl In some embodiments of Formula (III), $R_4$ is —$NH_2$.

In some embodiments of Formula (III), $R_{34}$ is —F, —$COCH_3$, carbonyl, =O, oxo, —$CH_3$ or —$CF_3$.

In some embodiments of Formula (I), Formula (II) or Formula (III), each substituted or unsubstituted $C_{1-6}$alkyl is independently $C_{1-6}$alkyl, or $C_{1-6}$alkyl substituted with halogen, —OH, —CN, $NH_2$, —$NO_2$, carbonyl, =O, oxo, —$C_{1-6}$alkylene-$NH_2$, —$C_{1-6}$alkylene-NH—$C_{1-6}$alkyl, or —$C_{1-6}$alkylene-N($C_{1-6}$alkyl)$_2$; each substituted or unsubstituted $C_{1-6}$alkoxy is independently $C_{1-6}$alkoxy, or $C_{1-6}$alkoxy substituted with halogen, —OH, —CN, $NH_2$, —$NO_2$, carbonyl, =O, oxo, —$C_{1-6}$alkylene-$NH_2$, —$C_{1-6}$alkylene-NH—$C_{1-3}$alkyl, or —$C_{1-6}$alkylene-N($C_{1-6}$alkyl)$_2$.

In some embodiments of Formula (I), Formula (II) or Formula (III), each substituted or unsubstituted $C_{1-3}$alkyl is independently $C_{1-3}$alkyl, or $C_{1-3}$alkyl substituted with halogen, —OH, —CN, $NH_2$, —$NO_2$, carbonyl, =O, oxo, —$C_{1-3}$alkylene-$NH_2$, —$C_{1-3}$alkylene-NH—$C_{1-3}$alkyl, or —$C_{1-3}$alkylene-N($C_{1-3}$alkyl)$_2$; each substituted or unsubstituted $C_{1-3}$alkoxy is independently $C_{1-3}$alkoxy, or $C_{1-3}$alkoxy substituted with halogen, —OH, —CN, $NH_2$, —$NO_2$, carbonyl, =O, oxo, —$C_{1-3}$alkylene-$NH_2$, —$C_{1-3}$alkylene-NH—$C_{1-3}$alkyl, or —$C_{1-3}$alkylene-N($C_{1-3}$alkyl)$_2$.

In some embodiments of Formula (I), Formula (II) or Formula (III), each $C_{1-6}$alkyl is independently methyl, ethyl, propyl, isopropyl, cyclopropyl, n-butyl, isobutyl, tert-buyl, n-pentyl, neopentyl, isopentyl, cyclopentyl, n-hexyl or cyclohexyl.

In some embodiments of Formula (I), Formula (II) or Formula (III), each $C_{1-3}$alkyl is independently methyl, ethyl, propyl, isopropyl or cyclopropyl.

In some embodiments of Formula (I), Formula (II) or Formula (III), each $C_{1-3}$alkoxy is independently methoxy, ethoxy, propoxy, isopropoxy or cyclopropyloxy.

In some embodiments of Formula (I), Formula (II) or Formula (III), each $C_{2-3}$alkenyl is independently —CH=$CH_2$, —$CH_2$—CH=$CH_2$, or —CH=CH—$CH_3$.

In some embodiments of Formula (I), Formula (II) or Formula (III), each $C_{2-3}$alkylnyl is independently —C≡CH, —$CH_2$—C≡CH, or —C≡C—$CH_3$.

In some embodiments of Formula (I), Formula (II) or Formula (III), each halogen is independently —F, —Cl, —Br or —I.

In some embodiments of Formula (I), Formula (II) or Formula (III), each heterocyclic group and each carbocyclic group includes single ring, spiral ring, bridge ring, fused ring and all various combinations of spiral ring, bridge ring, and/or fused ring.

In some embodiments of Formula (I), Formula (II) or Formula (III), the said single ring includes the said spiral ring includes

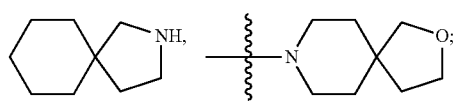

and the said various combinations of spiral ring, bridge ring, and/or fused ring include

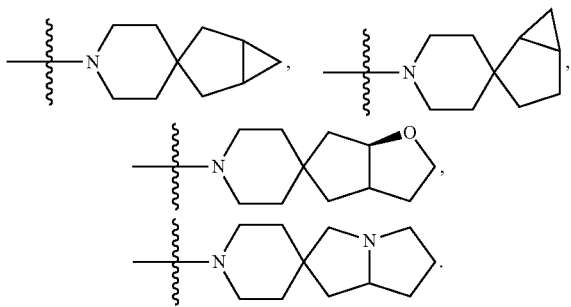

The present invention further provides some preferred technical solutions with regard to compound of Formula (I) or Formula (II), compound is 1) (S)-N1-(3-((3-amino-5-(4-amino-2-oxa-8-azaspiro[4.5]decan-8-yl)pyrazin-2-yl)thio)-2-chlorophenyl)-N2,N2-dimethyloxalamide hydrochloride;
2) $N^1$-(4-((3-amino-5-(4-amino-4-methylpiperidin-1-yl)pyrazin-2-yl)thio)-3-chloropyridin-2-yl)-$N^2$,$N^2$-dimethyloxalamide;
3) N-(3-((3-amino-5-(4-amino-4-methylpiperidin-1-yl)pyrazin-2-yl)thio)-2-chlorophenyl)-4-(2-(dimethylamino)-2-oxoacetyl)benzamide;
4) 6-((3-amino-5-(4-(aminomethyl)-4-methylpiperidin-1-yl)pyrazin-2-yl)thio)-2H-benzo[b][1,4]oxazin-3(4H)-one;
5) 6-(3-amino-5-(4-(aminomethyl)-4-methylpiperidin-1-yl)pyrazin-2-yl)-2H-benzo[b][1,4]oxazin-3(4H)-one;
6) 5-((2-amino-3-chloropyridin-4-yl)thio)-N2-(2-azaspiro[4.5]decan-8-yl)pyrazine-2,6-diamine;
7) (S)-1-(4-((3-amino-5-(4-amino-2-oxa-8-azaspiro[4.5]decan-8-yl)pyrazin-2-yl)thio)-3,3-difluoroindolin-1-yl)ethanone;
8) (S)-4-((3-amino-5-(4-amino-2-oxa-8-azaspiro[4.5]decan-8-yl)pyrazin-2-yl)thio)-3,3-difluoroindolin-2-one;
9) 4-((3-amino-5-(4-(aminomethyl)-4-methylpiperidin-1-yl)pyrazin-2-yl)thio)indolin-2-one;
10) (S)-4-((3-amino-5-(4-amino-2-oxa-8-azaspiro[4.5]decan-8-yl)pyrazin-2-yl)thio)-3,3-difluoro-1H-pyrrolo[2,3-b]pyridin-2(3H)-one;
11) (R)-N-((S)-8-(6-amino-5-((3,3-difluoro-1-methyl-2-oxoindolin-4-yl)thio)pyrazin-2-yl)-2-oxa-8-azaspiro[4.5]decan-4-yl)-2-methylpropane-2-sulfinamide;
12) (S)-4-((3-amino-5-(4-amino-2-oxa-8-azaspiro[4.5]decan-8-yl)pyrazin-2-yl)thio)indoline-2,3-dione hydrochloride;
13) tert-butyl ((1-(5-((1-acetyl-3,3-difluoroindolin-4-yl)thio)-6-aminopyrazin-2-yl)-4-methylpiperidin-4-yl)methyl)carbamate;
14) 4-((3-amino-5-(4-(aminomethyl)-4-methylpiperidin-1-yl)pyrazin-2-yl)thio)indoline-2,3-dione;
15) 5-((2-amino-3-chloropyridin-4-yl)thio)-6-(4-(aminomethyl)-4-methylpiperidin-1-yl)pyrazin-2-amine;
16) $N^1$-(4-((3-amino-5-(4-(aminomethyl)-4-methylpiperidin-1-yl)pyrazin-2-yl)thio)-3-chloropyridin-2-yl)-N2,N2-dimethyloxalamide;
17) tert-butyl ((1-(6-amino-5-((2-amino-3-chloropyridin-4-yl)thio)pyrazin-2-yl)-4-methylpiperidin-4-yl)methyl)carbamate;
18) (S)-N1-(4-((3-amino-5-(4-amino-2-oxa-8-azaspiro[4.5]decan-8-yl)pyrazin-2-yl)thio)-3-chloropyridin-2-yl)-N2,N2-dimethyloxalamide;
19) (S)-$N^1$-(3-((3-amino-5-(4-amino-2-oxa-8-azaspiro[4.5]decan-8-yl)pyrazin-2-yl)thio)-2-chlorophenyl)-$N^2$,$N^2$-dimethyloxalamide;
20) $N^1$-(3-((3-amino-5-(4-(aminomethyl)-4-methylpiperidin-1-yl)pyrazin-2-yl)thio)-2-chlorophenyl)-$N^2$,$N^2$-dimethyloxalamide;
21) N-(3-((3-amino-5-(4-(aminomethyl)-4-methylpiperidin-1-yl)pyrazin-2-yl)thio)-2-chlorophenyl)-3-(2-(dimethylamino)-2-oxoacetyl)benzamide;
22) 2-(3-(3-((3-amino-5-(4-(aminomethyl)-4-methylpiperidin-1-yl)pyrazin-2-yl)thio)-2-chlorophenyl)ureido)phenyl)-N,N-dimethyl-2-oxoacetamide;
23) 2-(4-(3-((3-amino-5-(4-(aminomethyl)-4-methylpiperidin-1-yl)pyrazin-2-yl)thio)-2-chlorophenyl)ureido)phenyl)-N,N-dimethyl-2-oxoacetamide;
24) 6-(4-(aminomethyl)-4-methylpiperidin-1-yl)-3-((3,4-dihydro-2H-benzo[b][1,4]oxazin-6-yl)thio)pyrazin-2-amine;
25) tert-butyl (1-(6-amino-5-((2-amino-3-chloropyridin-4-yl)thio)pyrazin-2-yl)-4-methylpiperidin-4-yl)carbamate;
26) tert-butyl (1-(5-((2-acrylamido-3-chloropyridin-4-yl)thio)-6-aminopyrazin-2-yl)-4-methylpiperidin-4-yl)carbamate;
27) tert-butyl (1-(6-amino-5-((3-chloro-2-(2-(dimethylamino)-2-oxoacetamido)pyridin-4-yl)thio)pyrazin-2-yl)-4-methylpiperidin-4-yl)carbamate;
28) tert-butyl (1-(6-amino-5-((2-chloro-3-(2-(dimethylamino)-2-oxoacetamido)phenyl)thio)pyrazin-2-yl)-4-methylpiperidin-4-yl)carbamate;
29) $N^1$-(3-((3-amino-5-(4-amino-4-methylpiperidin-1-yl)pyrazin-2-yl)thio)-2-chlorophenyl)-$N^2$,$N^2$-dimethyloxalamide;
30) tert-butyl (1-(6-amino-5-((3-amino-2-chlorophenyl)thio)pyrazin-2-yl)-4-methylpiperidin-4-yl)carbamate;
31) N-(3-((3-amino-5-(4-amino-4-methylpiperidin-1-yl)pyrazin-2-yl)thio)-2-chlorophenyl)-2-oxo-2-(p-tolyl)acetamide;
32) tert-butyl (1-(5-((3-acrylamido-2-chlorophenyl)thio)-6-aminopyrazin-2-yl)-4-methylpiperidin-4-yl)carbamate;
33) 6-(3-amino-5-(4-amino-4-methylpiperidin-1-yl)pyrazin-2-yl)-2H-benzo[b][1,4]oxazin-3(4H)-one;
34) N-(4-((3-amino-5-(4-amino-4-methylpiperidin-1-yl)pyrazin-2-yl)thio)-3-chloropyridin-2-yl)-4-(2-(dimethylamino)-2-oxoacetyl)benzamide;
35) N-(4-((3-amino-5-(4-(aminomethyl)-4-methylpiperidin-1-yl)pyrazin-2-yl)thio)-3-chloropyridin-2-yl)-4-(2-(dimethylamino)-2-oxoacetyl)benzamide;
36) N-(3-((3-amino-5-(4-(aminomethyl)-4-methylpiperidin-1-yl)pyrazin-2-yl)thio)-2-chlorophenyl)-4-(2-(dimethylamino)-2-oxoacetyl)benzamide;
37) 5-((2-amino-3-chloropyridin-4-yl)thio)-N2-cyclohexylpyrazine-2,6-diamine;
38) (S)-8-(5-((1H-pyrrolo[2,3-b]pyridin-4-yl)thio)-6-aminopyrazin-2-yl)-2-oxa-8-azaspiro[4.5]decan-4-amine;
39) (S)-8-(6-amino-5-((3,3-dimethylindolin-4-yl)thio)pyrazin-2-yl)-2-oxa-8-azaspiro[4.5]decan-4-amine;
40) (S)-8-(6-amino-5-((3-fluoro-1H-indol-4-yl)thio)pyrazin-2-yl)-2-oxa-8-azaspiro[4.5]decan-4-amine;
41) 5-((2-amino-3-chloropyridin-4-yl)thio)-N2-(4-(aminomethyl)-4-methylcyclohexyl)pyrazine-2,6-diamine;
42) (S)-8-(5-((1H-indol-4-yl)thio)-6-aminopyrazin-2-yl)-2-oxa-8-azaspiro[4.5]decan-4-amine;
43) (S)-1-(4-((3-amino-5-(4-amino-2-oxa-8-azaspiro[4.5]decan-8-yl)pyrazin-2-yl)thio)-1H-indol-1-yl)ethanone;
44) 5-((2-amino-3-chloropyridin-4-yl)thio)-N2-(4-amino-4-methylcyclohexyl)pyrazine-2,6-diamine;
45) (S)-6-((3-amino-5-(4-amino-2-oxa-8-azaspiro[4.5]decan-8-yl)pyrazin-2-yl)thio)-2H-benzo[b][1,4]oxazin-3(4H)-one;

46) (S)-4-((3-amino-5-(4-amino-2-oxa-8-azaspiro[4.5]decan-8-yl)pyrazin-2-yl)thio)-1,3,3-trimethylindolin-2-one;
47) (4S)-8-(6-amino-5-((3-fluoroindolin-4-yl)thio)pyrazin-2-yl)-2-oxa-8-azaspiro[4.5]decan-4-amine;
48) 1-(4-((3-amino-5-((S)-4-amino-2-oxa-8-azaspiro[4.5]decan-8-yl)pyrazin-2-yl)thio)-3-fluoro-3-methylindolin-1-yl)ethanone;
49) (S)-8-(6-amino-5-((3,3-difluoroindolin-4-yl)thio)pyrazin-2-yl)-2-oxa-8-azaspiro[4.5]decan-4-amine;
50) 1-(4-((3-amino-5-((S)-4-amino-2-oxaspiro[4.5]decan-8-yl)pyrazin-2-yl)thio)-3-methylindolin-1-yl)ethanone;
51) (S)-8-(6-amino-5-((8-chloro-4,4-difluoro-1,2,3,4-tetrahydroquinolin-5-yl)thio)pyrazin-2-yl)-2-oxa-8-azaspiro[4.5]decan-4-amine;
52) (4S)-8-(6-amino-5-((8-chloro-4-fluoro-1,2,3,4-tetrahydroquinolin-5-yl)thio)pyrazin-2-yl)-2-oxa-8-azaspiro[4.5]decan-4-amine;
53) (S)-8-(6-amino-5-((3,3-difluoro-1-methylindolin-4-yl)thio)pyrazin-2-yl)-2-oxa-8-azaspiro[4.5]decan-4-amine;
54) (S)-6-((3-amino-5-(4-amino-2-oxa-8-azaspiro[4.5]decan-8-yl)pyrazin-2-yl)thio)-3,3-difluoroindolin-2-one;
55) 4-((3-amino-5-((S)-4-amino-2-oxa-8-azaspiro[4.5]decan-8-yl)pyrazin-2-yl)thio)-3-fluoroindolin-2-one;
56) (S)-8-(6-amino-5-((3,3-difluoro-2,3-dihydrobenzofuran-4-yl)thio)pyrazin-2-yl)-2-oxa-8-azaspiro[4.5]decan-4-amine;
57) (S)-8-(6-amino-5-((4,4-difluorochroman-5-yl)thio)pyrazin-2-yl)-2-oxa-8-azaspiro[4.5]decan-4-amine;
58) 4-((3-amino-5-((S)-4-amino-2-oxa-8-azaspiro[4.5]decan-8-yl)pyrazin-2-yl)thio)-3-fluoro-1-methyl-3-(trifluoromethyl)indolin-2-one;
59) (S)-6-((3-amino-5-(4-amino-2-oxa-8-azaspiro[4.5]decan-8-yl)pyrazin-2-yl)thio)-7-chloroindolin-2-one;
60) (S)-8-(6-amino-5-((5-chloro-3,4-dihydro-2H-benzo[b][1,4]oxazin-6-yl)thio)pyrazin-2-yl)-2-oxa-8-azaspiro[4.5]decan-4-amine;
61) (S)-7-((3-amino-5-(4-amino-2-oxa-8-azaspiro[4.5]decan-8-yl)pyrazin-2-yl)thio)-8-chloro-3,4-dihydroquinolin-2(1H)-one;
62) (S)-6-((3-amino-5-(4-amino-2-oxa-8-azaspiro[4.5]decan-8-yl)pyrazin-2-yl)thio)-5-chloro-2H-benzo[b][1,4]oxazin-3(4H)-one;
63) (S)-2-(3-((3-amino-5-(4-amino-2-oxa-8-azaspiro[4.5]decan-8-yl)pyrazin-2-yl)thio)-2-chlorophenyl)-N,N-dimethyl-2-oxoacetamide;
64) 4-((3-amino-5-(4-(aminomethyl)-4-methylpiperidin-1-yl)pyrazin-2-yl)thio)-3,3-difluoro-1H-pyrrolo[2,3-b]pyridin-2(3H)-one;
65) (S)-4-((3-amino-5-(4-amino-2-oxa-8-azaspiro[4.5]decan-8-yl)pyrazin-2-yl)thio)-1H-benzo[d]imidazol-2(3H)-one;
66) (S)-4-((3-amino-5-(4-amino-2-oxa-8-azaspiro[4.5]decan-8-yl)pyrazin-2-yl)thio)-1,3-dimethyl-1H-benzo[d]imidazol-2(3H)-one;
67) (S)-8-(6-amino-5-((2,2-difluoro-2,3-dihydro-1H-benzo[d]imidazol-4-yl)thio)pyrazin-2-yl)-2-oxa-8-azaspiro[4.5]decan-4-amine;
68) (S)-8-(6-amino-5-((2,2-difluoro-1,3-dimethyl-2,3-dihydro-1H-benzo[d]imidazol-4-yl)thio) pyrazin-2-yl)-2-oxa-8-azaspiro[4.5]decan-4-amine;
69) (4S)-8-(6-amino-5-((1-amino-3,3-difluoro-2,3-dihydro-1H-inden-4-yl)thio)pyrazin-2-yl)-2-oxa-8-azaspiro[4.5]decan-4-amine;
70) (S)-5-((3-amino-5-(4-amino-2-oxa-8-azaspiro[4.5]decan-8-yl)pyrazin-2-yl)thio)-2-methyl-[1,2,4]triazolo[4,3-a]pyridin-3(2H)-one;
71) (S)-8-(6-amino-5-((3,3-difluoro-2-methyl-2,3-dihydro-[1,2,4]triazolo[4,3-a]pyridin-5-yl)thio)pyrazin-2-yl)-2-oxa-8-azaspiro[4.5]decan-4-amine;
72) (S)-1-(4-((3-amino-5-(4-amino-2-oxa-8-azaspiro[4.5]decan-8-yl)pyrazin-2-yl)thio)indolin-1-yl)ethanone;
73) 1'-(6-amino-5-((2-amino-3-chloropyridin-4-yl)thio)pyrazin-2-yl)hexahydrospiro[cyclopenta[b]furan-5,4'-piperidin]-4-amine;
74) 1'-(6-amino-5-((2-amino-3-chloropyridin-4-yl)thio)pyrazin-2-yl)spiro[bicyclo[3.1.0]hexane-3,4'-piperidin]-2-amine;
75) 1'-amino-1-(6-amino-5-((2-amino-3-chloropyridin-4-yl)thio)pyrazin-2-yl)tetrahydrospiro[piperidine-4,2'-pyrrolizin]-3'(1'H)-one;
76) 1'-(6-amino-5-((2-amino-3-chloropyridin-4-yl)thio)pyrazin-2-yl)spiro[bicyclo[3.1.0]hexane-2,4'-piperidin]-3-amine.

The present invention also provides a pharmaceutical composition comprising at least one compound described herein and at least one pharmaceutically acceptable excipient. In composition, the said compound in a weight ratio to the said excipient within the range from about 0.0001 to about 10. any one of Formula (I), Formula (II) or Formula (III)

The present invention additionally provided a use of the pharmaceutical composition of as described herein for the preparation of a medicament.

In some embodiments, a medicament thus prepared can be used for the treatment or prevention of cancer, cancer metastasis, cardiovascular disease, an immunological disorder or an ocular disorder.

The present invention additionally provided a use of at least one compound described herein to prepare of a medicament.

In some embodiments, a medicament thus prepared can be used for the treatment or prevention of cancer, cancer metastasis, cardiovascular disease, an immunological disorder or an ocular disorder.

At least one compound for use described herein which is for use in the treatment of cancer, the prevention of cancer metastasis or the treatment of cardiovascular disease, an immunological disorder or an ocular disorder.

Use, in the manufacture of a medicament for use as an inhibitor of SHP2, of at least one compound described herein.

A method of treating a patient having a condition which is mediated by the activity of SHP2, said method comprising administering to the patient a therapeutically effective amount of at least one compound described herein, or a pharmaceutically acceptable salt thereof.

In some embodiments, the condition mediated by the activity of SHP2 is cancer.

In some embodiments, the condition mediated by the activity of SHP2 is noonan syndrome, leopard syndrome, juvenile myelomonocytic leukemias, liver cancer, neuroblastoma, melanoma, squamous-cell carcinoma of the head and neck, acute myeloid leukemia, breast cancer, esophageal cancer, lung cancer, colon cancer, head cancer, gastric carcinoma, neuroblastoma, anaplastic large-cell lymphoma and glioblastoma.

At least one compound described herein or a pharmaceutically acceptable salt thereof for use as a medicament.

At least one compound described herein or a pharmaceutically acceptable salt thereof for use in the treatment of cancer.

A method of treating cancer selected from the group consisting of noonan syndrome, leopard syndrome, juvenile myelomonocytic leukemias, liver cancer, neuroblastoma, melanoma, squamous-cell carcinoma of the head and neck, acute myeloid leukemia, breast cancer, esophageal cancer, lung cancer, colon cancer, head cancer, gastric carcinoma, neuroblastoma, anaplastic large-cell lymphoma and glioblastoma in a mammal comprising administering to a mammal in need of such treatment an effective amount of at least one compound described herein or a pharmaceutically acceptable salt thereof The term "halogen", as used herein, unless otherwise indicated, means fluoro, chloro, bromo or iodo. The preferred halogen groups include F, Cl and Br. The terms "haloC$_{1-6}$alkyl", "haloC$_{2-6}$alkenyl", "haloC$_{2-6}$alkynyl" and "haloC$_{1-6}$alkoxy" mean a C$_{1-6}$alkyl, C$_{2-6}$alkenyl, C$_{2-6}$alkynyl or C$_{1-6}$alkoxy in which one or more (in particular, 1 to 3) hydrogen atoms have been replaced by halogen atoms, especially fluorine or chlorine atoms. In some embodiment, preferred are fluoroC$_{1-6}$alkyl, fluoroC$_{2-6}$alkenyl, fluoroC$_{2-6}$alkynyl and fluoroC$_{1-6}$alkoxy groups, in particular fluoroC$_{1-3}$alkyl, for example, CF$_3$, CHF$_2$, CH$_2$F, CH$_2$CH$_2$F, CH$_2$CHF$_2$, CH$_2$CF$_3$ and fluoroC$_{1-3}$alkoxy groups, for example, OCF$_3$, OCHF$_2$, OCH$_2$F, OCH$_2$CH$_2$F, OCH$_2$CHF$_2$ or OCH$_2$CF$_3$, and most especially CF$_3$, OCF$_3$ and OCHF$_2$.

As used herein, unless otherwise indicated, alkyl includes saturated monovalent hydrocarbon radicals having straight, branched or cyclic moieties. For example, alkyl radicals include methyl, ethyl, propyl, isopropyl, cyclcopropyl, n-butyl, isobutyl, sec-butyl, t-butyl, cyclcobutyl, n-pentyl, 3-(2-methyl) butyl, 2-pentyl, 2-methylbutyl, neopentyl, cyclcopentyl, n-hexyl, 2-hexyl, 2-methylpentyl and cyclohexyl. Similarly, C$_{1-8}$, as in C$_{1-8}$alkyl is defined to identify the group as having 1, 2, 3, 4, 5, 6, 7 or 8 carbon atoms in a linear or branched arrangement.

Alkylene means a difunctional group obtained by removal of a hydrogen atom from an alkyl group that is defined above. For example, methylene (i.e., —CH$_2$—), ethylene (i.e., —CH$_2$—CH$_2$— or —CH(CH$_3$)—) and propylene (i.e., —CH$_2$—CH$_2$—CH$_2$—, —CH(—CH$_2$—CH$_3$)— or —CH$_2$—CH(CH$_3$)—).

Alkenyl and alkynyl groups include straight, branched chain or cyclic alkenes and alkynes. Likewise, "C$_{2-8}$alkenyl" and "C$_{2-8}$alkynyl" means an alkenyl or alkynyl radicals having 2, 3, 4, 5, 6, 7 or 8 carbon atoms in a linear or branched arrangement.

Alkoxy radicals are oxygen ethers formed from the previously described straight, branched chain or cyclic alkyl groups.

The term "aryl", as used herein, unless otherwise indicated, refers to an unsubstituted or substituted mono- or polycyclic ring system containing carbon ring atoms. The preferred aryls are mono cyclic or bicyclic 6-10 membered aromatic ring systems. Phenyl and naphthyl are preferred aryls. The most preferred aryl is phenyl.

The term "heterocyclic", as used herein, unless otherwise indicated, refers to unsubstituted and substituted mono- or polycyclic non-aromatic ring system containing one or more heteroatoms. Preferred heteroatoms include N, O, and S, including N-oxides, sulfur oxides, and dioxides. Preferably the ring is three to eight membered and is either fully saturated or has one or more degrees of unsaturation. Multiple degrees of substitution, preferably one, two or three, are included within the present definition.

Examples of such heterocyclic groups include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl", as used herein, unless otherwise indicated, represents an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junction, for example, bycyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "cycloalkyl" refers to a substituted or unsubstituted monocyclic, bicyclic or polycyclic non-aromatic saturated ring, which optionally includes an alkylene linker through which the cycloalkyl may be attached. Examplary "cycloalkyl" groups includes but not limited to, cyclopropyl, cyclobutyl, cyclopentyl, cyclohexyl and so on.

The term "carbonyl, =O or oxo" refers to the group C(O).

Whenever the term "alkyl" or "aryl" or either of their prefix roots appear in a name of a substituent (e.g., aralky or dialkylamino) it shall be interpreted as including those limitations given above for "alkyl" and "aryl." Designated numbers of carbon atoms (e.g., C$_{1-6}$) shall refer independently to the number of carbon atoms in an alkyl moiety or to the alkyl portion of a larger substituent in which alkyl appears as its prefix root.

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

The compounds of the present invention may also be present in the form of pharmaceutically acceptable salts. For use in medicine, the salts of the compounds of this invention refer to non-toxic "pharmaceutically acceptable salts". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula (I) exists, the present invention includes any possible tautomers and pharmaceutically acceptable salts thereof, and mixtures thereof, except where specifically stated otherwise.

When the compound of Formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. When the compound of the present invention is basic, its corresponding salt can be conveniently prepared from pharmaceutically acceptable non-toxic acids, including inorganic and organic acids. Since the compounds of Formula (I) are intended for pharmaceutical use they are preferably provided in substantially pure form, for example at least 60% pure, more suitably at least 75% pure, especially at least 98% pure (% are on a weight for weight basis).

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

These and other aspects will become apparent from the following written description of the invention.

EXAMPLES

The following Examples are provided to better illustrate the present invention. All parts and percentages are by weight and all temperatures are degrees Celsius, unless explicitly stated otherwise. The following abbreviations have been used in the examples:
DAST: Diethylaminosulfur trifluoride;
DCM: Dichloromethane;
DIEA: N,N-Diisopropylethylamine;
DMF: N,N-Dimethylformamide;
DMSO: Dimethyl sulfoxide;
EA: Ethyl acetate;
EtOH: Ethanol;
NMP: N-methyl-2-pyrrolidone;
TEA: Triethylamine;
THF: Tetrahydrofuran
TFA: Trifluoroacetic acid;
Xantphos: Dimethylbisdiphenylphosphinoxanthene;
min: Minute;
rt or RT: room temperature;
TLC: Thin layer chromatography;
Pre-TLC: Preparation by thin layer chromatogaraphy.

Example 1 Synthesis of Compound 1

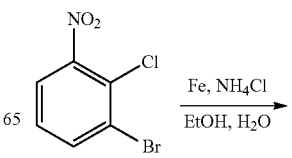

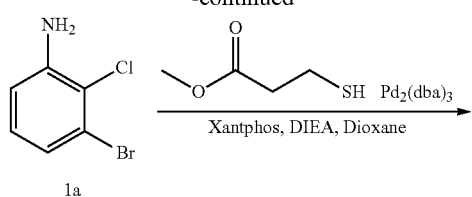

1a

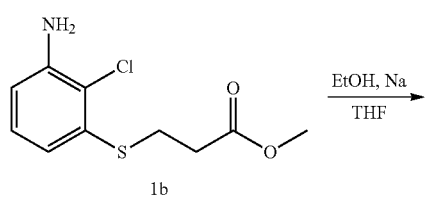

1b

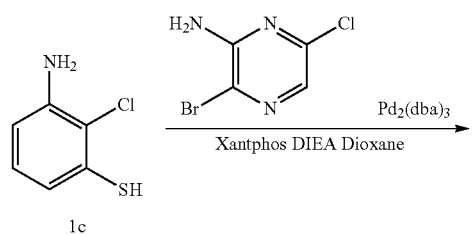

1c

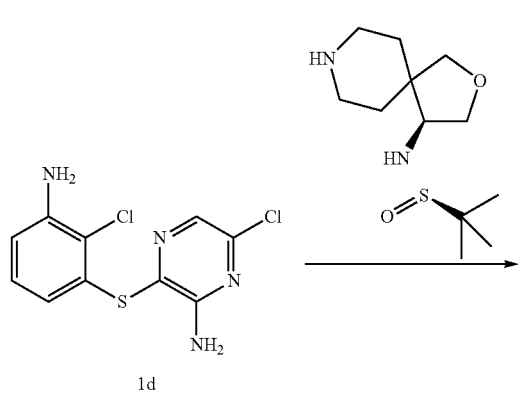

1d

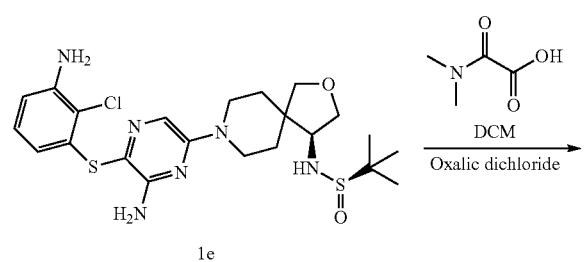

1e

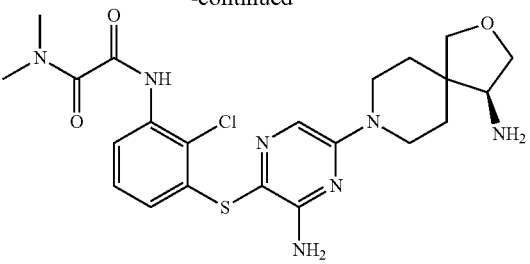

1f

1

A mixture of 1-bromo-2-chloro-3-nitrobenzene (36.61 g, 154.83 mmol), iron powder (43.35 g, 774.16 mmol), NH$_4$Cl (8.28 g, 154.83 mmol), EtOH (100 mL) and H$_2$O (50 mL) was heated to 60° C. for 4 hours, then cooled to 10° C. The reaction mixture was filtered through a pad of Celite and the filtrate was concentrated to remove the EtOH. The residual solution was extracted with EA (100 mL×2). The combined organic extracts were washed with brine (100 mL), dried over anhydrous Na$_2$SO$_4$ and concentrated under reduced pressure to afford the compound 1a (30.01 g, 93.88%). MS: 206 (M+H)$^+$.

A mixture of the compound 1a (30.00 g, 0.15 mol), methyl 3-mercaptopropanoate (27.60 g, 0.23 mol), Pd$_2$(dba)$_3$ (1.37 g, 1.5 mmol), Xantphos (1.73 g, 3.00 mmol), DIEA (38.75 g, 0.30 mol) in dioxane (200 mL) was stirred at 95° C. under N$_2$ for 18 hours. After completion of the reaction, the reaction mixture was concentrated under reduced pressure and purified by column chromatography to afford the compound 1b (10.00 g, 27.13%). MS: 246 (M+H)$^+$.

A mixture of Na (1.22 g, 52.90 mmol) and EtOH (25 mL) was stirred at 20° C. until the Na dissolved completely. The compound 1b (10.00 g, 40.70 mmol) in THF (30 mL) was added dropwise at −30° C.~−20° C., then the mixture was stirred at 20° C. for 3.5 hours, and concentrated under reduced pressure. The residue was added water (50 mL), extracted with EA (50 mL×2). The water phase was adjusted pH=2-3 with HCl solution (1 mol/L) and extracted with EA (50 mL×2). The combined organic extracts were washed with brine (50 mL), dried over anhydrous Na$_2$SO$_4$ and filtered and concentrated under reduced pressure to afford the compound 1c (6.02 g, 92.66%). MS: 160 (M+H)+.

A mixture of the compound 1c (6.02 g, 37.71 mol), 3-bromo-6-chloropyrazin-2-amine (7.86 g, 37.71 mol), Pd$_2$(dba)$_3$ (0.35 g, 0.38 mmol), Xantphos (0.43 g, 0.75 mmol), DIEA (9.74 g, 75.42 mol) in dioxane (70 mL) was stirred at 95° C. under N$_2$ for 17 hours. After completion of the reaction, the mixture was filtered and the filtrate was concentrated under reduced pressure. The residue was added EA (50 mL) and stirred for 0.5 hour, then filtered to afford the compound 1d (8.45, 78.03%). MS: 287 (M+H)$^+$.

A solution of the compound 1d (0.81 g, 2.82 mmol), (R)-2-methyl-N-((S)-2-oxa-8-azaspiro[4.5]decan-4-yl)propane-2-sulfinamide (TFA salt, 1.26 g, 3.38 mmol) and K$_2$CO$_3$ (1.17 g, 8.46 mmol) in NMP (10 mL) was stirred for 14 hours at 130° C. After cooling to RT, the resulting residue was dissolved in EA (100 mL), washed with H$_2$O (30 mL), dried over anhydrous Na$_2$SO$_4$, filtered and the volatiles were removed under reduced pressure and purified by column chromatography to afford the compound 1e (0.55 g, 38%). MS: 511 (M+H)$^+$.

Oxalyl chloride was added dropwise to a solution of 2-(dimethylamino)-2-oxoacetic acid (0.26 g, 2.15 mmol) in DCM (10 mL), and stirred at RT for 2 hours, the volatiles were removed under reduced pressure, the residue was dissolved in DCM (10 mL) and added dropwise to a solution of the compound 1e (0.55 g, 1.08 mmol) in DCM (10 mL), after completion of the reaction, the reaction mixture was quenched by addition of ice-water (20 mL), washed with brine, dried over anhydrous Na$_2$SO$_4$, filtered and the volatiles were removed under reduced pressure and purified by column chromatography to afford the compound 1f (0.42 g, 64%). MS: 610 (M+H)$^+$.

The compound 1f (0.41 g, 0.67 mmol) and HCl (4M in dioxane, 5 mL) in DCM (10 mL) was stirred for 20 min at 40° C. After cooling to RT, HCl (1M in H$_2$O) was added and the resulting aqueous mixture was extracted with DCM. The aqueous phase was basified with NH$_4$OH (28% in H$_2$O) until pH to 12 and extracted with DCM (3×20 mL). The combined organic layers were washed with brine, dried over anhydrous Na$_2$SO4, filtered, concentrated under reduced pressure, and purified by column chromatography to afford the compound 1 (100 mg, 32%). MS: 506 (M+H)+.

$^1$HNMR (DMSO-d6, 400 MHz): δ 7.63 (s, 1H), 7.43-7.45 (d, 1H), 7.21-7.23 (d, 1H), 6.50-6.52 (d, 1H), 6.11 (s, 1H), 4.00-4.05 (m, 4H), 3.93-3.96 (dd, 2H), 2.93-3.29 (m, 4H), 1.54-1.98 (m, 4H).

Example 2 Synthesis of Compound 2

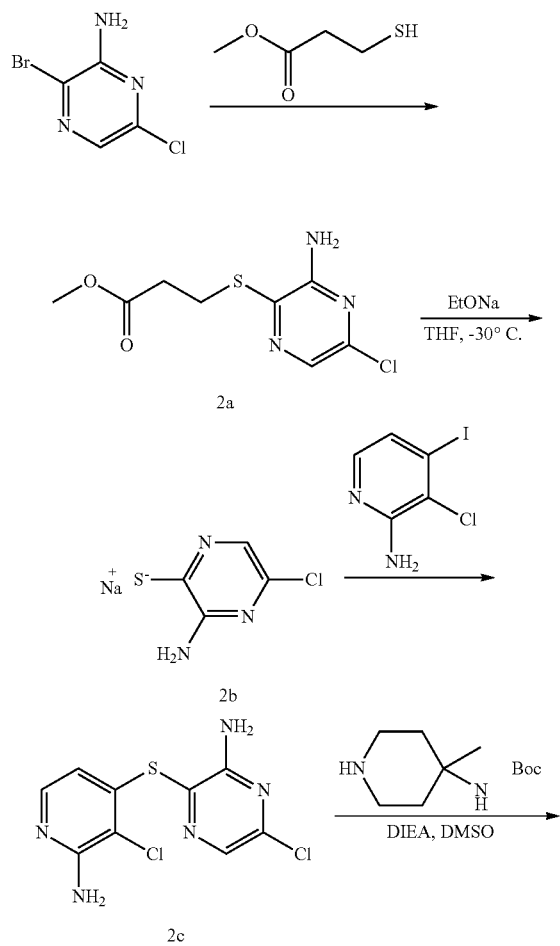

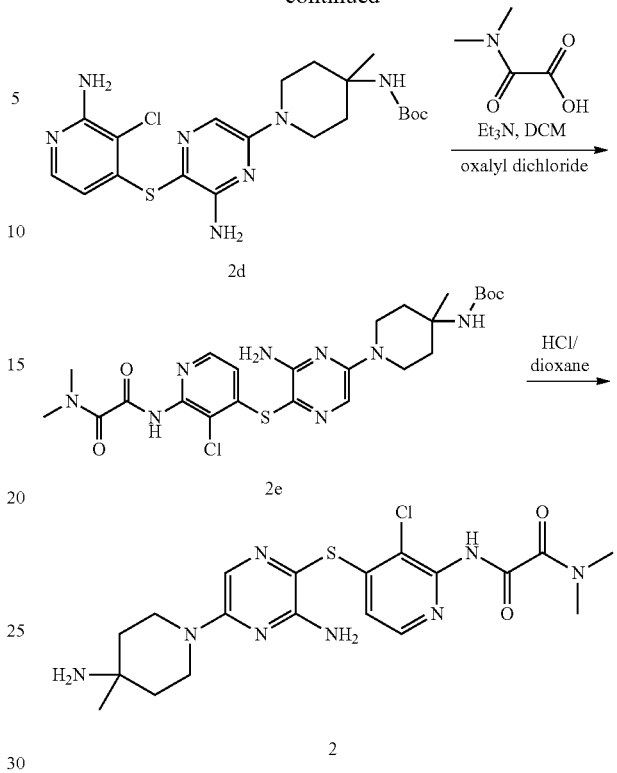

A mixture of 3-bromo-6-chloropyrazin-2-amine (20.02 g, 96.05 mmol), methyl 3-mercaptopropanoate (11.53 g, 96.05 mmol), DIEA (24.83 g, 192.10 mmol), Pd(OAc)$_2$ (0.30 g, 1.34 mmol), Xantphos (2.78 g, 4.8 mmol) in dixoane (200 mL) was heated to 95° C. under N$_2$ for 18 hours. The reaction mixture was filtered, concentrated under reduced pressure, and purified by column chromatography to afford the compound 2a (18.83 g, 79%). MS: 248 (M+H)$^+$.

A solution of the compound 2a (18.33 g, 76.02 mmol) in THF (150 mL) was cooled to −30° C. Sodium ethoxide (6.72 g, 98.82 mmol) in ethanol (100 mL) was added dropwise. The resulting mixture was stirred at −30° C. for 1 hours, then warmed to 25° C. and stirred for another 2 hours. The volatiles were removed under reduced pressure and dissolved in DCM (100 mL), the precipitate was filtered to give the compound 2b as a brown solid (13.82 g, 99%). MS: 162 (M+H)$^+$.

A mixture of the compound 2b (9.98 g, 54.36 mmol), 3-chloro-4-iodopyridin-2-amine (13.83 g, 54.36 mmol), DIEA (14.04 g, 108.72 mmol), Pd$_2$(dba)$_3$ (1.00 g, 1.09 mmol), Xantphos (1.00 g, 1.73 mmol) in dioxane (200 mL) was heated to 95° C. under N$_2$ for 18 hours. The reaction mixture was filtered and concentrated under reduced pressure, the residue was dissolved in DCM (100 mL), the precipitate was filtered to afford the compound 2c as a brown solid (14.62 g, 93.72%). MS: 288 (M+H)$^+$.

A mixture of the compound 2c (2.31 g, 8.05 mmol), tert-butyl (4-methylpiperidin-4-yl)carbamate (3.45 g, 16.10 mmol), DIEA (3.12 g, 24.15 mmol) in DMSO (50 mL) was stirred at 100° C. for 3 hours. Water (100 mL) was added to the reaction mixture and the precipitate was filtered to give the compound 2d as a brown solid (2.19 g, 58%). MS: 466 (M+H)$^+$.

To a solution of 2-(dimethylamino)-2-oxoacetic acid (350 mg, 3 mmol) in DCM (10 mL) was added oxalyl dichloride (760 mg, 6 mmol) and DMF (2 drops). The resulting mixture was stirred at 20° C. for 1 hour. The volatiles were removed under reduced pressure and the residue was dissolved in DCM (10 mL), then the mixture was added to the solution of the compound 2d (460 mg, 1 mmol) and TEA (1 mL) in DCM (10 mL). After completion of the reaction, the reaction mixture was concentrated in vacuo, the residue was purified by Pre-TLC to afford the compound 2e as a yellow solid (142 mg, 25%). MS: 565 (M+H)+.

A mixture of the compound 2e (142 mg, 0.25 mmol) in HCl/dioxane (10 mL, 4M) was stirred for 1 hour. The precipitate was filtered to afford the compound 2 as a brown solid (70 mg, 60%). MS: 465 (M+H)+.

$^1$HNMR (DMSO-d6, 400 MHz): δ 8.45-8.35 (m, 2H), 8.06 (s, 1H), 7.71 (s, 1H), 6.45 (s, 1H), 4.06 (s, 6H), 3.38 (t, 2H), 2.93 (t, 2H), 2.86 (s, 2H), 1.84-1.71 (m, 4H), 1.39 (s, 3H).

Example 3 Synthesis of Compound 3

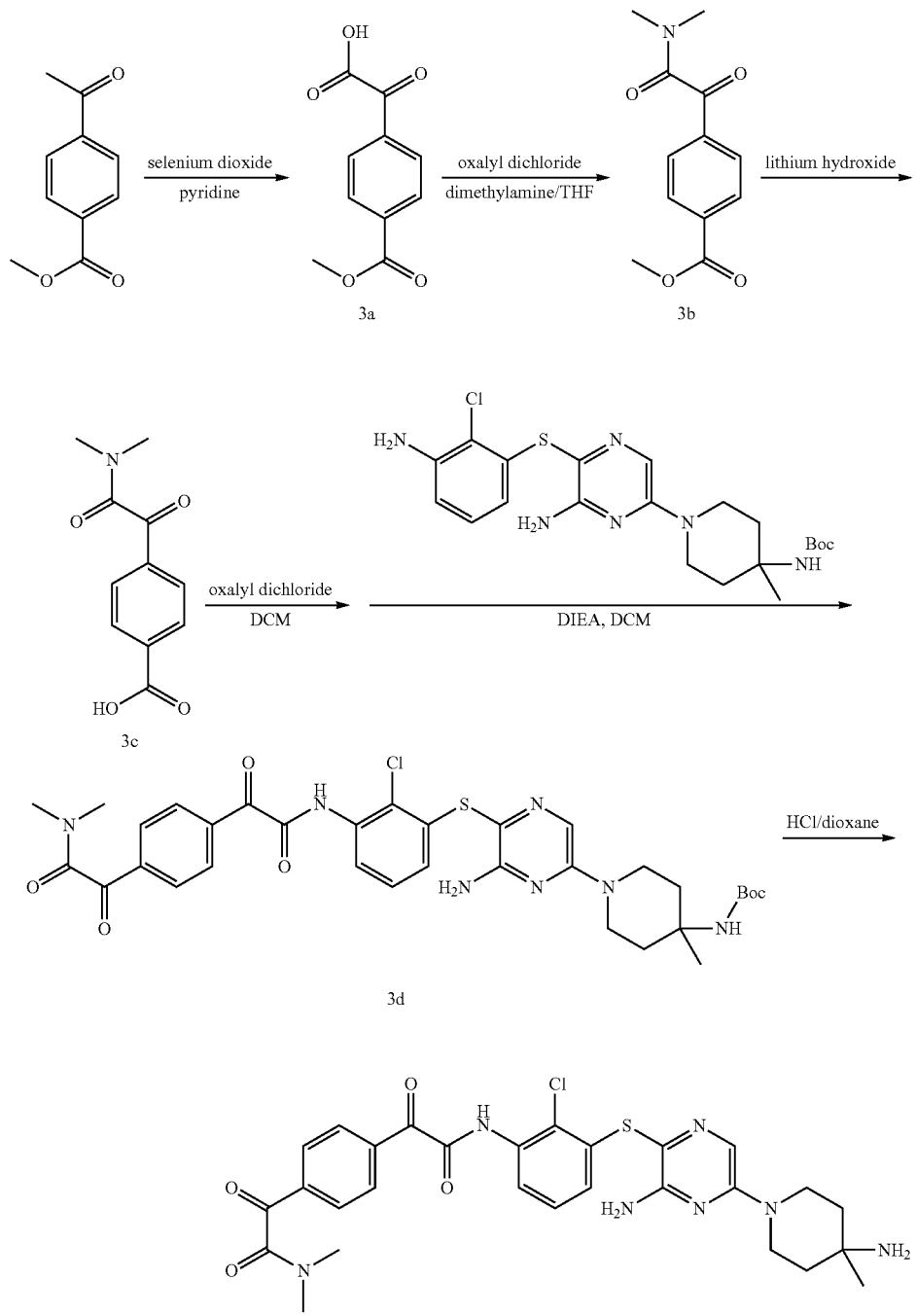

A mixture of methyl 4-acetylbenzoate (7.01 g, 40.00 mmol), selenium dioxide (8.95 g, 80.00 mmol) and pyridine (50 mL) was heated to 100° C. for 4 hours. Hydrochloric acid (70 mL, 1M) was added to the reaction mixture to adjust pH=3, the aqueous solution was extracted with EA (70 mL). The combined organic extracts were dried over anhydrous $Na_2SO_4$, concentrated in vacuo to afford the compound 3a as a brown solid (6.12 g, 74%). MS: m/z 207 (M–H)$^-$.

To a solution of the compound 3a (2.51 g, 12.07 mmol) in DCM (30 mL) was added oxalyl dichloride (15 mL) and DMF (2 drops). The resulting mixture was stirred at 20° C. for 1 hour. The volatiles were removed under reduced pressure and the residue was dissolved in DCM (100 mL), then the mixture was added to the solution of dimethylamine/THF (10 mL, 2M). After completion of the reaction, the reaction mixture was concentrated to afford the compound 3b as a brown solid (2.35 g, 83%). MS: 236 (M+H)$^+$.

A mixture of the compound 3b (0.91 g, 4.11 mmol), lithium hydroxide monohydrate (0.85 g, 20.55 mmol), $H_2O$ (10 mL) in methanol (50 mL) was stirred at 25° C. for 1 hour. The volatiles were removed under reduced pressure and the residue was dissolved in hydrochloric acid (25 mL, 1M), the aqueous solution was extracted with EA (20 mL×2). The combined organic extracts were washed with brine (50 mL), dried over anhydrous $Na_2SO_4$, filtered and the volatiles were removed under reduced pressure to afford the compound 3c as a brown solid (0.85 g, 93%). MS: 222 (M+H)$^+$.

To a solution of the compound 3c (0.85 g, 3.85 mmol) in DCM (10 mL) was added oxalyl dichloride (8 mL) and DMF (2 drops). The resulting mixture was stirred at 20° C. for 1 hour. The volatiles were removed under reduced pressure and the residue was dissolved in DCM (10 mL), then the mixture was added to the solution of tert-butyl (1-(6-amino-5-((3-amino-2-chlorophenyl)thio)pyrazin-2-yl)-4-methylpiperidin-4-yl)carbamate (200 mg, 0.43 mmol) and DIEA (5 mL) in DCM (10 mL). After completion of the reaction, the reaction mixture was concentrated in vacuo, the residue was purified by Pre-TLC to afford the compound 3d as a yellow solid (170 mg, 57%). MS: 696 (M+H)$^+$.

To a solution of HCl/dioxane (1 mL, 4M) was added the compound 3d (170 mg, 0.24 mmol), the resulting mixture was stirred at 25° C. for 1 hour and the precipitate was filtered to give the crude product (107 mg). The crude product was purified by Pre-TLC to afford the compound 3 as a brown solid (35 mg, 24%). MS: 596 (M+H)$^+$.

$^1$HNMR (DMSO-d6, 400 MHz): δ 10.44 (s, 1H), 8.39 (s, 1H), 8.18 (d, 2H), 8.02 (d, 2H), 7.68 (s, 1H), 7.36 (d, 1H), 7.26 (t, 1H), 6.58 (d, 1H), 6.18 (s, 1H), 4.03 (d, 2H), 3.37 (d, 2H), 3.04 (s, 3H), 2.90 (s, 3H), 1.83-1.71 (m, 4H), 1.39 (s, 3H).

Example 4 Synthesis of Compound 4

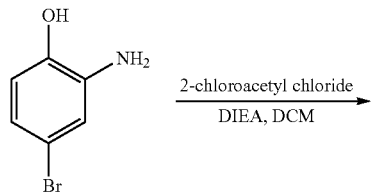

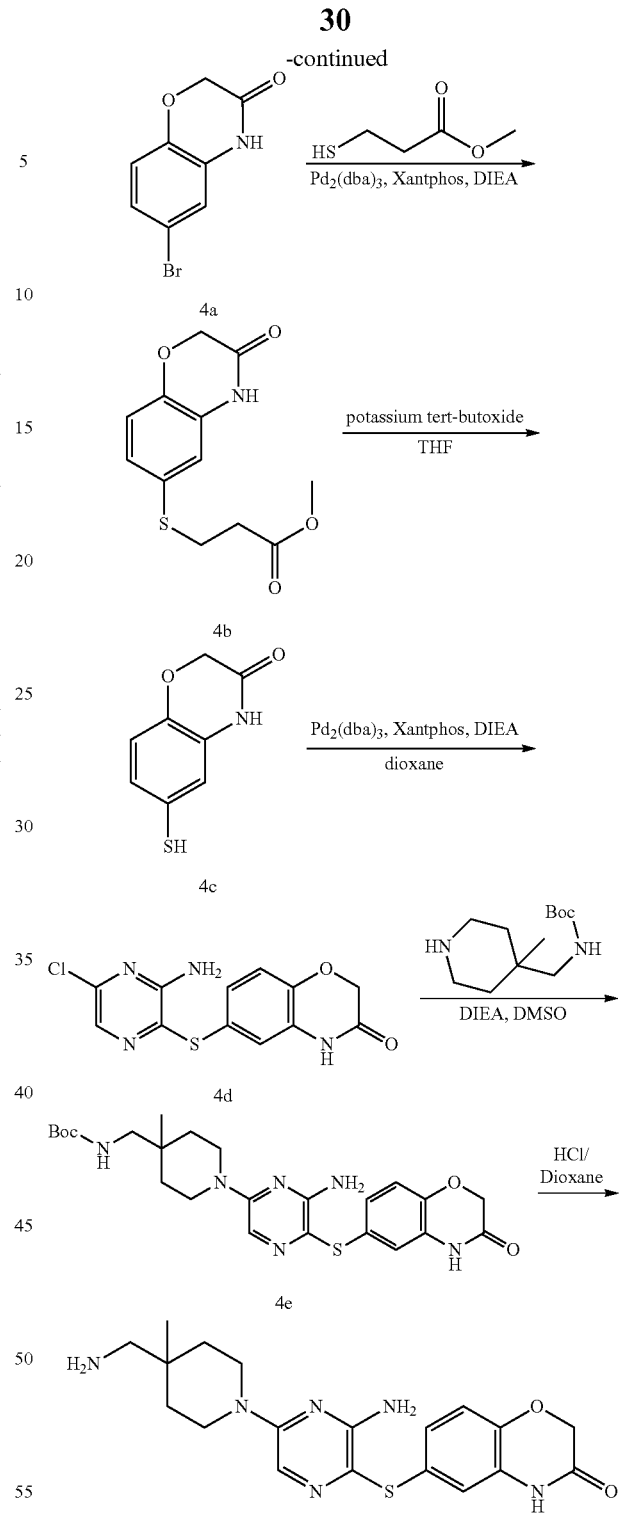

A mixture of 2-amino-4-bromophenol (10.15 g, 354.29 mmol), 2-chloroacetyl chloride (7.35 g, 65.15 mmol) and DCM (150 mL) was cooled to 0° C. DIEA (35.06 g, 271.45 mmol) was added dropwise, the resulting mixture was stirred at 20° C. for 5 hours. The reaction mixture was concentrated in vacuo and $H_2O$ (70 mL) was added, the precipitate was filtered to afford the compound 4a as a red solid (7.61 g, 62%). MS: 228 (M+H)$^+$.

A solution of the compound 4a (7.51 g, 33.09 mmol), methyl 3-mercaptopropanoate (5.16 g, 43.02 mmol), DIEA (8.55 g, 62.18 mmol), Pd$_2$(dba)$_3$ (0.40 g, 0.44 mmol), Xantphos (0.40 g, 0.69 mmol) in dioxane (100 mL) was heated to 100° C. under N$_2$ for 8 hours. The reaction mixture was filtered and concentrated under reduced pressure, the residue was purified by column chromatography to afford the compound 4b (5.12 g, 58%). MS: 268 (M+H)$^+$.

A solution of the compound 4b (3.75 g, 14.04 mmol) in THF (50 mL) was cooled to −70° C., potassium tert-butoxide/THF (28 mL, 28.08 mmol) was added dropwise, the resulting mixture was stirred at −70° C. for 0.5 hour. Hydrochloric acid (15 mL, 1 mol/L) was added to the reaction mixture, the aqueous solution was extracted with EA (20 mL×2). The combined organic extracts were washed with brine (50 mL), dried over anhydrous Na$_2$SO$_4$, filtered and the volatiles were removed under reduced pressure to afford the compound 4c as a red solid (1.57 g, 62%). MS: 182 (M+H)$^+$.

A mixture of the compound 4c (3.22 g, 17.79 mmol), 3-bromo-6-chloropyrazin-2-amine (3.68 g, 17.79 mmol), DIEA (4.60 g, 35.58 mmol), Pd$_2$(dba)$_3$ (0.15 g, 0.16 mmol), Xantphos (0.15 g, 0.26 mmol) in dioxane (30 mL) was heated to 100° C. under N$_2$ for 18 hours. The reaction mixture was filtered and concentrated under reduced pressure, the residue was dissolved in the solution of Hexane (10 mL) and EA (10 mL), the precipitate was filtered to afford the compound 4d as a brown solid (2.88 g, 52%). MS: 309 (M+H)$^+$.

A mixture of the compound 4d (0.35 g, 1.13 mmol), tert-butyl ((4-methylpiperidin-4-yl)methyl)carbamate (0.39 g, 1.70 mmol), DIEA (0.36 g, 2.83 mmol) in DMSO (10 mL) was stirred at 100° C. for 2 hours. H$_2$O (10 mL) was added to the reaction mixture, the aqueous solution was extracted with EA (10 mL×2). The combined organic extracts were washed with brine (50 mL), dried over anhydrous Na$_2$SO$_4$, filtered and the volatiles were removed under reduced pressure. The residue was purified by column chromatography to afford the compound 4e (0.15 g, 27%). MS: 501 (M+H)$^+$.

To a solution of HCl/Dixoane (1 mL, 4 mol/L) was added the compound 4e (150 mg, 0.30 mmol). The resulting mixture was stirred at 25° C. for 1 hour and the precipitate was filtered to afford the compound 4 as a white solid (60 mg, 50%). MS: 401 (M+H)$^+$.

$^1$HNMR (DMSO-d6, 400 MHz): δ 7.5 (s, 1H), 6.87 (d, 1H), 6.75 (d, 1H), 6.73 (s, 1H), 6.00 (s, 1H), 4.52 (s, 2H), 3.78-3.74 (m, 2H), 3.30-3.27 (m, 2H), 2.39 (s, 2H), 1.43-1.39 (m, 2H), 1.27-1.25 (m, 2H), 0.91 (s, 3H).

Example 5 Synthesis of Compound 5

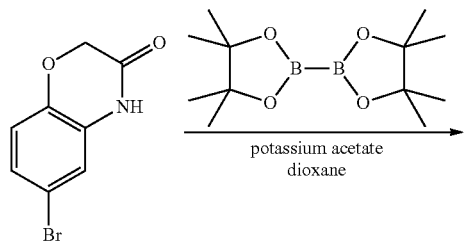

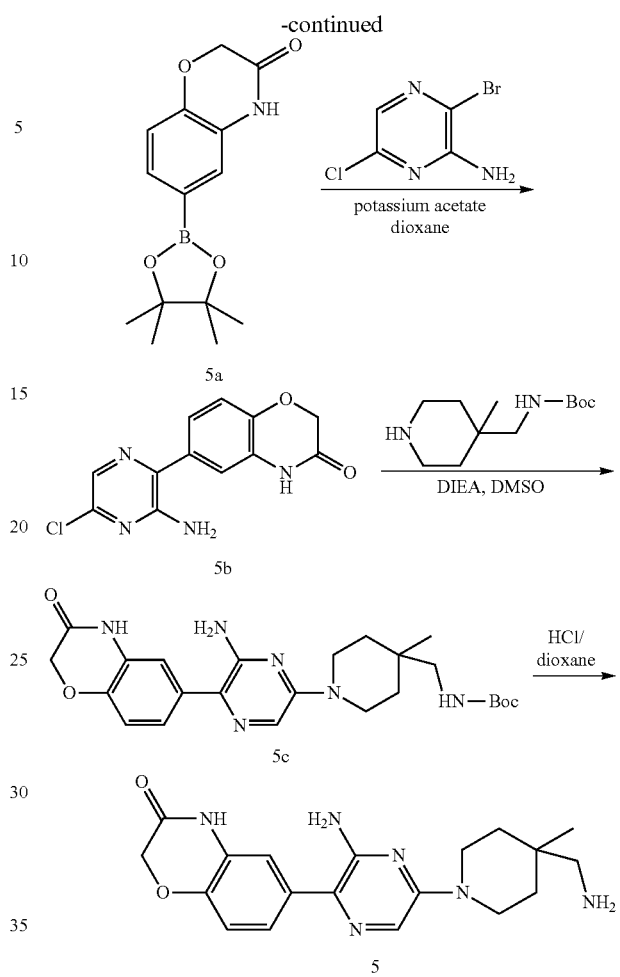

A solution of the compound 4a (3.33 g, 14.67 mmol), 4,4,4',4',5,5,5',5'-octamethyl-2,2'-bi(1,3,2-dioxaborolane) (4.48 g, 17.61 mmol), potassium acetate (2.88 g, 29.34 mmol), Pd(dppf)Cl$_2$ (0.15 g, 0.20 mmol) in dioxane (40 mL) was heated to 100° C. under N$_2$ for 24 hours. The reaction mixture was filtered and concentrated under reduced pressure, the residue was purified by column chromatography to afford the compound 5a (2.25 g, 56%). MS: 276 (M+H)$^+$.

A solution of the compound 5a (2.20 g, 8.00 mmol), 3-bromo-5-chloropyrazin-2-amine (1.54 g, 7.27 mmol), potassium acetate (2.00 g, 14.54 mmol), Pd(dppf)Cl$_2$ (0.15 g, 0.20 mmol), H$_2$O (2 mL) in dioxane (40 mL) was heated to 75° C. under N$_2$ for 4 hours. Hexane (50 mL) was added, the precipitate was filtered to afford the compound 5b as a brown solid (0.79 g, 36%). MS: 277 (M+H)$^+$.

A mixture of the compound 5b (230 mg, 0.83 mmol), tert-butyl ((4-methylpiperidin-4-yl)methyl)carbamate (0.29 g, 1.25 mmol), DIEA (0.43 g, 3.33 mmol) in DMSO (10 mL) was stirred at 100° C. for 18 hours. H$_2$O (20 mL) was added to the reaction mixture, the aqueous solution was extracted with EA (20 mL×2). The combined organic extracts were washed with brine (20 mL), dried over anhydrous Na$_2$SO$_4$, filtered and the volatiles were removed under reduced pressure, the residue was purified by column chromatography to afford the compound 5c 157 mg, 40%). MS: 469 (M+H)$^+$.

To a solution of HCl/dioxane (1 mL, 4M) was added the compound 5c (150 mg, 0.34 mmol). the resulting mixture was stirred at 25° C. for 1 hour and the precipitate was filtered to afford the compound 5 as a brown solid (72 mg, 56%). MS: 369 (M+H)$^+$.

$^1$HNMR (DMSO-d6, 400 MHz): δ 7.55 (s, 1H), 7.21 (d, 1H), 7.17 (d, 1H), 7.15 (d, 1H), 4.57 (s, 2H), 3.77 (t, 2H), 3.30 (t, 2H), 2.73 (s, 2H), 1.53-1.38 (m, 4H), 1.07 (s, 3H).

Example 6 Synthesis of Compound 6

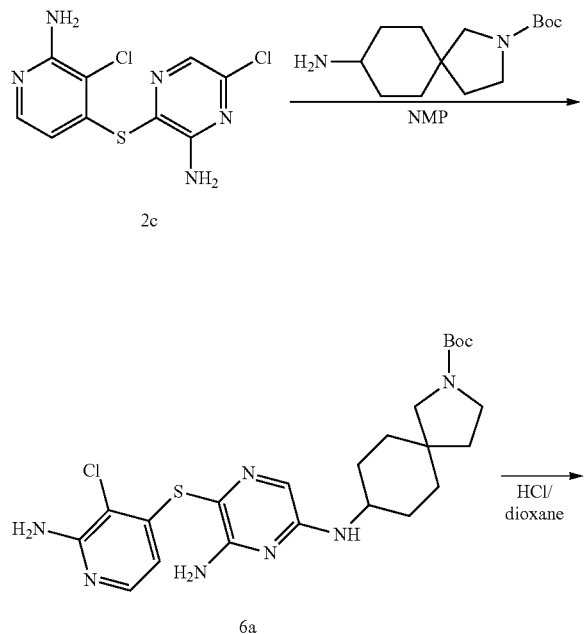

The oil bath was heated to 160° C., a mixture of the compound 2c (80 mg, 0.28 mmol) in NMP (5 mL) was stirred at 160° C., then tert-butyl 8-amino-2-azaspiro[4.5]decane-2-Carboxylate (190 mg, 0.75 mmol) was added. 1.5 hours later. The reaction mixture was cooled and water (40 mL) was added, the resulting mixture was extracted with EA (20 mL×2). The combined organic extracts were washed with brine (30 mL), dried over anhydrous Na$_2$SO$_4$ filtered and the volatiles were removed under reduced pressure. The residue was purified by Pre-TLC to afford the compound 6a (15 mg, 10.59%). MS: 506 (M+H)$^+$.

A mixture of the compound 6a (39 mg, 0.08 mmol), HCl/dioxane (4 mol/L, 1 mL), and dioxane (2 mL) was stirred at 20° C. for 1 hour. The mixture was concentrated under reduced pressure, the residue was added EA (5 mL) and stirred for 5 mins. The solid was filtered to afford the compound 6 as an HCl salt (30 mg, 84.76%). MS: 203.7 (M+2H)$^{2+}$.

Example 7 Synthesis of Compound 7

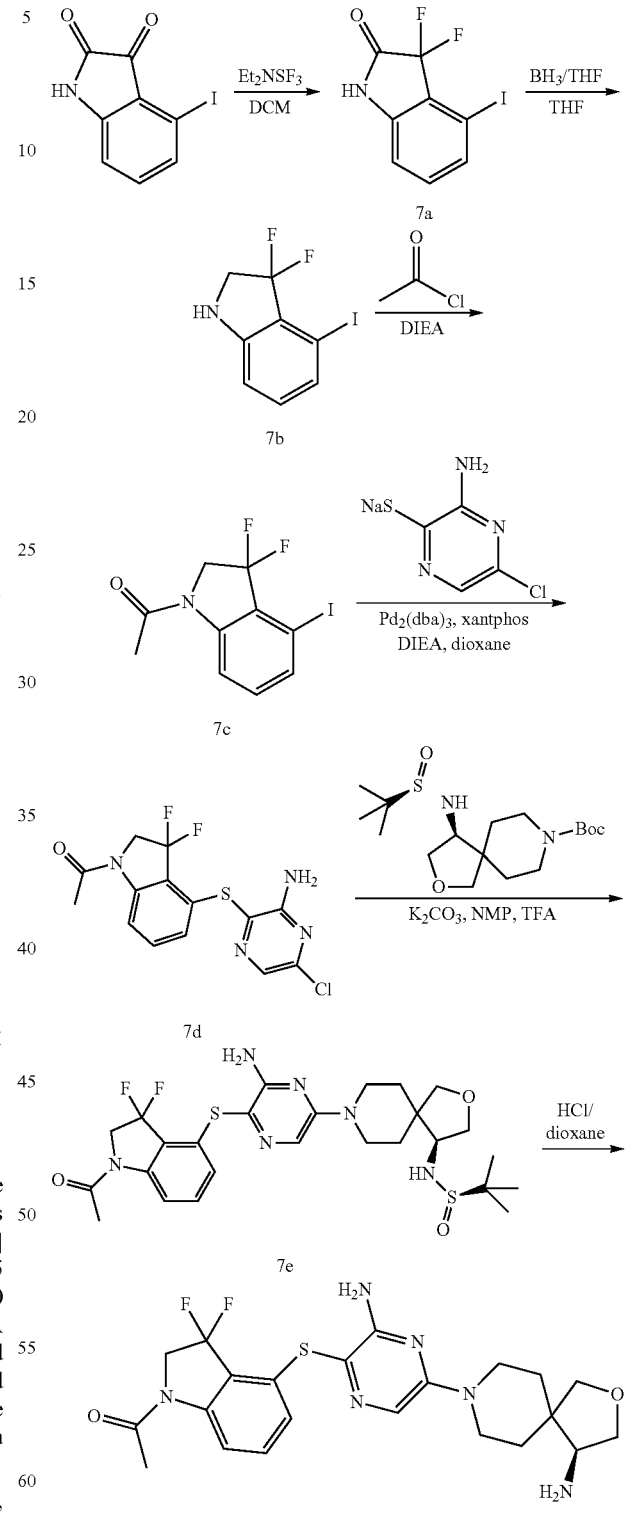

A solution of 4-iodoindoline-2,3-dione (35.00 g, 128.19 mmol) in DCM (300 mL) was added diethylaminosulfurtrifluoride (62.00 g, 387.12 mmol) dropwise at 0° C. The mixture was stirred overnight at RT. After completion of the reaction, the mixture was dropwised into a solution of sodium hydrogen carbonate in water (85 g/400 mL), the two layers were separated and aqueous layer was extracted with DCM (150 mL×2). The combined organic phases were dried over anhydrous Na$_2$SO$_4$, filtered and the volatiles were removed under reduced pressure. The residue was purified by column chromatography to afford the compound 7a as a off white solid (24.01 g, 63.4%). MS: 296 (M+H)$^+$.

A solution of the compound 7a (24.00 g, 81.34 mmol) in THF (100 mL) was stirred at 0° C., BH$_3$/THF (290 mL, 1M) was added dropwise, the ice-water bath was removed after the adding was completed and the mixture was stirred at RT for another 1 hour, TLC showed the reaction was completed. The mixture was quenched with 10% citric acid solution (50 mL) at 0° C., water (200 mL) was added, extracted with EA (200 mL×2), the organic phase was washed with brine (200 mL×2), dried over anhydrous Na$_2$SO$_4$, filtered and the solvent was removed until about 300 mL remained under reduced pressure, and compound 7b was used immediately for the next step without further purification. MS: 282 (M+H)$^+$.

A mixture of the compound 7b in EA obtained from the last step and DIEA (19 mL, 161.71 mmol) was added acetyl chloride (12 mL, 169.68 mmol) dropwise at 0° C. After completion of the reaction, water was added (100 mL), the organic layer was separated and aqueous layer was extracted with EA (50 mL). The combined organic layers were washed with brine (200 mL×2), dried over anhydrous Na$_2$SO$_4$, filtered and the volatiles were removed under reduced pressure, and the resultant residue was washed with EA-hexane=1:10 (80 mL) to afford the compound 7c (21.30 g, 81.0%). MS: 324 (M+H)$^+$.

A mixture of the compound 7c (10.00 g, 30.95 mol), sodium 3-amino-5-chloropyrazine-2-thiolate (6.28 g, 34.21 mmol), Pd$_2$(dba)$_3$ (1.40 g, 1.55 mmol), Xantphos (1.80 g, 3.11 mmol) and DIEA (8.00 g, 62.13 mmol) in dioxane (120 mL) was stirred at 70° C. under N$_2$ for about 5 hours. The solution was cooled to RT and filtered, the filtrate was removed under reduced pressure, and the resultant residue was washed with EA (50 mL), and filtrated to afford the compound 7d (9.92 g, 89.8%). MS: 357 (M+H)$^+$.

A mixture of (S)-tert-butyl 4-((R)-1,1-dimethylethylsulfinamido)-2-oxa-8-azaspiro[4.5]decane-8-carboxylate (508 mg, 1.41 mmol) and TFA (1 mL) in DCM (5 mL) was stirred at RT for 1 hour, the solvent was removed under reduced pressure, the resultant residue was added K$_2$CO$_3$ (0.81 g, 5.86 mmol), NMP (5 mL) and stirred for 5 min, then the compound 7d (250 mg, 0.70 mmol) was added, the mixture was heated to 75° C. for 2 hours, cooled and concentrated under reduced pressure, the residue was purified by column chromatography to afford the compound 7e (84 mg, 20.7%). MS: 581 (M+H)$^+$.

A solution of the compound 7e (185 mg, 0.32 mmol) in 3 mL of dioxane was added HCl/dioxane (1.2 mL, 4M). The mixture was stirred at RT. After completion of the reaction, the solution was removed under reduced pressure and the residue was washed with EA (5 mL) to afford the compound 7 (136 mg, 82.8%) as an HCl salt. MS: 477 (M+H)$^+$.

Example 8 Synthesis of Compound 8

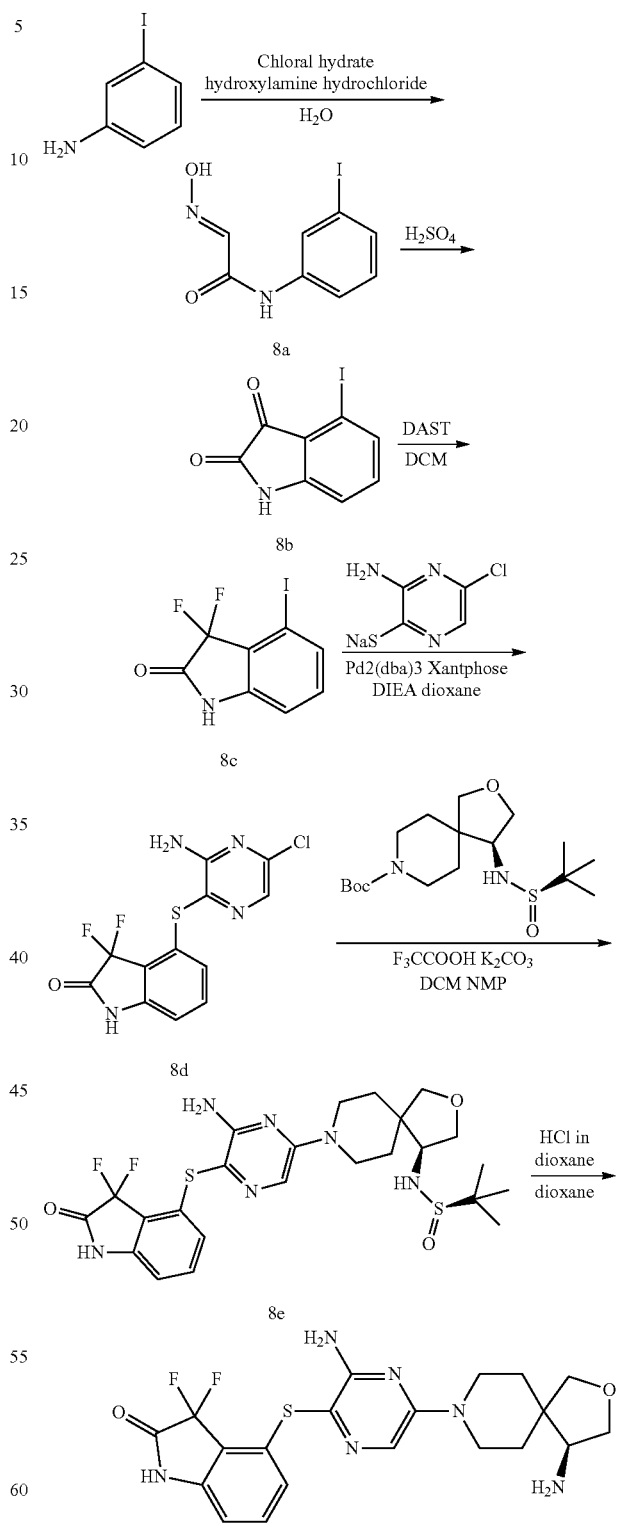

Chloral hydrate (50.02 g) and Na$_2$SO$_4$ (350.21 g) were dissolved in water (700 mL) in a 3 L beaker and warmed to 35° C. A warm solution of the appropriate commercial aniline derivative (60.45 g, 0.276 mol) in water (200 mL), and an aqueous solution of concentrated HCl (30 mL) was added (a white precipitate of the amine sulfate was formed), followed by a warm solution of hydroxylamine hydrochloride (61.18 g, 0.88 mol) in water (275 mL). The mixture was stirred by hand and heated on a hot plate (a thick paste formed at 75-70° C.) at 80-90° C. for 2 hours and then allowed to cool for 1 hour, by which time the temperature had fallen to 50° C. and filtered. The pale cream product was washed by stirring with water (IL) and filtered. Drying overnight at 40° C. gave the compound 8a (69.74 g, 87%). MS: 291 (M+H)+.

Sulfuric acid (1 L) was heated in a 3 L beaker on a hot plate to 60° C. and then removed. The compound 8a was added in portion with stirring over 30 mins so that the temperature did not exceed 65° C. The mixture was then heated to 80° C. for 15 mins, allowed to cool to 70° C., and cooled on ice. The solution was poured on to crushed ice (5 L) and left to stand for 1 hour before filtering the orange-red precipitate. The product was washed by stirring with water (400 mL) and filtered to give a mixture of the compound 8b and 6-iodoindoline-2,3-dione. The crude product was dissolved in a solution of NaOH (20 g) in water (200 mL) at 60° C. and then acidified with acetic acid to pH=4.9. After standing 0.5 hour and cooling to 35° C., the compound 8b precipitate was filtered and washed with water (50 mL) (38.37 g, 59%). MS: 274 (M+H)+.

A mixture of the compound 8b (2.31 g, 8.46 mmol), DAST (4.10 g, 25.43 mmol) and DCM (100 mL) was stirred at RT for 24 hours. The mixture was quenched by addition of NaHCO3 solution and then filtered to give the crude product, the crude product was washed with Hexane to afford the compound 8c (2.14 g, 86%). MS: 294 (M−H)+.

A mixture of the compound 8c (1.01 g, 3.42 mmol), Pd2(dba)3 (100 mg, 0.34 mmol), Xantphos (100 mg, 0.34 mmol), DIEA (883 mg, 6.84 mmol) and dioxane (30 mL) was stirred at 80° C. for 30 mins. sodium 3-amino-5-chloropyrazine-2-thiolate (628 mg, 3.42 mmol) was added then stirred for another 3 hours at 80° C. The mixture was cooled and the volatiles were removed under reduced pressure, the residue was purified by column chromatography to afford the compound 8d (545 mg, 48%). MS: 329 (M+H)+.

A mixture of (S)-tert-butyl 4-((R)-1,1-dimethylethylsulfinamido)-2-oxa-8-azaspiro[4.5]decane-8-carboxylate (1.18 g, 3.27 mmol), TFA (5 mL) and DCM (20 mL) was stirred at room temperature for 2 hours. The volatiles were removed under reduced pressure. The residue was added the compound 8d (542 mg, 1.65 mmol), K2CO3 (1.82 g, 13.20 mmol) and NMP (12 mL) and stirred at 80° C. for 10 hours. It was quenched by addition of water (40 mL), then exacted with EA (30 mL×5), the combined organic phases were washed with brine (100 mL), dried over anhydrous Na2SO4, filtered and the volatiles were removed under reduced pressure, the residue was purified by column chromatography to afford the compound 8e (138 mg, 15%). MS: 553 (M+H)+.

The compound 8e (138 mg, 0.25 mmol) was dissolved in dioxane (3 mL) and stirred. A solution of HCl/dioxane (0.5 mL, 4M) was added then the mixture was stirred at room temperature for 0.5 hour and the volatiles were removed under reduced pressure. The residue was washed with EA (10 mL) and filtered to afford the compound 8 as a yellow solid, HCl salt. MS: 449 (M+H)+.

Example 9 Synthesis of Compound 9

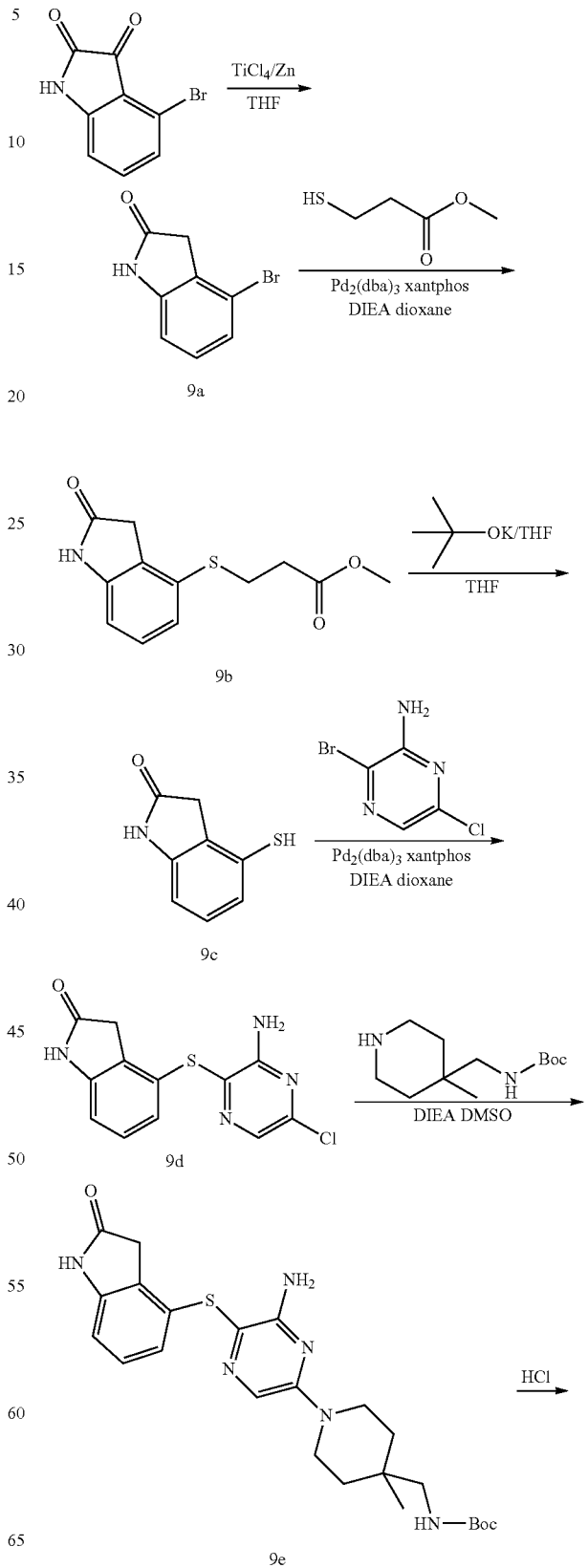

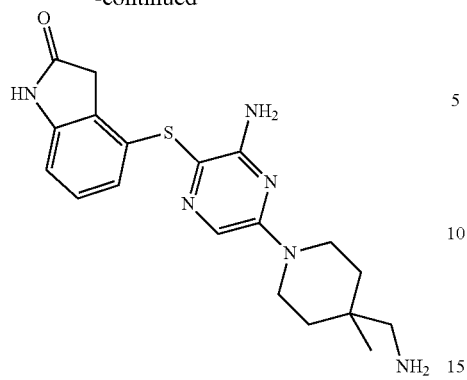

9

A mixture of Zn power (8.64 g, 132.13 mmol) and TiCl$_4$ (12.60 g, 66.42 mmol) in THF (100 mL) was stirred at 80° C. for 2 hours, then it was cooled to RT, a solution of 4-bromoindoline-2,3-dione (5.01 g, 22.16 mmol) in THF (100 mL) was added dropwise under N$_2$. After completion of the reaction, Hydrochloric acid solution (100 mL, 3M) was added, the mixture was extracted with DCM (50 mL×3), the organic phase was washed with brine (50 mL×2), dried over anhydrous Na$_2$SO$_4$, filtered and the solvent was removed under reduced pressure, the residue was purified by column chromatography to afford the compound 9a (2.63 g, 56.0%). MS: 212 (M+H)$^+$.

A mixture of the compound 9a (1.00 g, 4.72 mmol), methyl 3-mercaptopropanoate (1.13 g, 9.40 mmol), Pd$_2$(dba)$_3$ (0.15 g, 0.16 mmol), Xantphos (0.20 g, 0.35 mmol) and DIEA (1.23 g, 9.52 mmol) in dioxane (25 mL) was stirred overnight at 100° C. under N$_2$. the solvent was removed under reduced pressure, the residue was purified by column chromatography to afford the compound 9b (0.73 g, 61.5%). MS: 252 (M+H)$^+$.

A mixture of the compound 9b (1.65 g, 6.56 mmol) in THF (50 mL) was added t-BuOK/THF (15 mL, 1M) dropwise at −70° C., After completion of the reaction, it was quenched with Hydrochloric acid solution (20 mL, 1M) and extracted with EA (50 mL×3), the organic phase was washed with brine (100 mL×2), dried over anhydrous Na$_2$SO$_4$, filtered and the solvent was removed under reduced pressure, and the residue of the compound 9c was used immediately for the next step without further purification (1.08 g, 100%). MS: 166 (M+H)$^+$.

A mixture of the compound 9c (1.0 g, 6.54 mmol), 3-bromo-6-chloropyrazin-2-amine (1.37 g, 6.57 mmol), Pd$_2$(dba)$_3$ (0.31 g, 0.34 mmol), Xantphos (0.40 g, 0.69 mmol) and DIEA (1.70 g, 13.16 mmol) in dioxane (80 mL) was stirred at 100° C. under N$_2$ for 5 hours. The mixture was cooled to RT and filtered, the filtrate was removed under reduced pressure, the residue was purified by column chromatography to afford the compound 9d (0.53 g, 27.7%). MS: 293 (M+H)$^+$.

A mixture of the compound 9d (146 mg, 0.50 mmol), tert-butyl ((4-methylpiperidin-4-yl)methyl)carbamate (240 mg, 1.05 mmol) and DIEA (203 mg, 1.57 mmol) in DMSO (5 mL) was stirred at 80° C., after the reaction was completed, cooled to RT, water (20 mL) was added, the mixture was extracted with EA (20 mL×2), the organic phase was washed with brine (50 mL×2), dried over anhydrous Na$_2$SO$_4$, filtered and the solvent was removed under reduced pressure, the residue was purified by column chromatography to afford the compound 9e (99 mg, 40.8%). MS: 485 (M+H)$^+$.

A solution of the compound 9e (24 mg, 0.049 mmol) in 5 mL of DCM was bubbled into HCl gas at RT. After completion of the reaction, water (20 mL) was added, the mixture was washed with EA (20 mL×2), then the aqueous layer was adjusted to pH=11, extracted with DCM (20 mL×2), dried over anhydrous Na$_2$SO$_4$, filtered and the filtrate was removed under reduced pressure to afford the compound 9 (16 mg, 84.9%). MS: 385 (M+H)$^+$.

Example 10 Synthesis of Compound 10

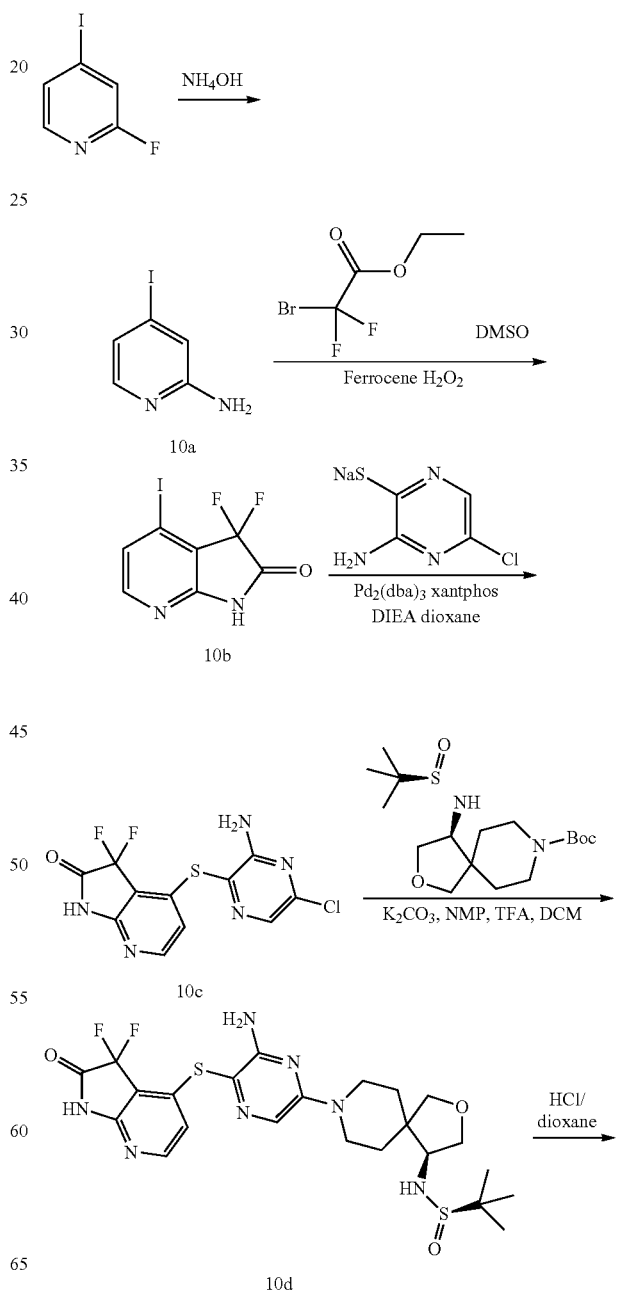

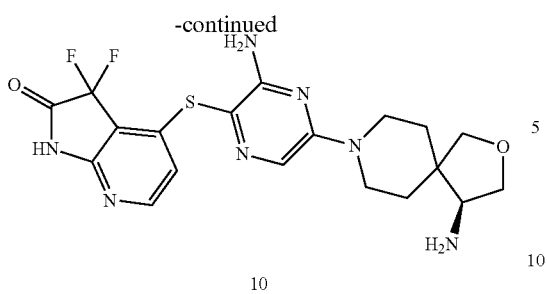

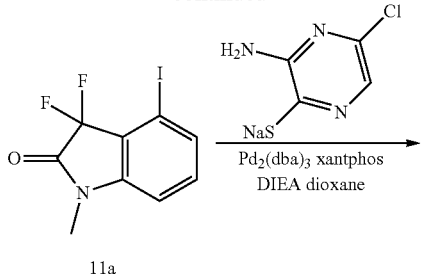

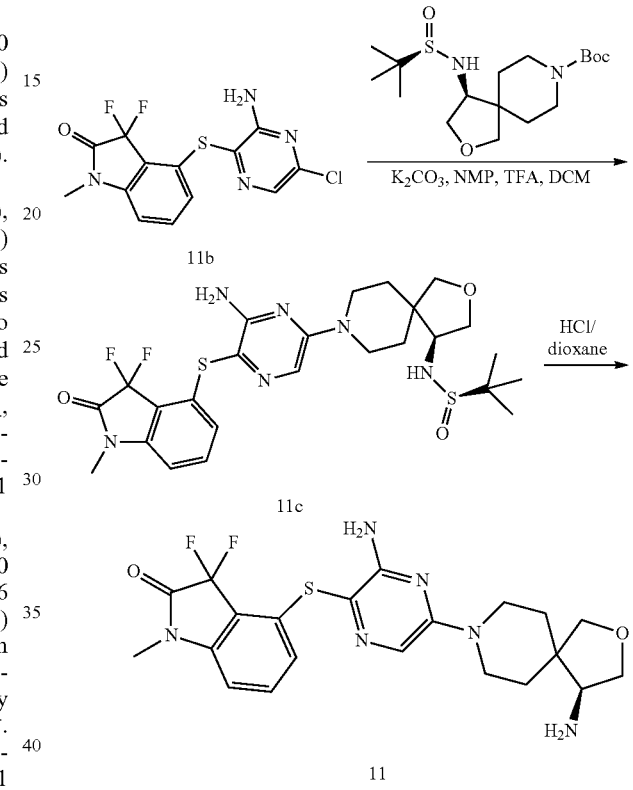

A mixture of 2-fluoro-4-iodopyridine (10.00 g, 43.50 mmol), ammonium hydroxide (100 mL) in DMSO (20 mL) was stirred at 100° C. for 40 hours. H$_2$O (100 mL) was added to the reaction mixture and the precipitate was filtered to afford the compound 10a as a brown solid (8.62 g, 90%). MS: 221 (M+H)$^+$.

To a solution of the compound 10a (8.00 g, 36.36 mmol), ethyl 2-bromo-2,2-difluoroacetate (18.46 g, 90.91 mmol) and Ferrocene (0.68 g, 3.64 mmol) in DMSO (70 mL) was added H$_2$O$_2$ (8 mL) at −5° C. The resulting mixture was stirred at 25° C. for 24 hours. H$_2$O (100 mL) was added to the reaction mixture, the aqueous solution was extracted with EA (100 mL×2). The combined organic extracts were washed with brine (50 mL), dried over anhydrous Na$_2$SO$_4$, filtered and the volatiles were removed under reduced pressure in vacuo. The residue was purified by column chromatography to afford the compound 10b as a yellow solid (3.41 g, 32%). MS: 297 (M+H)$^+$.

A mixture of the compound 10b (1.48 g, 5.00 mmol), sodium 3-amino-5-chloropyrazine-2-thiolate (0.92 g, 5.00 mmol), DIEA (1.29 g, 10.00 mmol), Pd$_2$(dba)$_3$ (0.15 g, 0.16 mmol), Xantphos (0.15 g, 0.26 mmol) in dioxane (20 mL) was heated to 95° C. under N$_2$ for 18 hours. The reaction mixture was filtered and concentrated under reduced pressure, the residue was purified by column chromatography afford the compound 10c (0.59 g, 36%). MS: 330 (M+H)$^+$.

A mixture of (S)-tert-butyl 4-((R)-1,1-dimethylethylsulfinamido)-2-oxa-8-azaspiro[4.5]decane-8-carboxylate (361 mg, 1.00 mmol), TFA (1 mL) in DCM (5 mL) was stirred at 25° C. for 1 hour. The reaction mixture was concentrated under reduced pressure, the residue was dissolved in NMP (8 mL), then the compound 10c (330 g, 1.00 mmol), K$_2$CO$_3$ (1.10 g, 8.00 mmol) was added to mixture and stirred at 80° C. for 1 hour. The reaction mixture was filtered and concentrated under reduced pressure, the residue was purified by Pre-TLC to afford the compound 10d (80 mg, 14%). MS: 554 (M+H)$^+$.

To a solution of the compound 10d (80 mg, 0.14 mmol) in DCM (10 mL) was added HCl/dioxane (1 mL, 4M). The resulting mixture was stirred at 25° C. for 1 hour and the precipitate was filtered to afford the compound 10 as a brown solid (10 mg, 16%). MS: 450 (M+H)$^+$.

Example 11 Synthesis of Compound 11

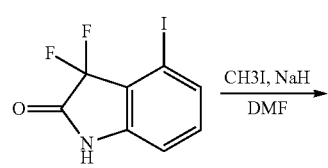

A mixture of the compound 7a (2.30 g, 7.80 mmol), NaH (0.94 g, 23.39 mmol, 60%) in DMF (30 mL) was stirred at 25° C. for 0.5 hour. Methyl iodide (3.32 g, 23.39 mmol) was added to the reaction mixture and stirred at 25° C. for 1 hour. Reaction was quenched with water (100 mL), the aqueous solution was extracted with EA (100 mL×2). The combined organic extracts were washed with brine (50 mL), dried over anhydrous Na$_2$SO$_4$, filtered and the volatiles were removed under reduced pressure in vacuo. The residue was purified by column chromatography to afford the compound 11a as a yellow solid (1.10 g, 46%). MS: 310 (M+H)$^+$.

A mixture of the compound 11a (1.10 g, 3.56 mmol), sodium 3-amino-5-chloropyrazine-2-thiolate (0.65 g, 3.56 mmol), DIEA (0.92 g, 7.12 mmol), Pd$_2$(dba)$_3$ (0.10 g, 0.11 mmol), Xantphos (0.10 g, 0.18 mmol) in dioxane (30 mL) was heated to 95° C. under N$_2$ for 18 hours. The reaction mixture was concentrated under reduced pressure, the residue was purified by column chromatography to afford the compound 11b (1.06 g, 87%). MS: 343 (M+H)$^+$.

A mixture of (S)-tert-butyl 4-((R)-1,1-dimethylethylsulfinamido)-2-oxa-8-azaspiro[4.5]decane-8-carboxylate (200 mg, 0.55 mmol), TFA (2 mL) in DCM (10 mL) was stirred at 25° C. for 1 hour. The reaction mixture was concentrated under reduced pressure. The residue was dissolved in NMP (8 mL), then the compound 11b (190 mg, 0.55 mmol), K$_2$CO$_3$ (613 mg, 4.44 mmol) was added to mixture and stirred at 90° C. for 24 hours. H$_2$O (50 mL) was added to the reaction. The aqueous solution was extracted with EA (50 mL×3). The combined organic extracts were washed with brine (50 mL), dried over anhydrous Na$_2$SO$_4$, filtered and the volatiles were removed in vacuo, the residue was purified by Pre-TLC to afford the compound 11c as a yellow solid (50 mg, 16%). MS: 567 (M+H)$^+$.

To a solution of the compound 11c (50 mg, 0.14 mmol) in DCM (5 mL) was added HCl/dioxane (1 mL, 4M). The resulting mixture was stirred at 25° C. for 1 hour. The reaction mixture was concentrated under reduced pressure, the residue was purified by Pre-TLC to afford the compound 11 (3 mg, 7%). MS: 463 (M+H)$^+$.

Example 12 Synthesis of Compound 12

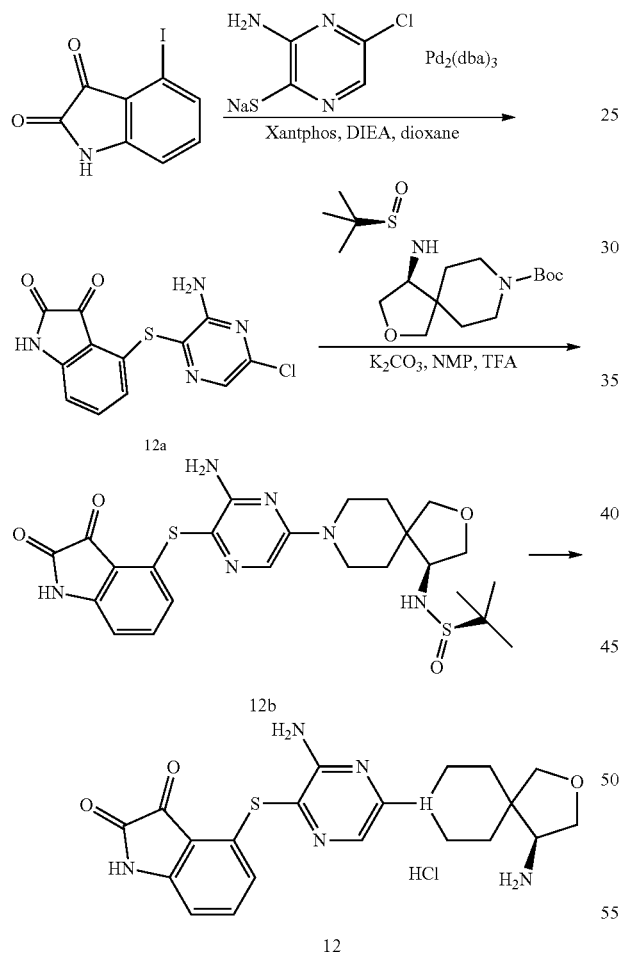

A mixture of 4-iodoindoline-2,3-dione (200 mg, 0.73 mmol), sodium 3-amino-5-chloropyrazine-2-thiolate (0.13 g, 0.73 mol), Pd$_2$(dba)$_3$ (20 mg, 0.02 mmol), Xantphos (20 mg, 0.035 mmol), DIEA (0.19 g, 1.46 mmol) in dioxane (10 mL) was stirred at 95° C. under N$_2$ for 2 hours. After completion of the reaction, the reaction mixture was concentrated under reduced pressure and the residue was purified by column chromatography to afford the compound 12a (0.19 g, 84.86%). MS: 307 (M+H)$^+$.

A mixture of (S)-tert-butyl 4-((R)-1,1-dimethylethylsulfinamido)-2-oxa-8-azaspiro[4.5]decane-8-carboxylate (0.28 g, 0.74 mmol), TFA (1 mL), and DCM (5 mL) was stirred at 20° C. for 1 hour. The mixture was concentrated under reduced pressure, and the residue was added DCM (10 mL), concentrated under reduced pressure again. A mixture of the residue, K$_2$CO$_3$ (0.68 g, 4.96 mmol), the compound 12a (0.19 g, 0.62 mmol) and NMP (5 mL) was heated to 80° C. for 18 hours. The reaction mixture was cooled and water (40 mL) was added, the resulting mixture was extracted with EA (20 mL×2). The combined organic extracts were washed with brine (30 mL), dried over anhydrous Na$_2$SO$_4$ and evaporated to dryness. The residue was purified by Pre-TLC to afford the compound 12b (18 mg, 5.47%). MS: 531 (M+H)$^+$.

A mixture of the compound 12b (39 mg, 0.08 mmol), HCl/dioxane (4 mol/L, 1 mL), and dioxane (2 mL) was stirred at 20° C. for 2 hours. The mixture was concentrated under reduced pressure, the residue was added EA (10 mL) and stirred for 5 mins. The precipitate was filtered to afford the compound 12 (4 mg, 25.47%) as an HCl salt. MS: 427 (M+H)$^+$.

Example 13 Synthesis of Compound 13

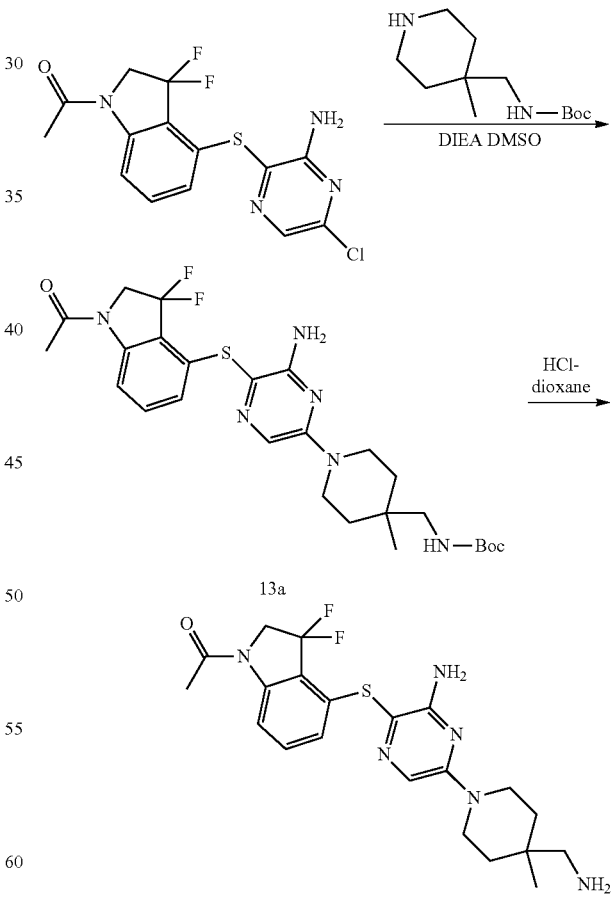

A mixture of the compound 7d (80 mg, 0.22 mol), DIEA (101 mg, 0.78 mmol) and tert-butyl ((4-methylpiperidin-4-yl)methyl)carbamate (200 mg, 0.88 mmol) in DMSO (5 mL)

was stirred at 80° C., after the reaction was completed, the mixture was cooled to RT, water (20 mL) was added, the mixture was extracted with EA (20 mL×2), the organic phase was washed with brine (50 mL×2), dried over anhydrous Na₂SO₄, filtered and the solvent was removed under reduced pressure, the residue was purified by column chromatography to afford the compound 13a (120 mg, 100%). MS: 549 (M+H)⁺.

A solution of the compound 13a (120 mg, 0.22 mmol) in dioxane (4 mL) was added HCl/dioxane (5 mL, 4M). The mixture was stirred at RT under ultrasonic for about 5 mins. After completion of the reaction, the solution was removed under reduced pressure and the residue was washed with EA (5 mL) to afford the compound 13 (85 mg, 79.7%) as an HCl salt. MS: 449 (M+H)⁺.

Example 14 Synthesis of Compound 14

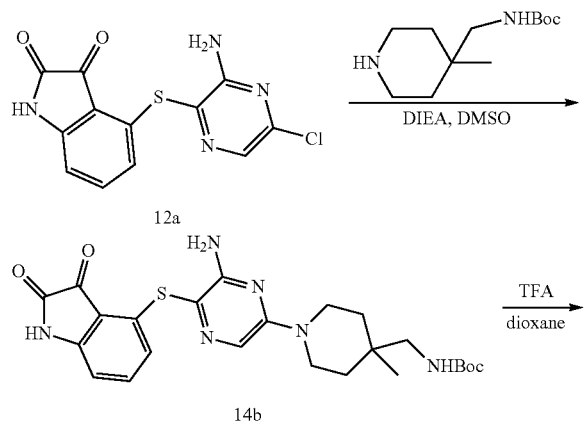

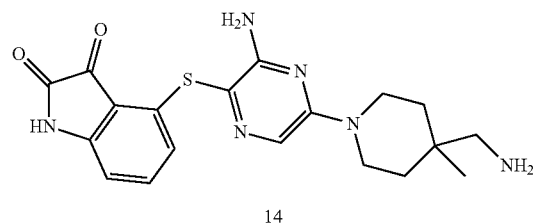

A mixture of the compound 12a (0.11 g, 0.36 mmol), tert-butyl ((4-methylpiperidin-4-yl)methyl)Carbamate (0.25 g, 1.08 mmol), DIEA (93 mg, 0.72 mmol) and DMSO (10 mL) was heated to 80° C. for 17 hours. The reaction mixture was cooled and water (50 mL) was added, the resulting mixture was extracted with EA (30 mL×2). The combined organic extracts were washed with brine (60 mL), dried over anhydrous Na₂SO₄, filtered and the solvent was removed under reduced pressure. The residue was purified by Pre-TLC to afford the compound 14b (0.13 g, 72.43%). MS: 499 (M+H)⁺.

A mixture of the compound 14b (0.13 g, 0.26 mmol), TFA (1 mL) and DCM (5 mL) was stirred at 20° C. for 2 hours. The mixture was concentrated under reduced pressure, the residue was added EA (10 mL), stirred for 5 min. The precipitate was filtered to afford the compound 14 (25 mg, 18.76%) as an TFA salt. MS: 399 (M+H)⁺.

| Ex No | Chemical Name | Structure | Physical Data (MS) (M + H)⁺ |
|---|---|---|---|
| 15 | 5-((2-amino-3-chloropyridin-4-yl)thio)-6-(4-(aminomethyl)-4-methylpiperidin-1-yl)pyrazin-2-amine | 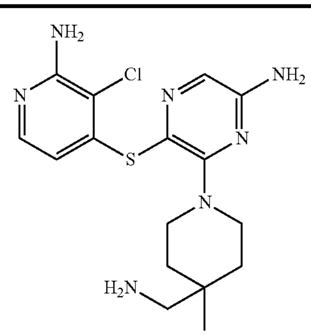 | 380 |
| 16 | N¹-(4-((3-amino-5-(4-(aminomethyl)-4-methylpiperidin-1-yl)pyrazin-2-yl)thio)-3-chloropyridin-2-yl)-N2,N2-dimethyl-oxalamide | 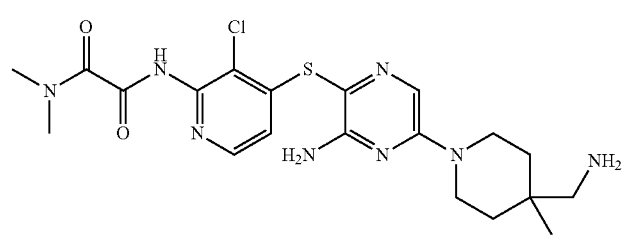 [SMILES: CN(C)C(=O)C(=O)Nc1nccc(Sc2ncc(N3CCC(C)(CN)CC3)nc2N)c1Cl] | 479 |

-continued

| Ex No | Chemical Name | Structure | Physical Data (MS) $(M+H)^+$ |
|---|---|---|---|
| 17 | tert-butyl ((1-(6-amino-5-((2-amino-3-chloropyridin-4-yl)thio)pyrazin-2-yl)-4-methylpiperidin-4-yl)methyl)carbamate | 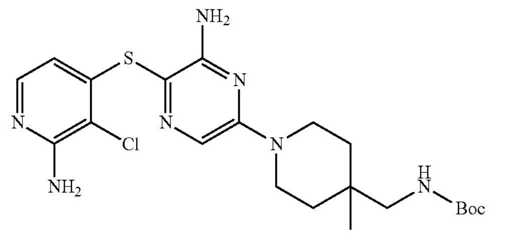 [SMILES: CC1(CNC(=O)OC(C)(C)C)CCN(c2cnc(Sc3ccnc(N)c3Cl)c(N)n2)CC1] | 480 |
| 18 | (S)-N1-(4-((3-amino-5-(4-amino-2-oxa-8-azaspiro[4.5]decan-8-yl)pyrazin-2-yl)thio)-3-chloropyridin-2-yl)-N2,N2-dimethyl-oxalamide | 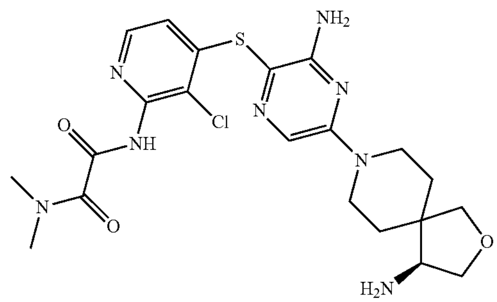 [SMILES: CN(C)C(=O)C(=O)Nc1nccc(Sc2ncc(N3CCC4(CC3)COC[C@H]4N)nc2N)c1Cl] | 507 |
| 19 | (S)-$N^1$-(3-((3-amino-5-(4-amino-2-oxa-8-azaspiro[4.5]decan-8-yl)pyrazin-2-yl)thio)-2-chlorophenyl)-$N^2$,$N^2$-dimethyloxalamide | 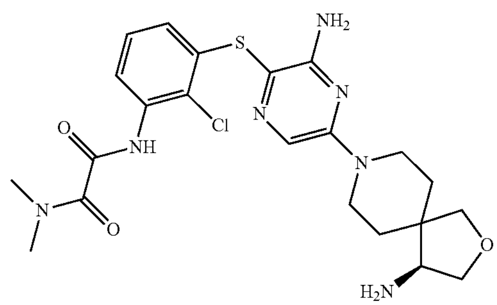 | 506 |
| 20 | $N^1$-(3-((3-amino-5-(4-(aminomethyl)-4-methylpiperidin-1-yl)pyrazin-2-yl)thio)-2-chlorophenyl)-$N^2$,$N^2$-dimethyloxalamide | 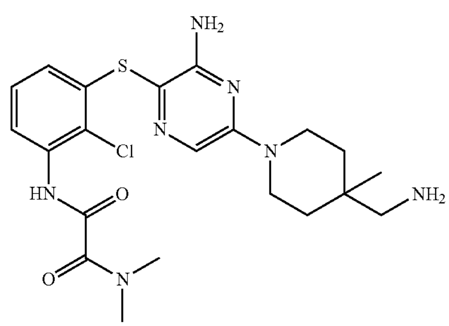 [SMILES: CN(C)C(=O)C(=O)Nc1cccc(Sc2ncc(N3CCC(C)(CN)CC3)nc2N)c1Cl] | 478 |
| 21 | N-(3-((3-amino-5-(4-(aminomethyl)-4-methylpiperidin-1-yl)pyrazin-2-yl)thio)-2-chlorophenyl)-3-(2-(dimethylamino)-2-oxo-acetyl)benzamide | 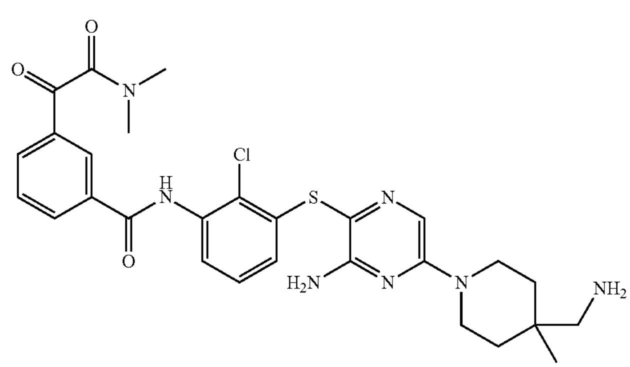 [SMILES: CN(C)C(=O)C(=O)c1cccc(C(=O)Nc2cccc(Sc3ncc(N4CCC(C)(CN)CC4)nc3N)c2Cl)c1] | 582 |

| Ex No | Chemical Name | Structure | Physical Data (MS) (M + H)+ |
|---|---|---|---|
| 22 | 2-(3-(3-(3-((3-amino-5-(4-(aminomethyl)-4-methylpiperidin-1-yl)pyrazin-2-yl)thio)-2-chlorophenyl)ureido)phenyl)-N,N-dimethyl-2-oxoacetamide | 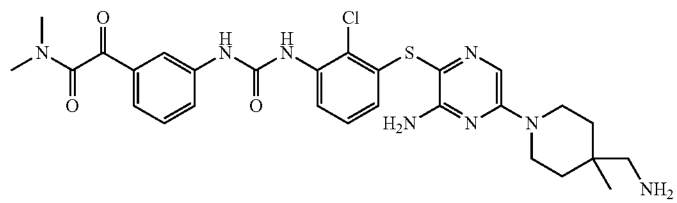 [SMILES: CN(C)C(=O)C(=O)c1cccc(NC(=O)Nc2cccc(Sc3ncc(N4CCC(C)(CN)CC4)nc3N)c2Cl)c1] | 597 |
| 23 | 2-(4-(3-((3-amino-5-(4-(aminomethyl)-4-methylpiperidin-1-yl)pyrazin-2-yl)thio)-2-chlorophenyl)ureido)phenyl)-N,N-dimethyl-2-oxoacetamide | 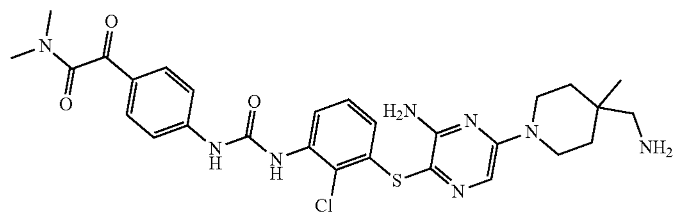 [SMILES: CN(C)C(=O)C(=O)c1ccc(NC(=O)Nc2cccc(Sc3ncc(N4CCC(C)(CN)CC4)nc3N)c2Cl)cc1] | 597 |
| 24 | 6-(4-(aminomethyl)-4-methylpiperidin-1-yl)-3-((3,4-dihydro-2H-benzo[b][1,4]oxazin-6-yl)thio)pyrazin-2-amine | 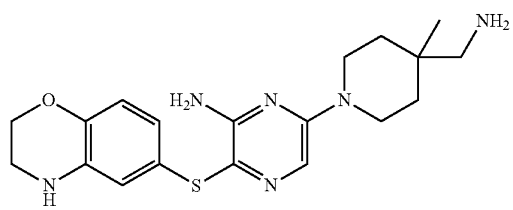 [SMILES: CC1(CN)CCN(c2cnc(Sc3ccc4c(c3)NCCO4)c(N)n2)CC1] | 387 |
| 25 | tert-butyl (1-(6-amino-5-((2-amino-3-chloropyridin-4-yl)thio)pyrazin-2-yl)-4-methylpiperidin-4-yl)carbamate | 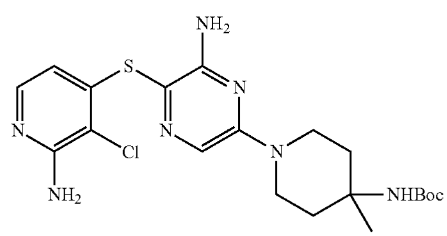 [SMILES: CC1(NC(=O)OC(C)(C)C)CCN(c2cnc(Sc3ccnc(N)c3Cl)c(N)n2)CC1] | 466 |
| 26 | tert-butyl (1-(5-((2-acrylamido-3-chloropyridin-4-yl)thio)-6-aminopyrazin-2-yl)-4-methylpiperidin-4-yl)carbamate | 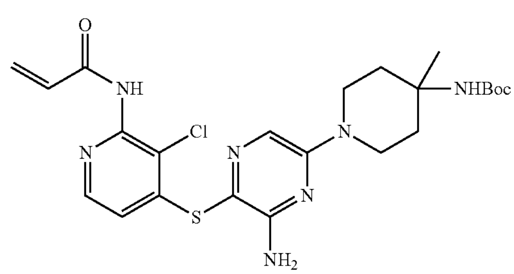 [SMILES: C=CC(=O)Nc1nccc(Sc2ncc(N3CCC(C)(NC(=O)OC(C)(C)C)CC3)nc2N)c1Cl] | 520 |
| 27 | tert-butyl (1-(6-amino-5-((3-chloro-2-(2-(dimethylamino)-2-oxoacetamido)pyridin-4-yl)thio)pyrazin-2-yl)-4-methylpiperidin-4-yl)carbamate | 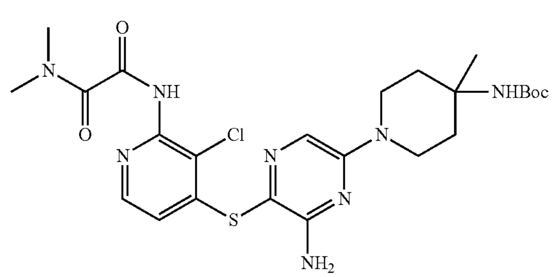 [SMILES: CN(C)C(=O)C(=O)Nc1nccc(Sc2ncc(N3CCC(C)(NC(=O)OC(C)(C)C)CC3)nc2N)c1Cl] | 565 |

-continued

| Ex No | Chemical Name | Structure | Physical Data (MS) (M + H)+ |
|---|---|---|---|
| 28 | tert-butyl (1-(6-amino-5-((2-chloro-3-(2-(dimethylamino)-2-oxoacetamido)phenyl)thio)pyrazin-2-yl)-4-methylpiperidin-4-yl)carbamate | 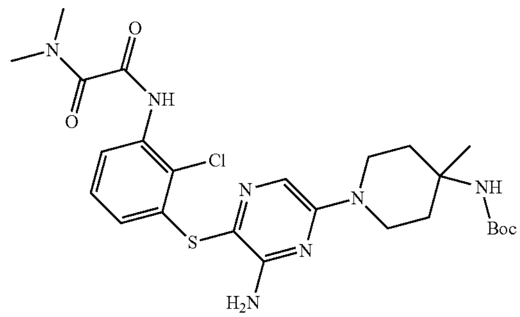 [SMILES: CN(C)C(=O)C(=O)Nc1cccc(Sc2ncc(N3CCC(C)(NC(=O)OC(C)(C)C)CC3)nc2N)c1Cl] | 564 |
| 29 | N$^1$-(3-((3-amino-5-(4-amino-4-methylpiperidin-1-yl)pyrazin-2-yl)thio)-2-chlorophenyl)-N$^2$,N$^2$-dimethyloxalamide | 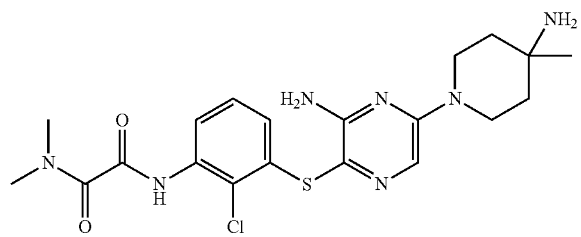 | 464 |
| 30 | tert-butyl (1-(6-amino-5-((3-amino-2-chlorophenyl)thio)pyrazin-2-yl)-4-methylpiperidin-4-yl)carbamate | 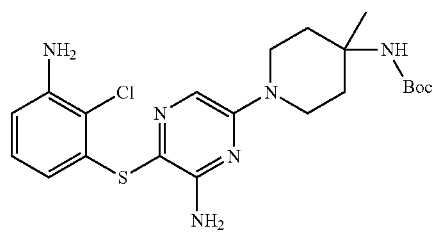 [SMILES: CC1(NC(=O)OC(C)(C)C)CCN(c2cnc(Sc3cccc(N)c3Cl)c(N)n2)CC1] | 465 |
| 31 | N-(3-((3-amino-5-(4-amino-4-methylpiperidin-1-yl)pyrazin-2-yl)thio)-2-chlorophenyl)-2-oxo-2-(p-tolyl)acetamide | 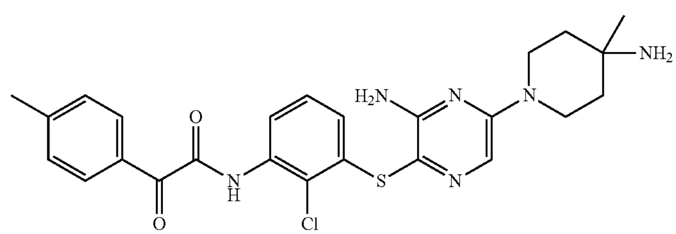 [SMILES: Cc1ccc(C(=O)C(=O)Nc2cccc(Sc3ncc(N4CCC(C)(N)CC4)nc3N)c2Cl)cc1] | 511 |
| 32 | tert-butyl (1-(5-((3-acrylamido-2-chlorophenyl)thio)-6-aminopyrazin-2-yl)-4-methylpiperidin-4-yl)carbamate | 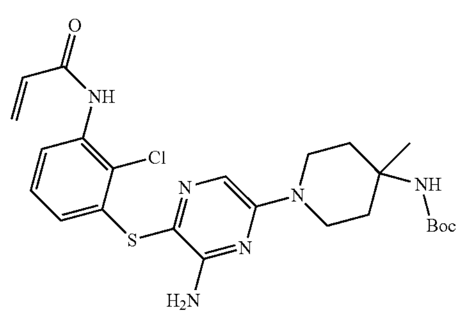 [SMILES: C=CC(=O)Nc1cccc(Sc2ncc(N3CCC(C)(NC(=O)OC(C)(C)C)CC3)nc2N)c1Cl] | 519 |
| 33 | 6-(3-amino-5-(4-amino-4-methylpiperidin-1-yl)pyrazin-2-yl)-2H-benzo[b][1,4]oxazin-3(4H)-one | 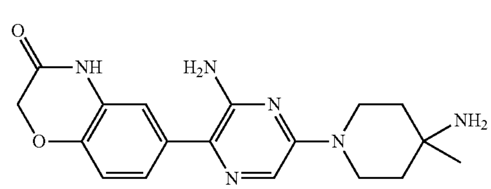 [SMILES: CC1(N)CCN(c2cnc(-c3ccc4c(c3)NC(=O)CO4)c(N)n2)CC1] | 355 |

-continued

| Ex No | Chemical Name | Structure | Physical Data (MS) (M + H)+ |
|---|---|---|---|
| 34 | N-(4-((3-amino-5-(4-amino-4-methylpiperidin-1-yl)pyrazin-2-yl)thio)-3-chloropyridin-2-yl)-4-(2-(dimethylamino)-2-oxoacetyl)benzamide | 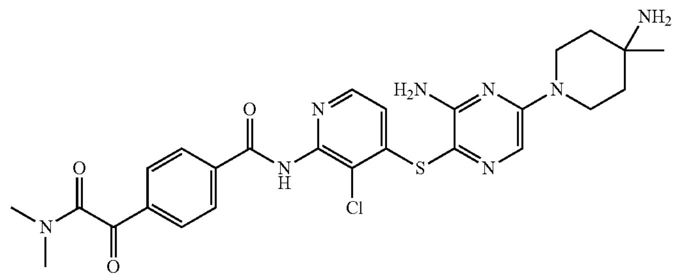 | 569 |
| 35 | N-(4-((3-amino-5-(4-(aminomethyl)-4-methylpiperidin-1-yl)pyrazin-2-yl)thio)-3-chloropyridin-2-yl)-4-(2-(dimethylamino)-2-oxoacetyl)benzamide | 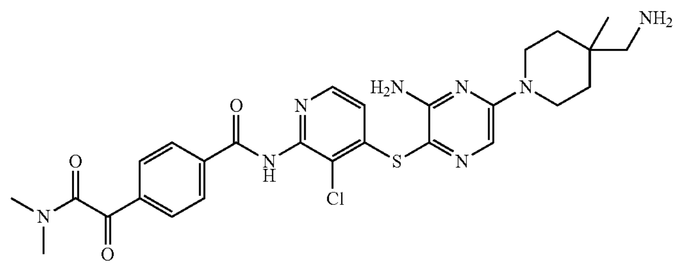 [SMILES: CN(C)C(=O)C(=O)c1ccc(C(=O)Nc2nccc(Sc3ncc(N4CCC(C)(CN)CC4)nc3N)c2Cl)cc1] | 583 |
| 36 | N-(3-((3-amino-5-(4-(aminomethyl)-4-methylpiperidin-1-yl)pyrazin-2-yl)thio)-2-chlorophenyl)-4-(2-(dimethylamino)-2-oxoacetyl)benzamide | 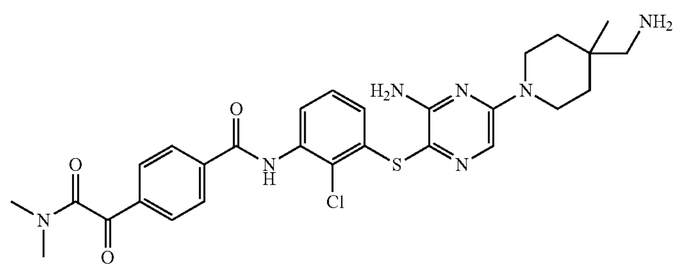 | 582 |
| 37 | 5-((2-amino-3-chloropyridin-4-yl)thio)-N2-cyclohexylpyrazine-2,6-diamine | 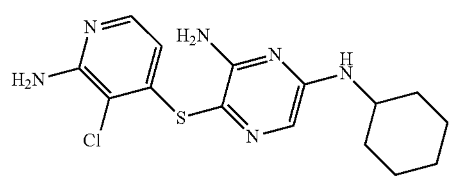 [SMILES: Nc1nc(NC2CCCCC2)cnc1Sc1ccnc(N)c1Cl] | 351 |
| 38 | (S)-8-(5-((1H-pyrrolo[2,3-b]pyridin-4-yl)thio)-6-aminopyrazin-2-yl)-2-oxa-8-azaspiro[4.5]decan-4-amine | 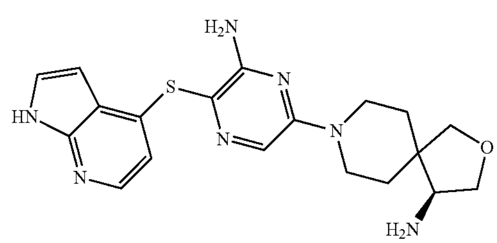 [SMILES: Nc1nc(N2CCC3(CC2)COC[C@H]3N)cnc1Sc1ccnc2[nH]ccc12] | 398 |
| 39 | (S)-8-(6-amino-5-((3,3-dimethylindolin-4-yl)thio)pyrazin-2-yl)-2-oxa-8-azaspiro[4.5]decan-4-amine | 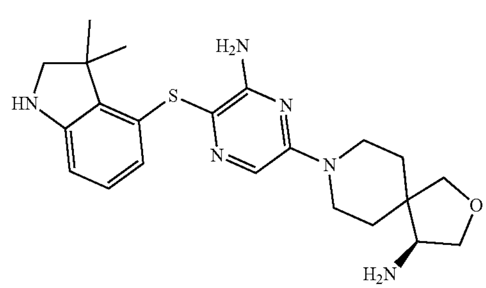 [SMILES: CC1(C)CNc2cccc(Sc3ncc(N4CCC5(CC4)COC[C@H]5N)nc3N)c21] | 427 |

| Ex No | Chemical Name | Structure | Physical Data (MS) (M + H)+ |
|---|---|---|---|
| 40 | (S)-8-(6-amino-5-((3-fluoro-1H-indol-4-yl)thio)pyrazin-2-yl)-2-oxa-8-azaspiro[4.5]decan-4-amine | 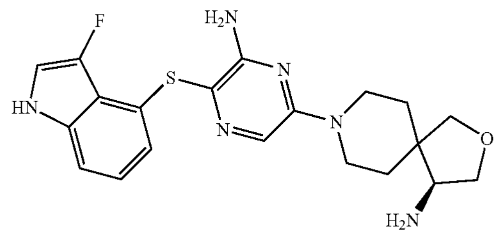 [SMILES: Nc1nc(N2CCC3(CC2)COC[C@H]3N)cnc1Sc1cccc2[nH]cc(F)c12] | 415 |
| 41 | 5-((2-amino-3-chloropyridin-4-yl)thio)-N2-(4-(aminomethyl)-4-methylcyclohexyl)pyrazine-2,6-diamine | 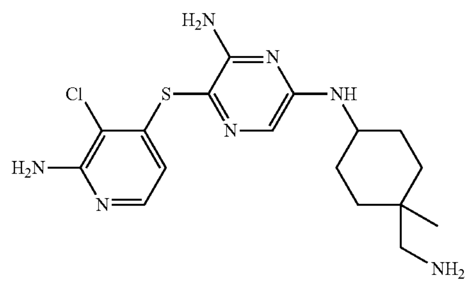 [SMILES: CC1(CN)CCC(Nc2cnc(Sc3ccnc(N)c3Cl)c(N)n2)CC1] | 394 |
| 42 | (S)-8-(5-((1H-indol-4-yl)thio)-6-amino-pyrazin-2-yl)-2-oxa-8-azaspiro[4.5]decan-4-amine | 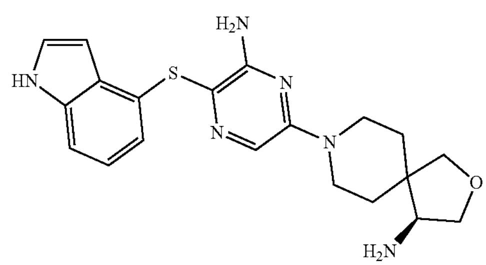 [SMILES: Nc1nc(N2CCC3(CC2)COC[C@H]3N)cnc1Sc1cccc2[nH]ccc12] | 397 |
| 43 | (S)-1-(4-((3-amino-5-(4-amino-2-oxa-8-azaspiro[4.5]decan-8-yl)pyrazin-2-yl)thio)-1H-indol-1-yl)ethanone | 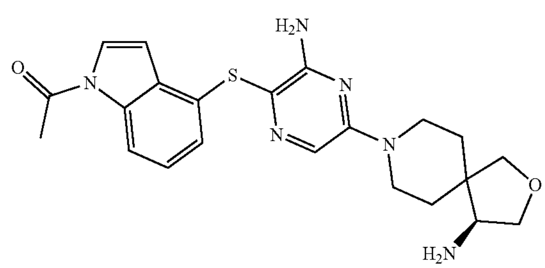 [SMILES: CC(=O)n1ccc2c(Sc3ncc(N4CCC5(CC4)COC[C@H]5N)nc3N)cccc21] | 439 |
| 44 | 5-((2-amino-3-chloropyridin-4-yl)thio)-N2-(4-amino-4-methylcyclohexyl)pyrazine-2,6-diamine | 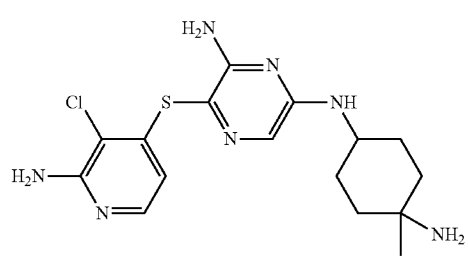 [SMILES: CC1(N)CCC(Nc2cnc(Sc3ccnc(N)c3Cl)c(N)n2)CC1] | 380 |

-continued

| Ex No | Chemical Name | Structure | Physical Data (MS) (M + H)+ |
|---|---|---|---|
| 45 | (S)-6-((3-amino-5-(4-amino-2-oxa-8-aza-spiro[4.5]decan-8-yl)pyrazin-2-yl)thio)-2H-benzo[b][1,4]oxazin-3(4H)-one | 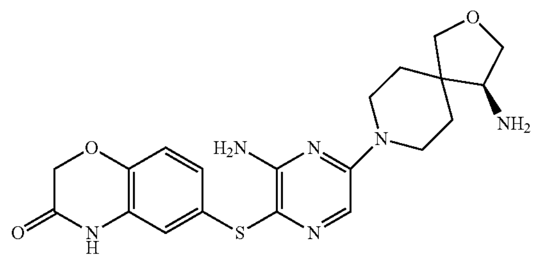 [SMILES: Nc1nc(N2CCC3(CC2)COC[C@H]3N)cnc1Sc1ccc2c(c1)NC(=O)CO2] | 429 |
| 46 | (S)-4-((3-amino-5-(4-amino-2-oxa-8-aza-spiro[4.5]decan-8-yl)pyrazin-2-yl)thio)-1,3,3-trimethylindolin-2-one | 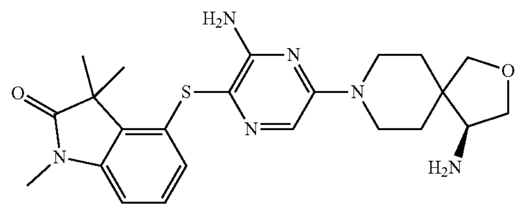 [SMILES: CN1C(=O)C(C)(C)c2c(Sc3ncc(N4CCC5(CC4)COC[C@H]5N)nc3N)cccc21] | 455 |
| 47 | (4S)-8-(6-amino-5-((3-fluoroindolin-4-yl)thio)pyrazin-2-yl)-2-oxa-8-azaspiro[4.5]decan-4-amine | 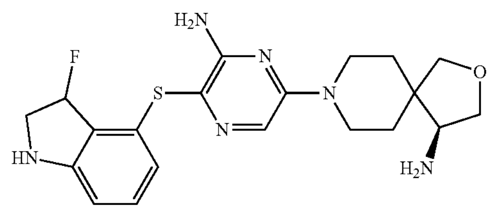 [SMILES: Nc1nc(N2CCC3(CC2)COC[C@H]3N)cnc1Sc1cccc2c1C(F)CN2] | 417 |
| 48 | 1-(4-((3-amino-5-((S)-4-amino-2-oxa-8-aza-spiro[4.5]decan-8-yl)pyrazin-2-yl)thio)-3-fluoro-3-methylindolin-1-yl)ethanone | 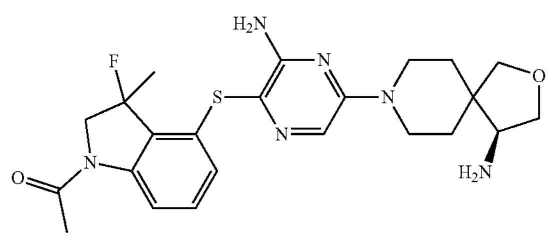 [SMILES: CC(=O)N1CC(C)(F)c2c(Sc3ncc(N4CCC5(CC4)COC[C@H]5N)nc3N)cccc21] | 473 |
| 49 | (S)-8-(6-amino-5-((3,3-difluoroindolin-4-yl)thio)pyrazin-2-yl)-2-oxa-8-azaspiro[4.5]decan-4-amine | 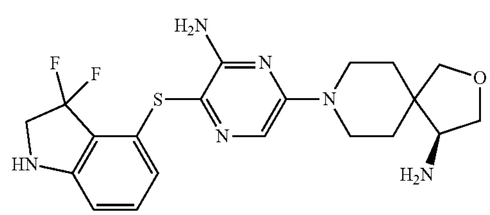 [SMILES: Nc1nc(N2CCC3(CC2)COC[C@H]3N)cnc1Sc1cccc2c1C(F)(F)CN2] | 435 |
| 50 | 1-(4-((3-amino-5-((S)-4-amino-2-oxaspiro[4.5]decan-8-yl)pyrazin-2-yl)thio)-3-methyl-indolin-1-yl)ethanone | 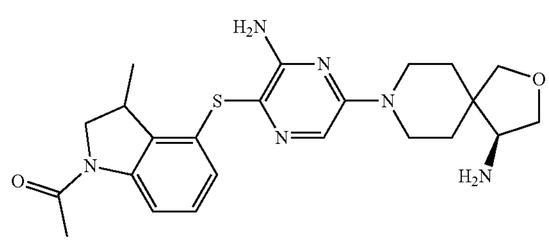 [SMILES: CC(=O)N1CC(C)c2c(Sc3ncc(N4CCC5(CC4)COC[C@H]5N)nc3N)cccc21] | 454 |

| Ex No | Chemical Name | Structure | Physical Data (MS) (M + H)+ |
|---|---|---|---|
| 51 | (S)-8-(6-amino-5-((8-chloro-4,4-difluoro-1,2,3,4-tetrahydroquinolin-5-yl)thio)pyrazin-2-yl)-2-oxa-8-azaspiro[4.5]decan-4-amine | 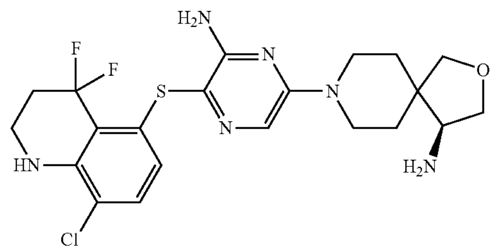 [SMILES: Nc1nc(N2CCC3(CC2)COC[C@H]3N)cnc1Sc1ccc(Cl)c2c1C(F)(F)CCN2] | 483 |
| 52 | (4S)-8-(6-amino-5-((8-chloro-4-fluoro-1,2,3,4-tetrahydroquinolin-5-yl)thio)pyrazin-2-yl)-2-oxa-8-azaspiro[4.5]decan-4-amine | 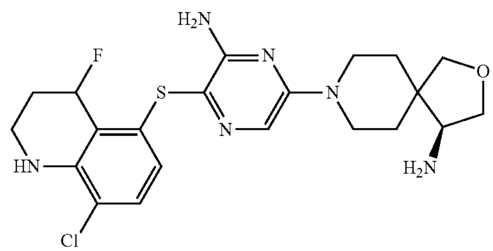 [SMILES: Nc1nc(N2CCC3(CC2)COC[C@H]3N)cnc1Sc1ccc(Cl)c2c1C(F)CCN2] | 465 |
| 53 | (S)-8-(6-amino-5-((3,3-difluoro-1-methyl-indolin-4-yl)thio)pyrazin-2-yl)-2-oxa-8-azaspiro[4.5]decan-4-amine | 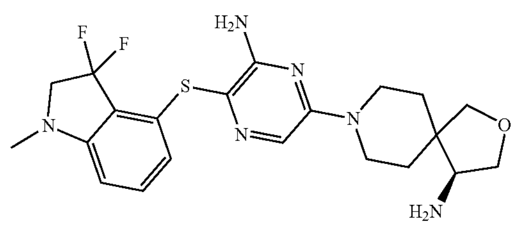 [SMILES: CN1CC(F)(F)c2c(Sc3ncc(N4CCC5(CC4)COC[C@H]5N)nc3N)cccc21] | 449 |
| 54 | (S)-6-((3-amino-5-(4-amino-2-oxa-8-azaspiro[4.5]decan-8-yl)pyrazin-2-yl)thio)-3,3-difluoroindolin-2-one | 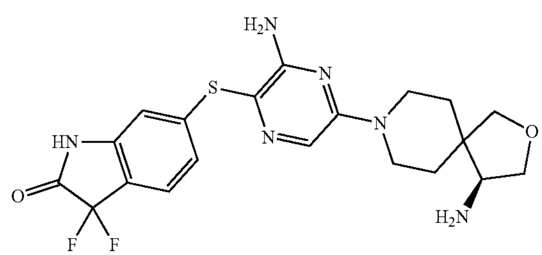 [SMILES: Nc1nc(N2CCC3(CC2)COC[C@H]3N)cnc1Sc1ccc2c(c1)NC(=O)C2(F)F] | 449 |
| 55 | 4-((3-amino-5-((S)-4-amino-2-oxa-8-azaspiro[4.5]decan-8-yl)pyrazin-2-yl)thio)-3-fluoroindolin-2-one | 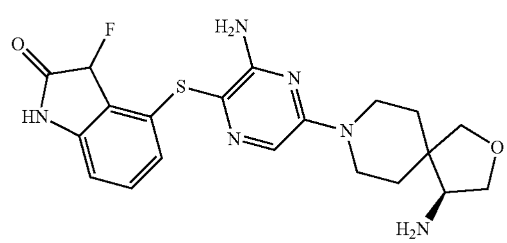 [SMILES: Nc1nc(N2CCC3(CC2)COC[C@H]3N)cnc1Sc1cccc2c1C(F)C(=O)N2] | 431 |
| 56 | (S)-8-(6-amino-5-((3,3-difluoro-2,3-dihydro-benzofuran-4-yl)thio)pyrazin-2-yl)-2-oxa-8-azaspiro[4.5]decan-4-amine | 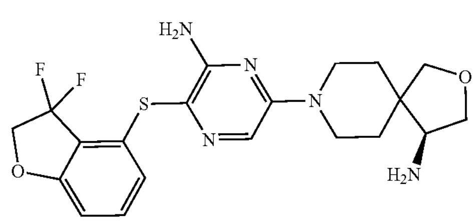 [SMILES: Nc1nc(N2CCC3(CC2)COC[C@H]3N)cnc1Sc1cccc2c1C(F)(F)CO2] | 436 |

-continued

| Ex No | Chemical Name | Structure | Physical Data (MS) (M + H)+ |
|---|---|---|---|
| 57 | (S)-8-(6-amino-5-((4,4-difluorochroman-5-yl)thio)pyrazin-2-yl)-2-oxa-8-azaspiro[4.5]decan-4-amine | 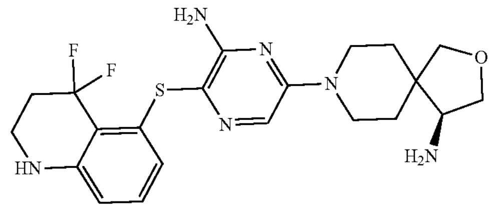 [SMILES: Nc1nc(N2CCC3(CC2)COC[C@H]3N)cnc1Sc1cccc2c1C(F)(F)CCN2] | 450 |
| 58 | 4-((3-amino-5-((S)-4-amino-2-oxa-8-azaspiro[4.5]decan-8-yl)pyrazin-2-yl)thio)-3-fluoro-1-methyl-3-(trifluoromethyl)indolin-2-one | 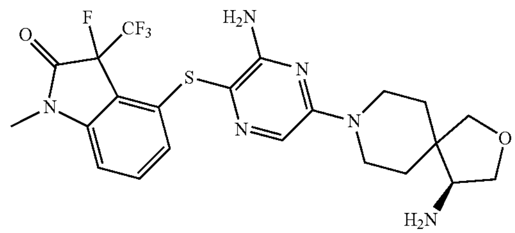 [SMILES: CN1C(=O)C(F)(C(F)(F)F)c2c(Sc3ncc(N4CCC5(CC4)COC[C@H]5N)nc3N)cccc21] | 513 |
| 59 | (S)-6-((3-amino-5-(4-amino-2-oxa-8-azaspiro[4.5]decan-8-yl)pyrazin-2-yl)thio)-7-chloroindolin-2-one | 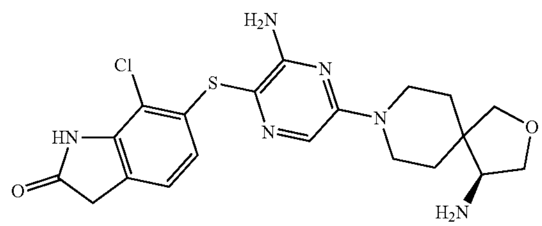 [SMILES: Nc1nc(N2CCC3(CC2)COC[C@H]3N)cnc1Sc1ccc2c(c1Cl)NC(=O)C2] | 447 |
| 60 | (S)-8-(6-amino-5-((5-chloro-3,4-dihydro-2H-benzo[b][1,4]oxazin-6-yl)thio)pyrazin-2-yl)-2-oxa-8-azaspiro[4.5]decan-4-amine | 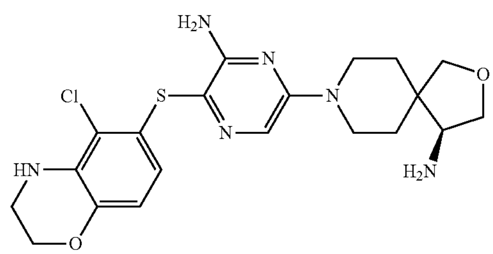 [SMILES: Nc1nc(N2CCC3(CC2)COC[C@H]3N)cnc1Sc1ccc2c(c1Cl)NCCO2] | 449 |
| 61 | (S)-7-((3-amino-5-(4-amino-2-oxa-8-azaspiro[4.5]decan-8-yl)pyrazin-2-yl)thio)-8-chloro-3,4-dihydroquinolin-2(1H)-one | 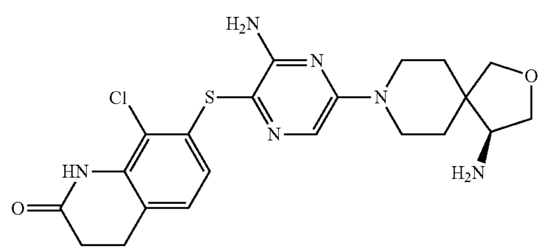 [SMILES: Nc1nc(N2CCC3(CC2)COC[C@H]3N)cnc1Sc1ccc2c(c1Cl)NC(=O)CC2] | 461 |
| 62 | (S)-6-((3-amino-5-(4-amino-2-oxa-8-azaspiro[4.5]decan-8-yl)pyrazin-2-yl)thio)-5-chloro-2H-benzo[b][1,4]oxazin-3(4H)-one | 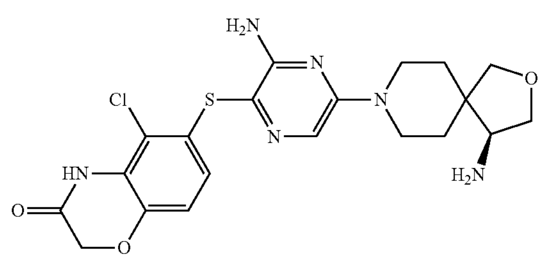 [SMILES: Nc1nc(N2CCC3(CC2)COC[C@H]3N)cnc1Sc1ccc2c(c1Cl)NC(=O)CO2] | 463 |

-continued

| Ex No | Chemical Name | Structure | Physical Data (MS) (M + H)+ |
|---|---|---|---|
| 63 | (S)-2-(3-((3-amino-5-(4-amino-2-oxa-8-azaspiro[4.5]decan-8-yl)pyrazin-2-yl)thio)-2-chlorophenyl)-N,N-dimethyl-2-oxoacetamide | 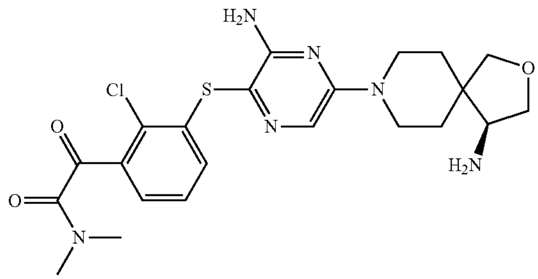 [SMILES: CN(C)C(=O)C(=O)c1cccc(Sc2ncc(N3CCC4(CC3)COC[C@H]4N)nc2N)c1Cl] | 491 |
| 64 | 4-((3-amino-5-(4-(aminomethyl)-4-methyl-piperidin-1-yl)pyrazin-2-yl)thio)-3,3-di-fluoro-1H-pyrrolo[2,3-b]pyridin-2(3H)-one | 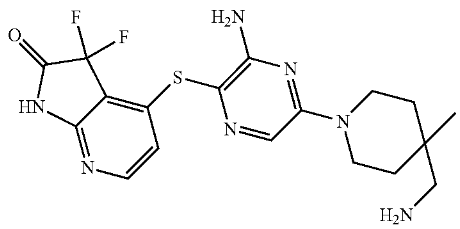 [SMILES: CC1(CN)CCN(c2cnc(Sc3ccnc4c3C(F)(F)C(=O)N4)c(N)n2)CC1] | 422 |
| 65 | (S)-4-((3-amino-5-(4-amino-2-oxa-8-aza-spiro[4.5]decan-8-yl)pyrazin-2-yl)thio)-1H-benzo[d]imidazol-2(3H)-one | 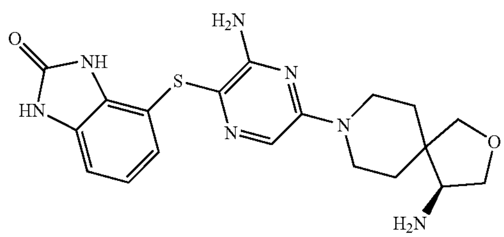 [SMILES: Nc1nc(N2CCC3(CC2)COC[C@H]3N)cnc1Sc1cccc2[nH]c(=O)[nH]c12] | 414 |
| 66 | (S)-4-((3-amino-5-(4-amino-2-oxa-8-aza-spiro[4.5]decan-8-yl)pyrazin-2-yl)thio)-1,3-dimethyl-1H-benzo[d]imidazol-2(3H)-one | 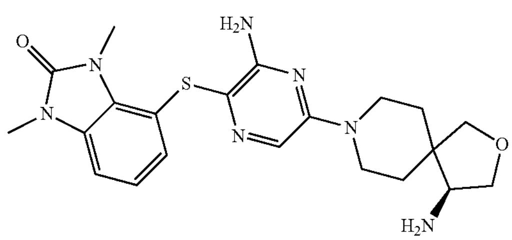 [SMILES: Cn1c(=O)n(C)c2c(Sc3ncc(N4CCC5(CC4)COC[C@H]5N)nc3N)cccc21] | 442 |
| 67 | (S)-8-(6-amino-5-((2,2-difluoro-2,3-dihydro-1H-benzo[d]imidazol-4-yl)thio)pyrazin-2-yl)-2-oxa-8-azaspiro[4.5]decan-4-amine | 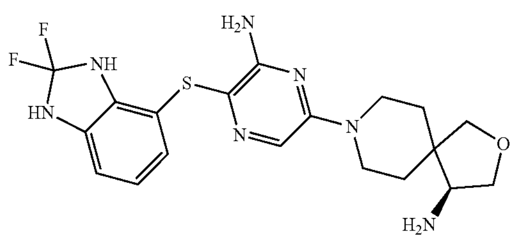 [SMILES: Nc1nc(N2CCC3(CC2)COC[C@H]3N)cnc1Sc1cccc2c1NC(F)(F)N2] | 436 |
| 68 | (S)-8-(6-amino-5-((2,2-difluoro-1,3-di-methyl-2,3-dihydro-1H-benzo[d]imidazol-4-yl)thio)pyrazin-2-yl)-2-oxa-8-azaspiro[4.5]decan-4-amine | 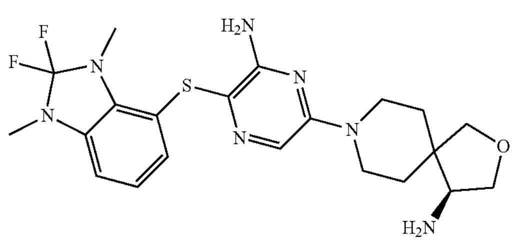 [SMILES: CN1c2cccc(Sc3ncc(N4CCC5(CC4)COC[C@H]5N)nc3N)c2N(C)C1(F)F] | 464 |

| Ex No | Chemical Name | Structure | Physical Data (MS) (M + H)+ |
|---|---|---|---|
| 69 | (4S)-8-(6-amino-5-((1-amino-3,3-difluoro-2,3-dihydro-1H-inden-4-yl)thio)pyrazin-2-yl)-2-oxa-8-azaspiro[4.5]decan-4-amine | 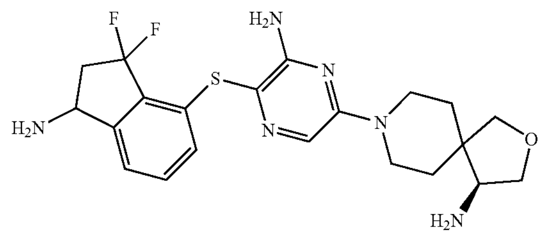 [SMILES: Nc1nc(N2CCC3(CC2)COC[C@H]3N)cnc1Sc1cccc2c1C(F)(F)CC2N] | 449 |
| 70 | (S)-5-((3-amino-5-(4-amino-2-oxa-8-azaspiro[4.5]decan-8-yl)pyrazin-2-yl)thio)-2-methyl-[1,2,4]triazolo[4,3-a]pyridin-3(2H)-one | 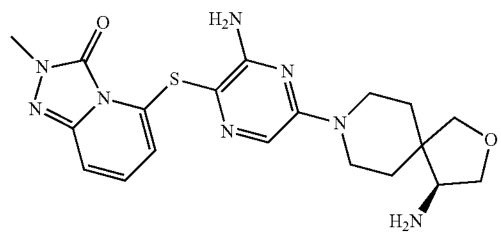 [SMILES: Cn1nc2cccc(Sc3ncc(N4CCC5(CC4)COC[C@H]5N)nc3N)n2c1=O] | 429 |
| 71 | (S)-8-(6-amino-5-((3,3-difluoro-2-methyl-2,3-dihydro-[1,2,4]triazolo[4,3-a]pyridin-5-yl)thio)pyrazin-2-yl)-2-oxa-8-azaspiro[4.5]decan-4-amine | 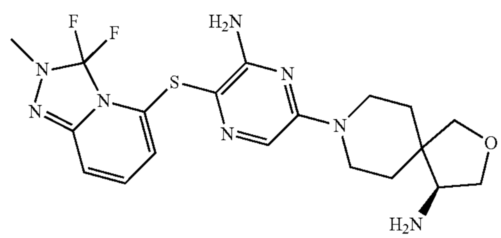 [SMILES: CN1N=C2C=CC=C(Sc3ncc(N4CCC5(CC4)COC[C@H]5N)nc3N)N2C1(F)F] | 451 |
| 72 | (S)-1-(4-((3-amino-5-(4-amino-2-oxa-8-azaspiro[4.5]decan-8-yl)pyrazin-2-yl)thio)indolin-1-yl)ethanone | 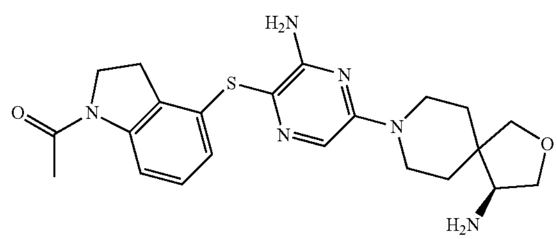 [SMILES: CC(=O)N1CCc2c(Sc3ncc(N4CCC5(CC4)COC[C@H]5N)nc3N)cccc21] | 441 |
| 73 | 1'-(6-amino-5-((2-amino-3-chloropyridin-4-yl)thio)pyrazin-2-yl)hexahydrospiro[cyclopenta[b]furan-5,4'-piperidin]-4-amine | 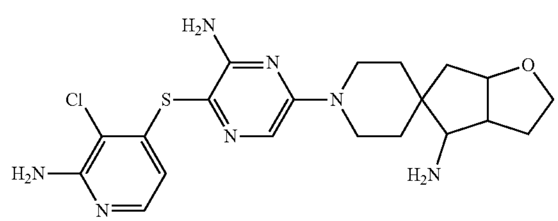 [SMILES: Nc1nc(N2CCC3(CC2)CC2OCCC2C3N)cnc1Sc1ccnc(N)c1Cl] | 448 |
| 74 | 1'-(6-amino-5-((2-amino-3-chloropyridin-4-yl)thio)pyrazin-2-yl)spiro[bicyclo[3.1.0]hexane-3,4'-piperidin]-2-amine | 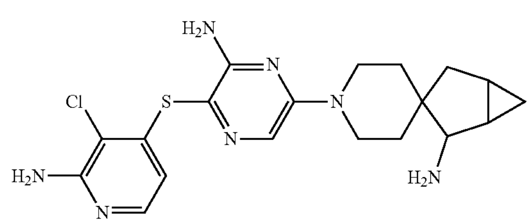 [SMILES: Nc1nc(N2CCC3(CC2)CC2CC2C3N)cnc1Sc1ccnc(N)c1Cl] | 418 |

| Ex No | Chemical Name | Structure | Physical Data (MS) (M + H)+ |
|---|---|---|---|
| 75 | 1'-amino-1-(6-amino-5-((2-amino-3-chloro-pyridin-4-yl)thio)pyrazin-2-yl)tetrahydro-spiro[piperidine-4,2'-pyrrolizin]-3'(1'H)-one | 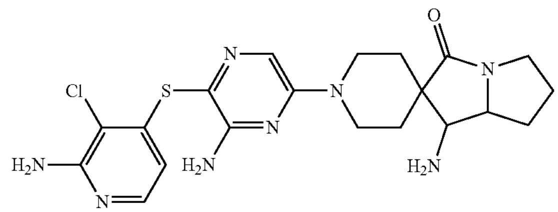 [SMILES: Nc1nc(N2CCC3(CC2)C(=O)N2CCCC2C3N)cnc1Sc1ccnc(N)c1Cl] | 461 |
| 76 | 1'-(6-amino-5-((2-amino-3-chloropyridin-4-yl)thio)pyrazin-2-yl)spiro[bicyclo[3.1.0]hexane-2,4'-piperidin]-3-amine | 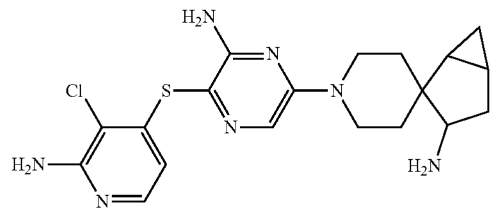 [SMILES: Nc1nc(N2CCC3(CC2)C(N)CC2CC23)cnc1Sc1ccnc(N)c1Cl] | 418 |

Pharmacological Testing

Example A. Phosphatase Assay (Single Dose Inhibition)

Assay Protocol:

For single dose inhibition assays using 6,8-difluoro-4-methylumbelliferyl phosphate (DiFMUP) as a substrate, SHP2 samples (diluted to 0.5 nM in reaction buffer) were incubated with dPEG8 peptide for 30 min in reaction buffer[60 mM 3,3-dimethyl glutarate (pH7.2), 75 mM NaCl, 75 mM KCl, and 1 mM EDTA, 0.05% Tween 20, 2 mM dithiothreitol (DTT)] to active the PTP. DMSO [0.5% (v/v)] or compounds (100 nM) were added to the mixture and incubated for 30 min at room temperature. Reactions were initiated by the addition of DiFMUP (12 μM; total reaction volume of 100 μL), and the fluorescence (excitation at 340 nm, emission at 450 nm) of the resulting solutions was measured on a 2104-0020 EnVision Xcite Multilabel Reader (PerkinElmer) after 30 min. The experiment is carried out in triplicate. The value for the control sample (DMSO) was set to 100%, and the values for the compound-treated samples were expressed as activity relative to the control sample. The inhibition of SHP2 by compounds of the invention were shown in table 1.

TABLE 1

| Example | SHP2 inhibition(%) | Example | SHP2 inhibition(%) |
|---|---|---|---|
| 3 @ 0.1 μM | 60 | 7 @ 0.1 μM | 79 |
| 8 @ 0.1 μM | 76 | 10 @ 0.1 μM | 81 |
| 20 @ 0.1 μM | 57 | 29 @ 0.1 μM | 47 |
| 31 @ 0.1 μM | 53 | 32 @ 0.1 μM | 49 |
| 34 @ 0.1 μM | 37 | 35 @ 0.1 μM | 30 |
| 38 @ 0.1 μM | 30 | 40 @ 0.1 μM | 71 |
| 42 @ 0.1 μM | 58 | 43 @ 0.1 μM | 43 |
| 58 @ 0.1 μM | 61 | 72 @ 0.1 μM | 31 |
| 74 @ 0.1 μM | 75 | 75 @ 0.1 μM | 35 |

Example B. Phosphatase Assays (IC50)

$IC_{50}$ values were estimated using 6,8-difluoro-4-methylumbelliferyl phosphate (DiFMUP) as a substrate, SHP2 samples (diluted to 0.5 nM in reaction buffer) were incubated with dPEG8 peptide for 30 min in reaction buffer[60 mM 3,3-dimethyl glutarate (pH7.2), 75 mM NaCl, 75 mM KCl, and 1 mM EDTA, 0.05% Tween 20, 2 mM dithiothreitol (DTT)] to active the PTP. DMSO [0.5% (v/v)] or compounds (concentrations ranging from 0.3 nM to 1 μM) were added to the mixture and incubated for 30 min at room temperature. Reactions were initiated by the addition of DiFMUP (12 μM; total reaction volume of 100 μL), and the fluorescence (excitation at 340 nm, emission at 450 nm) of the resulting solutions was measured on a 2104-0020 EnVision Xcite Multilabel Reader (PerkinElmer) after 30 min. The $IC_{50}$ results of the compounds of the invention were shown by table 2.

TABLE 2

| Example | $IC_{50}$ (nM) | Example | $IC_{50}$ (nM) |
|---|---|---|---|
| 7 @ | 25.8 | 8 @ | 21.4 |
| 10 @ | 30 | 40 @ | 40.6 |
| 74 @ | 8.3 | SHP099 | 84 |

Example C. Cell Proliferation Assay

KYSE-520 (1500 cells/well) were plated onto 96-well plates in 100 μL medium (RPMI-1640 containing 3% FBS for KYSE-520 cells, Gibco). For drug treatment, compounds of the invention at various concentrations were added 24 hours after cell plating. At day 8, 50 μL MTS/PMS reagents (Promega/Sigma) were added, and the absorbance value was determined according to the supplier's instruction (Promega). The $IC_{50}$ results of the compounds of the invention were shown by table 3.

TABLE 3

| Example | IC$_{50}$ (($\mu$M)) | Example | IC$_{50}$ (($\mu$M)) |
|---------|---------------------|---------|---------------------|
| 1 | 15.94 | 7 | 2.17 |
| 8 | 26.38 | 11 | 12.04 |
| 13 | 20.57 | 74 | 3.38 |

The compounds of the present invention are preferably formulated as pharmaceutical compositions administered by a variety of routes. Most preferably, such compositions are for oral administration. Such pharmaceutical compositions and processes for preparing the same are well known in the art. See, e.g., REMINGTON: THE SCIENCE AND PRACTICE OF PHARMACY (A. Gennaro, et al, eds., 19$^{th}$ ed., Mack Publishing Co., 1995). The compounds of Formula I are generally effective over a wide dosage range.

For example, dosages per day normally fall within the range of about 1 mg to about 200 mg total daily dose, preferably 1 mg to 150 mg total daily dose, more preferably 1 mg to 50 mg total daily dose. In some instances dosage levels below the lower limit of the aforesaid range may be more than adequate, while in other cases still larger doses may be employed. The above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

What is claimed is:

1. A compound which is:

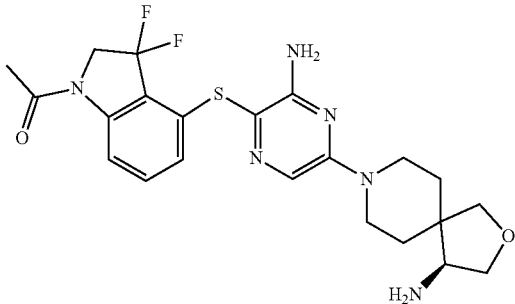 [SMILES: CC(=O)N1CC(F)(F)c2c(Sc3ncc(N4CCC5(CC4)COC[C@H]5N)nc3N)cccc21]

or a pharmaceutically acceptable salt thereof.

2. A compound which is:

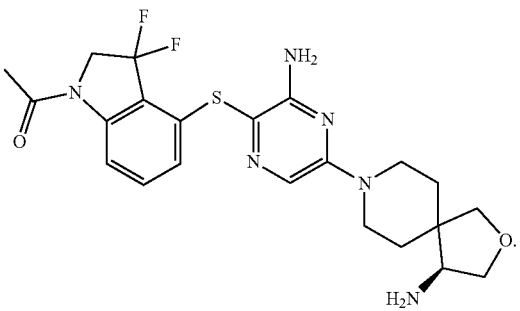 [SMILES: CC(=O)N1CC(F)(F)c2c(Sc3ncc(N4CCC5(CC4)COC[C@H]5N)nc3N)cccc21]

* * * * *